(12) United States Patent
Pelletier et al.

(10) Patent No.: US 6,376,652 B1
(45) Date of Patent: Apr. 23, 2002

(54) **COMPOSITIONS AND METHODS INVOLVING AN ESSENTIAL *STAPHYLOCOCCUS AUREUS* GENE AND ITS ENCODED PROTEIN**

(75) Inventors: Jerry Pelletier, Baie-D'Urfé ; Philippe Gros, St. Lambert; Mike DuBow, Montreal, all of (CA)

(73) Assignee: Phagetech, Inc., Quebec (CA)

( * ) Notice: Subject to any disclaimer, the term of this patent is extended or adjusted under 35 U.S.C. 154(b) by 0 days.

(21) Appl. No.: 09/470,512

(22) Filed: Dec. 22, 1999

Related U.S. Application Data

(63) Continuation-in-part of application No. 09/407,804, filed on Sep. 28, 1999.
(60) Provisional application No. 60/110,992, filed on Dec. 3, 1998.

(51) Int. Cl.[7] ................................................. C07K 14/00
(52) U.S. Cl. ....................................................... 530/350

(56) References Cited

PUBLICATIONS

Franken et al. 1996; J. Virology 70(11): 7819–7826.*
Klein et al. 1994; Microbiology 140:1133–1139.*
Tomb et al. 1997; Nature 388:539–547.*
Tarentino et al. 1993; J. Biol. Chem 268(13):9702–9708.*

* cited by examiner

*Primary Examiner*—Karen Cochrane Carlson
(74) *Attorney, Agent, or Firm*—Kathleen Williams; Palmer & Dodge, LLP

(57) ABSTRACT

This invention relates to newly identified polynucleotides and polypeptides, and their production and uses, as well as their variants, agonists and antagonists, and their uses. In particular, the invention relates to polynucleotides and polypeptides of a *Staphylococcus aureus* (*S. aureus*) DnaI related protein, as well as its variants, hereinafter referred to as "*S. aureus* DnaI", "*S. aureus* DnaI polypeptide(s)", and "*S. aureus* dnaI polynucleotides" as the case may be. Also, the invention relates to a specific interaction between the *S. aureus* DnaI related protein and a growth-inhibitory protein encoded by the *S. aureus* bacteriophage 77 genome. The phage ORF product interacts with the *S. aureus* DnaI polypeptide, and the invention contemplates use of this interaction target site for the basis of a drug screening assay. In addition, the invention relates to polynucleotides and polypeptides of a protein complex containing *S. aureus* DnaI and DnaC related proteins, as well as their variants.

6 Claims, 52 Drawing Sheets

SEQ ID NO:1

| | | | | | |
|---|---|---|---|---|---|
| 1 | ATGGGAGGAG | GACAGTCAAT | AATGAAGCAA | TTTAAAAGTA | TAATTAACAC | GTCGCAGGAC |
| 61 | TTTGAAAAAA | GAATAGAAAA | GATAAAAAAA | GAAGTAATCA | ATGACCCAGA | TGTTAAGCAA |
| 121 | TTTTTGGAAG | CGCATCGAGC | TGAATTAACG | AATGCTATGA | TTGATGAAGA | CTTAAATGTG |
| 181 | TTACAAGAGT | ATAAAGATCA | ACAAAAACAT | TATGACGGTC | ATAAATTTGC | TGATTGTCCA |
| 241 | AATTTCGTAA | AGGGCATGT | GCCTGAGTTA | TATGTTGATA | ATAACCGAAT | TAAAATACGC |
| 301 | TATTACAAT | GCCCATGTAA | GCTCAAGTAC | GACGAAGAAC | GCTTTGAAGC | TGAGCTAATT |
| 361 | ACATCTCATC | ATATGCAACG | AGATACTTTA | AATGCCAAAT | TGAAAGATAT | TTATATGAAT |
| 421 | CATCGAGACC | GTCTTGATGT | AGCTATGGCA | GCAGATGATA | TTTGTACAGC | AATAACTAAT |
| 481 | GGGAACAAG | TGAAAGGCCT | TTACCTTTAT | GGTCCATTTG | GAACAGGTAA | ATCTTTATT |
| 541 | CTAGTGCAA | TTGCGAATCA | GCTCAAATCT | AAGAAGGTAC | GTTCGACAAT | TATTATTTA |
| 601 | CCGGAATTA | TTAGAACATT | AAAAGGTGGC | CATTTTAATG | CTTGATGATA | AAAGAAATTA |
| 661 | CATCGCGTAA | GAGAAGCAAA | AATTGGACCT | TTGCTACATT | AGTGAATTGG | AGAAGTGACT |
| 721 | CCATGGGTGA | GAGATGAGT | TTTTGACTAT | AGTGAATTGG | TCATGAATGT | TCATGAATTA |
| 781 | CCAACATTCT | TTAGTTCTAA | TTTTGACTAT | AGTGAATTGG | AACATCATTT | AGCGATGACT |
| 841 | CGTGATGGTG | AAGAGAAGAC | TAAAGCAGCA | CGTATTATTG | AACGTGTCAA | ATCTTTGTCA |
| 901 | ACACCATACT | TTTTATCAGG | AGAAAATTTC | AGAAACAATT | GA | |

SEQ ID NO:2

| | | | | | |
|---|---|---|---|---|---|
| 1 | MGGGQSIMKQ | FKSIINTSQD | FEKRIEKIKK | EVINDPDVKQ | FLEAHRAELT | NAMIDEDLNV |
| 61 | LQEYKDQQKH | YDGHKFADCP | NFVKGHVPEL | YVDNNRIKIR | YLQCPCKIKY | DEERFEAELI |
| 121 | TSHHMQRDTL | NAKLKDIYMN | HRDRLDVAMA | ADDICTAITN | GEQVKGLYLY | GPFGTGKSFI |
| 181 | LGAIANQLKS | KKVRSTIIYL | PEFIRTLKGG | FKDGSFEKKL | HRVREANILM | LDDIGAEEVT |
| 241 | PWRDEVIGP | LLHYRMVHEL | PTFFSSNFDY | SELEHHLAMT | RDGEEKTKAA | RIIERVKSLS |
| 301 | TPYFLSGENF | RNN | | | | |

SEQ ID NO : 3
Complete genome sequence of bacteriophage 77

```
   1 gatcaaaata cttggggaac ggttagggag taaacttcgc gataatttta aaaattcatg
  61 tataocccc ctcttataac cattttaagg cagtgatga aatggagatt atagtcgatg
 121 aaaatttagt gcttaaagaa aaagaaaggc tacaagtatt atataaagac ataoctagca
 181 ataaattaaa agtagttgat ggtttaatta ttcaagcagc aaggctacgt gtaatgcttg
 241 attacatgtg ggaagacata aaagaaaaag gtgattatga tttatttact caatctgaaa
 301 agcgccacc atatgaaagg gaaagaccag tagccaaact atttaatgct agagatgctg
 361 catatcaaaa aataatcaaa caattatcgg attttattgc cgaagagaaa gaagacacag
 421 aaacgccatc tgatgattac ctatgattag taataaatac gttgatgaat atataaattt
 481 gtggaaacaa ggaaagataa ttttaaataa agaaagaaatt gatctcttta attatctaca
 541 aaacatata tattcacgag atgatgtata ttttgatgaa cagaaaatcg aggattgtat
 601 caaatttatt gaaaaatggt attttccaac attaccattt caaagttta tcatagctaa
 661 tatatttctt atagataaaa atacagatga agctttcttt acagaatttg ctatttcat
 721 gggacgtgga ggcggggaaa acggtctaat aagtgctatt agtgatttc tttctacgcc
 781 cttacagga gttaaagaat atcacatctc cattgttgct aatagtgaag atcaagcaaa
 841 aacatcgttt gatgaaatca gaaccgtttt aatgataaac aaacgaaata agacgggtaa
 901 aacgccaaaa gctccttatg aagttagtaa agcaaaaata ataaaccgtg caactaaatc
 961 ggttattcga tataacacat caaacacaaa ggtggacgtg aggggtgtgt
1021 tattttttgat gaaattcatt atttctttgg tcctgaaatg gtaaacgtca aacgtggtgg
1081 attaggtaaa aagaaaaata gaagaacgtt ttatataagt actgatggtt ttgttagaga
1141 ggttatatc gatgcaatga agcacaaaat tgcaagtgta ttaagtggca aggttaaaaa
1201 tagtagattg tttgctttt attgtaagtt agacgatcca aaagaagttg atgacagaca
1261 gacgtgggaa aagcgaaac caatgttaca taaccgttta tttaccattc aacgttcaa ctaaaacact
1321 gctaagcacg attgaagaag aatataacga tttaccattc aacgttcaa ataagcccga
1381 attcatgact aagcgaatga atttgcctga agttgacctt gaaaaagtaa tagcaccatg
1441 gaaagaaata ctagcgacta atagagagat accaaatttg gataatcaaa tgtgtattgg
1501 tggtttagac tttgcaaaca ttcgagattt tgcaagtgta gggctatat tccgaaaaaa
1561 cgatgattac atttggttag gacattcgtt tgtaagacaa gggttttttgg atgatgtcaa
1621 attagaacct cctattaaag aatgggatta aatgggatta ttgaccattg tcgatgatga
1681 tgtcattgaa attgaatata tagttgattg gttttttaaag gctagagaaa aatatgggct
```

FIG. 2B

```
1741 tgaaaaagtc atagctgata attatagaac tgatatttgta agacgtgcgt ttgaggatgc
1801 tggcataaaa cttgaagtac ttagaaatcc aaaagcaata catggattac ttgcaccacg
1861 tatcgataca atgttgcga aacataacgt aatatatgga gacaatcctt tgatgcgttg
1921 gtttactaat aatgttgctg taaaatcaa gccggatgga aataaagagt atatcaaaaa
1981 agatgaagtc agacgtaaaa catggcttt catggcttt gttcacgcat tatatagagc
2041 agacgatata gtagacaaag acatgtctaa agcggcttgat gcattaatga gtatagattt
2101 ctaatagagg aggtgagaca tgagtattct agaaaagata tttaaaacta ggaaagatat
2161 aacatatatg cttgatttag atatgataga agatctatca caacaagcgt atgtgaaacg
2221 tttagcgatt gatagttgta ttgaatttgt tgcgcgagct gtcgctcaaa gtcattttaa
2281 agtattggaa ggtaatagaa ttcaaaagaa tgatgtttac tacaagttaa atataaaacc
2341 aaatactgac ttatcaagcg atagttttg gcaacaagtt atatataaac taattttatga
2401 taacgaggtt taatcgtag taagtgacag cttatcgcag atagcttta
2461 cagagaagag atgatgatat atgatgataa gtaacggtta aagattatac
2521 ttatcaacgt acgcttttgt catatattta aagtacaaca acaataaagt
2581 gacacactt gtagaaagtc tgcaagaggt ttacggggaaa aagtacgaa gaatgatagg
2641 tgcacaatta aaaaactatc tattcgaaga atattcgaa tctgcctcta gcgcatatga
2701 cgaaagaat atagaaaaat aaatagaggg gatttttgaa cacaaataaa ttattcaata cttttaataa
2761 aaatcaacta gcaatcgcgc ctttgataga aggtttgat tatgaggaat atgcaataaa
2821 tggtaagaat gtaacatgc cttttctga attgagtgag ctaatgagag tacggagaaa cagctgattt
2881 aaatgttgcg ttgatgattg gtataccctcc agttcttgatt tacggagaaa cccttattaa
2941 ggaaaaaaac acgcttgtat ttgagaagtt ctgtttaaca ttgaaagata caagaataga
3001 gaacgaatta aacgcgaaac tcataacaca aagcatgtct gaagcaattg acaaacttgt
3061 aattgtcggt gtgaataaaa aagaccact tcaatatgct gcgggattatg aaccatcaga
3121 aagttctgt tcattacaa ggaatgaggt gcgatgaagt ttaggtgaag acagtggtga
3181 caatcctgaa ttagacgaat acctgattac taaaactac gaaaaagcta atgaaagcgg
3241 aaatgatgaa aaagaaaaag atgaaaacac tttgaaaggt ggtgatgaag cttggtatgg
3301 agattaaagg cgtcatcgtt tccaacgaag ataaatgggt ttacgaaatg gatgatata acacattta
3361 attcgactg tcctaaagat gttttaacag aactagaatt tagtaggtag tgaaatgaa gcgcatcgc
3421 ttataattaa ctcaaatggt ggtaaccag tagctgtcgta tcacagcaat agcagcaagt atgattcaca
3481 gagctcataa aggcaaagtg gctggttgac cacatcgaaa tgagtccggt tgctagaatg gaaacattag
3541 ttatcgcaat ggctggtgac tattgcgcaa ggagaagtgc aagatctaaa atgcggttag agctgggtaaa
3601 atccttcaag tattgcggca tgagaaggcat atgcgagcat atcatgcagt ggctgagttag agctggtagg aacaaacaag
3661 aacatgttgg tcaaataatg ctgggtcat atgcaggcat gatgagctag agctggtatag aacaaacaag
3721 aacttataga aatgatggct aaggaaacgt aggaaaacgt
```

FIG. 2C

```
3781 gttttgcgga tagtaaaatg tttgaaaacg aattgtagca acaatatgca agcgatacac
3841 aagtgttatc gaaagatgta ttaaatcgtg ttaacagcttt taacagcttt agcccagagg
3901 ttaacattga tattgacgca atagcaaata aagtaattga atagcaaatc atgaaagaaa
3961 aggaatcaga aatcgatgtt gcagatagta aattatcagc aaatggattt tcaagattcc
4021 tttttaata caaaaatagg aggtcataaa atgactataa atttatcgga aacattcgca
4081 aatgcgaaaa acgaatttat taatgcagta aacaacggtg aaccgcaaga aagacaaaat
4141 gaattgtacg gtgacatgat taaccaacta tttgaagaaa ctaaattaca agcaaaagca
4201 gaagctgaaa gagtttctag tttacctaaa tcagcacaaa ctttgagtgc aaaccaaaga
4261 aatttcttta tggatatcaa taagagtgtt ggatatataa aagaaaaact tttaccagaa
4321 gaaacaattg atagaatctt cgaagattta acaacgaatc atccattatt agctgactta
4381 ggtattaaaa atgctggttt gcgttatgaa ttcttaaaat ccgaaacttc tggcgtggct
4441 gtttggggta aaatctatgg tgaaattaaa ggtcaattag atgctgcgtt cagtgaagaa
4501 acagcaattc aaaataaat gacagcgttt gttgttttac caaagatttt aaatgatttt
4561 ggtcctgcgt ggattgaaag atttgttcgt gttcaaatcg aagaagcatt tgcagtggcg
4621 cttgaaactg cgttcttaaa aggtactggt aaagaccaac gcattccag aaaccgtcaa
4681 gtacaaaaag gtgtatcggt aactgatggt gcttatccag agaagaaga acaaggtacg
4741 cttacatttg ctaatccgcg ctaaggtaa aattgaattga cgcaagtgtt taaataccac
4801 tcaactaacg agaaaggtaa atcagtacg gttaaaggta atgtaacaat ggttgttaat
4861 ccgtccgatg cttttgaggt tcaagcacag tatacacatt taatgcaaa tggcgtatat
4921 gttactgctt taccatttaa ttttgaatgt attgagtcta cagttcaaga agcaggtaag
4981 gttttaacgt acgttaaagg tctatatgat gttagatgat ggttatttag ctggtggtat taatgttcag
5041 aaattaaag aaacacttgc gttagatgat atgaagttgct gctgttttgga acactgcaaa acaattgct
5101 tacggcaaag cgaaagatac tagaagatac ctataaaatt ttatgaggtg aattagatt aaaaggacat
5161 aaccagctt tagaagatgac aatttaaaaa catagagcac atcaacaca agtacaaagt ataaaatggt
5221 gaaattaaa gttgttagag aagggtataa caatcctcgt gttgaattgt tgacaaatca
5281 aggggagttg tatccagctg aaggggtataa aagtttatat cgtacctttta gataagctga caaacaaga
5341 aatcaaaaat aagtacgaca cattacaaaa aaagcgtct agttcaatgg ttaaaagtga
5401 attattagaa ctatcgaat gtgaagacaa tgacgattga cttaaagcag ttgatttaaaaa
5461 aatcatcgac ttattgaatg cataattcag aggatgagta cttaaagaat ttaataggtc
5521 aatcacttga aagattgac aatcagtgcg gagttttga attagagaat cacttcaacg
5581 tgtcgtacga gcgtataaaa aatcagtgcg gagttttga cttatcaaga tttattagaa cacttcaacg
5641 aagaattgat actacacgc gctaataag cttatctct aatggaggta tcagaagatg
5701 acaattacag accgaaata atagatttt cgttatctct aatggaggta tcagaagatg
5761 aagaaagtgt ttaagaaacc tagaattaca actaaacgtt actaaacgtt tgttcatttt
```

FIG. 2D

```
5821 tataagtata ctgaaaataa tggtccagaa gctggagaaa aagaagaaaa attattatat
5881 agctgttggg cgagtattga tggtgtctgg ttacgtgatt tacgtgaat tatcaaac
5941 ggaacgcaaa atgacattaa attgtatatt cgtgatcgc aaggtgatta tttaccagt
6001 gaagaacatt atctttgaaat tgaatcaaga tatttcaaa atcgttttgaa tataaagcaa
6061 gtatcaccag atttggataa taaagactt gctggaggata tagttcatga
6121 gtgtgaaagt gacaggtgat aaagcattag agaaaaacat tttggcataa
6181 aagagatggt aaaagttcaa ataaggcgt taatagctgg tgctaaggta attgttgaag
6241 aaataaaaaa acaactcaaa ccttcagaag gatcaggagc actgattagt gagattggtc
6301 gtactgaacc tgaatggata aagggaaaac gtactgttac aattaggtgg cgtgggcctt
6361 ttgaacgatt tagaatagta catttaattg aaaatggtca tgttgagaaa aagtcaggaa
6421 aatttgtaaa acctaaagct atgggtggga ttaatagagc aataagacaa gggcaaaata
6481 agtattttga gacgctaaaa atggagttga acagaatatt attgatattt tgtacaaagt
6541 tcatgaagtg attagtcaag acagaattat taaagatac gtaaatatca ataatattaa
6601 gttcaataaa tacctaatg cttatactga tgatgtacct tttattgtta ttgacgatat
6661 cgacgaccca atactacaa cttatactga cggagatgag tgtgcatata gttatattgt
6721 ccaaatagat gttttgtta agtacaatga tgaatatataat gcgagaatca taagaaataa
6781 gatatcttat cgcattcaat agttattatg gtctgaacta aacatataga aaaatgggaa atgtttcaaa
6841 tggaaaccg gaatatatag aagaatttaa attaaatggc agctctcgcg tttacgaggg
6901 cattttttat aagagagaa actggttttag gttttcgctaa gcaagtgcgc caaggcgta
6961 tattaacatt acaaaaaaca gaggattaca aaaaattggt gaagcgcgg aattaaaata
7021 tagtgatatt acaaaacaa tatgctgatg gcggtccaat agagattggt gtggagaact
7081 aaaaacagct caaatgcatg cgttccctaa agagattcgc aaaattgttt gagaaggtaa
7141 aatctcatta caaatgcgtt acgaagagaa acaaggtaaa caaaacaatt acgtagctgt
7201 ttatgatgaa gatggcgttt aagacggtac aagagaaca gttttattac ctaaagttat
7261 atggttcaga caagagcgta aagagcgtac atggagaaac ggctgagaaa gattgggatt tctcaagtga
7321 gtttacaaat cctaaaatcg atggagaaac ggctgagaaa gattgggatt tctcaagtga
7381 agaggttgaa ggtgaggcac tttttccctt agtttgataat aaaaagtcag gcgaagaggc
7441 tatcttttgat tcagctaaca tgacaaatca tgatggagac gtgacagagg gtaacgaaga
7501 tttcttaaag aaaattttag gcgaagaata tactggaaa actgcggttaa tataccagat
7561 aacttgtaaa cacttaagaa ctcatcggaa actcggttaa agtcggttaa atgtttgtagt agagccatct
7621 agcattaaaa agttattgaa tggcgacaca tacgatttta atgtttgtagt atcaatagt
7681 aatcaaagta agtcaggta gttactgcgga ttactgcggaa gcaggc attgctacgg agttggtaat
7741 gatggtcaag ttactgcgga attgctacgg agcacaaggc attgctacgg agttggtaat
7801 atgagtgaca ctataacaat aaatgtagaa gcataagagg gggcaaccc tctattttat
```

FIG. 2E

```
7861 ttgaaaataa ggagagtatt ataaaatggc aaaattaaaa cgtaacatta ttcaattagt
7921 agaagatcca aaagcaaatg aaattaaaat acaaacgtac ttaacaccac acttcattc
7981 atttgaaatt gtatacgaag caatggattt aatcgatgat attgaggacg aaaatagcac
8041 gatgaagcca agagaaaatcg ctgacagatt gatggatatg gttgtaaaaa tttacgataa
8101 ccaattcaca gttaaagacc taaaagaact tatgcatgca cctgatggaa tgaatgcact
8161 tcgtgaacaa gtgatttttca ttactcaagg tcaacaaact gaggaaacta gaaattttat
8221 ccagaacatg aaataaagcc tgaagattta acatataaag caatgtttgaa aaatatggat
8281 actctcatga tggacttaat tgaaaatggt aaagacgcta acgaagtttt aaaaatgcca
8341 tttcattatg tgctttccat atatcaaaat acattctga agaaaaagca
8401 gaggctttaa ttgatgcatt ttaactttaa ccgtttggtt agggtttatt ttttgaactt
8461 ttttagaaag gaggtaaaaa atgggagaaa gaataaaagg tttatctata ggtttggatt
8521 tagatgcagc aaatttaaat agatcattg cagaaatcaa acgaaacttt aaaacttaa
8581 attctgactt aaaattaaca ggcaacaact cagaaaatac actgatagtt
8641 acaaacaaag gattaaagaa cttgatggaa ctatcacagg ttataagaaa aacgttgatg
8701 attagccaa gcaatatgac aagtatctc aagaacagt gcagaagctc
8761 aaaagttaac acaagaatat aacaaacaag caaatgagct gaatattta gaaagagaat
8821 tacaaaaaac atcagccgaa tttgaagagt tcaaaaaagc tcaagttgaa gctcaaataa
8881 tggcagaaag tggctgggga aaaccagta aagtatggga cctaaattaa
8941 caaaaatggg tgatggttta aatggtttta gtaaagtttt gatcttttgc gtaactgcac
9001 ctgttttagg tattgcagca gcatcaggaa aagcttttgc agaagttgat aaaggttag
9061 atactgtttac caagcaaaca ggcgcaacag gctgcaatg aaaaaaattg cagaactcat
9121 ttaaagatgt ttatgccaat atgctgaaac atgctgaaat gttttggtgg gtttaggag
9181 aagttaatac aaggttaggt tcatataaca aagaacttga gtgtcaaagc gagtcattct
9241 tgaaattcag tcatataaca ggttctgacg gtgtgcaagc cgtacagtta attaccgtg
9301 caatgggcga tgcaggtatc gcaggcaagtg aatacataaag tgttttggat atggtagcaa
9361 aagcgccgca agctagtggg ataagtgttg atacattagc atgaaagaaa actaaatag
9421 gcgctccaat gagagctatg ggctttgaga tgaaaaaaat cattcagtgg tttaaaaaaa gctatacgg
9481 gggaaagtc agctcattg actcagaag aagaatttaa aagaacatta gcagaaattg
9541 attggtaa agctggaaa gttagcaga tgaagcatt ggtgcaaagg
9601 aaagacgcc gatataagct ggtatcggat gtttagcgat tagttacaa aatttttaa
9661 caggtcctga tttagcagac accaaaaaag gttggtgct tagttatcaa gaattttcaa
9721 aaactattga agattctgt agtacagtaa accaaacatt taaagattct gaaagtggct
9781 ccgaagatt taaagtagca atgaataaat aaaattagt aggtgctgat gtatggcttt
9841 ctattgaaag tgcgtttgct cccgtaatgg aagaattaat caaaagcta tctatagcgg
```

FIG. 2F

```
 9901  ttgattggtt  agtgatggtt  ctaaaagatc  aattgttatt  ttcagtggta
 9961  ttgctgctgc  aattggtcct  gtagttttg   ggttaggtgc  atttataagt  acaattggca
10021  atgcagtaac  tgtattagct  ccattgttag  ctagtattgc  aaaggctggt  ggattgatta
10081  gttttttatc  gactaaagta  gaacttgtct  cacagcttta  actggtccaa
10141  ttggcattgt  attagtgta   ttggctggtt  tagcagtcgc  atttacaatt  gcttataaga
10201  aatctgaaac  atttagaaat  tttgttaatg  gtgcaattga  aagtgttaaa  caaacattta
10261  gtaattttat  tcaattttat  caaccttcg   ttgattctgt  taaaacatc   tttaaacaag
10321  cgatatcagc  aatagttgat  ttcgcaaaag  atattggag   tcaaatcaat  ggattcttta
10381  atgaaaacgg  aatttccatt  gttcaagcac  ttcaaaatat  atgcaactt   attaaagcga
10441  tatttgaatt  tattttaaat  accaattac   gttcgcgatt  tggcaagtga
10501  tgcaatttat  ttggccggcg  gttgctaaaa  tgattgtcag  tacttggag   aacataaaag
10561  gtgtaataca  aggtgcttta  tttatcagca  ttggcttgat  taagttcttc  tcaagtttat
10621  tcgttggtga  ttggcgagga  gttttggacg  cgttgtaggtaa  gattcttaaa  ggagcagttc
10681  aattaatttg  gaatttagtt  caattatggt  ttgtagggtaa  aatacttggt  gttgttaggt
10741  actttggcgg  gttgctaaaa  ggaaatttg   cagggaaaattg  ggacgtaata  agaagtatat
10801  tcagtaaatc  tttatcagca  atttgcacg   caacaaaaag  tattttga    ttttattta
10861  atagcgtaaa  atcaattttc  acaatatga   aaaatttg   atctaatact  tggagcagta
10921  tccgtacgaa  tacaatagga  aaagcgcagt  aaagaaattt  tggcgtcaaa  tcaaaatta
10981  ctaatttatg  gaatgcgacg  aaagaaattt  cattatttt   aagaaaattgg  atgtcaaata
11041  tttggaattc  cattaaagat  aatacggtag  gaatttgcaag  agtaaggtag  attaaagtc
11101  gtggaatttt  cacaaatatg  cgcgataagc  tgagttccat  ccgttttccat  gacggttaa
11161  atatcggcgg  tatgtaagc   gctattaaaa  aaggaacttaa  tataataatc  gacggttaa
11221  actgggtcgg  tggtaagttg  ggaatggata  aatacctaa   gttacacact  ggtacagagc
11281  acacacatac  tactacaaga  ttagttaaga  acggtaagat  tgcacgtgac  acattcgta
11341  cagttgggga  taaggacgac  ggaaatggtc  caaatggttt  tagaaatgaa  atgattgaat
11401  tccctaacgg  taaacgtgta  atcacaccta  atacagatac  taccgcttat  ttacctaaag
11461  gctcaaaagt  atacaacggt  gcacaaact   attcaatgtt  aaacggaacg  cttccaagat
11521  ttagtttag   tactatgtgg  aaagatatta  aatctggtgc  atcatcggca  ttaactgga
11581  caaagataa   aatatccaaat  ggtaccaaat  gcttggcga   taaagttgc   acattcgta  gatgttttag
11641  atttatgga   aaactttaa   attatatact  tgaagctttt  tgaagctttt  ggaattgatt
11701  tcaatttttt  aactaaaggt  atggaaattg  atggaataa   acaaaagct   gcatggtcta
11761  agattaagaa  aagtgctact  caggcgacat  gattggataa  aagaaattt   gcggtggcg
11821  atttagtcgg  cggaatatta  gaccctgaca  aaattaatta  tcattatgga  cgtaccgcag
11881  cttataccgc  tgcaactgga  agaccattc   atgaaggtgt  cgattttcca  tttgtatatc
```

```
11941  aagaagttag  aacgccgatg  ggtggcagac  ttacaagaat  gccatttatg  tctggtggtt
12001  atggtaatta  tgtaaaaatt  actagtggcg  ttatcgatat  gctatttgcg  catttgaaaa
12061  actttagcaa  atcaccacct  agtggcacga  tggtaaagcc  cggtgatgtt  gttggtttaa
12121  ctgtaatac   cggatttagt  acaggaccac  attttacattt tgaaatgagg  agaaatggac
12181  gacatttga   ccctgaacca  tattaagga   atgctaagaa  aaaaggaaga  ttatcaatag
12241  gtggtggcgg  tgctacttct  ggaagtggcg  caacttatgc  cagtcgagta  atccgacaag
12301  cgcaaagtat  tttaggtggt  cgttataaag  gtaaatggat  tcatgaccaa  atgatgcgg
12361  ttgcaaaacg  tgaaagtaac  taccagtcaa  atgcagtgaa  taactgggat  ataaatgctc
12421  aaagaggaga  cccatcaaga  ggattattcc  aaatcatcgg  ctcaactttt  agagcaaacg
12481  ctaaacgtgg  atatactaac  tttaataatc  cagtacatca  aggtatctca  gcaatgcagt
12541  acattgttag  acgatatggt  tgggtggtt   ttaaacgtgc  tggtgattac  gcatatgcta
12601  caggtggaaa  agttttgat   ggttggtata  acttaggtga  agacggtcat  ccagaatgga
12661  ttattcaac   agatccagct  cgtagaaaatg atgcaatgaa  gattttgcat  tatgcagcag
12721  cagaagtaag  aggggaaaaa  gcgagtaaaa  tagcaattcc  tagccaatta  tcagacttaa
12781  acgggtttga  tgatcctagc  ttattattga  acaacagcaa  caacaaatag
12841  ctttattact  gaaaatagca  caatctaacg  atgtgattac  agataaaagat  tatcagccga
12901  ttattgacga  atacgcttt   gataaaaaag  tgaacgcgtc  cgagaaaggc
12961  aagaatcaac  aaaagtaaag  tttcttggtt  gaggaattgc  tattcaatga  tagacactat
13021  taaagtgaac  aacaaaacaa  ttccttggtt  gtatgtcgaa  agaggggttg  aaatacctc
13081  ttttaattat  gttttaaaaa  cagaaaatgt  agatggacgt  tcggggtcta  tatataaagg
13141  gcgtaggctt  gaatcttata  gttttgatat  acttggtg    gtacgtaatg  actatttatc
13201  tcacaacggc  attaaaacac  atgatgacgt  cttgaatgaa  ttagtaaagt  tttttaacta
13261  cgaggaacaa  gttaaattac  aatcaaatc   taaagattgg  tactggaacg  cttatttcga
13321  aggaccaata  aagctgcaca  aagaatttac  aatacctgtt  aagttcacta  tcaaagtagt
13381  actaacagac  ccttacaaat  attcagtaac  aggaaataaa  aatactgcga  tttcagacca
13441  agtttcagtt  gtaaatagtg  ggactgctga  cactccttta  attgttgaag  cccgagcaat
13501  taaccatct   agttactta   tgattactaa  aaatgatgaa  gattatttta  tggtttgtga
13561  tgatgaggta  accaaagaag  ttaaggatta  catgcctcct  gtttatcata  gtgagtttcg
13621  tgatttcaa   ggttgggacta agatgattac  tgaagatatt  ccaagtaatg  acttaggtgg
13681  taagtcggc   ggtgactttg  tgatatccaa  tcttggcgaa  ggatataaag  caactaattt
13741  tcctgatgca  aaaggttggg  ttggtgctgg  cacgaaacga  gggctccta   aagcgatgac
13801  agatttcaa   attacctata  aatgtattgt  tgaacaaaaa  ggtaaaggtg  cggaagaac
13861  agcacaacat  atttatgata  gtgatggtaa  gttacttgct  tctattggtt  atgaaaataa
13921  atatcatgat  agaaaaatag  gacatattgt  tgttacgttg  tataaccaaa  aaggagaccc
```

```
13981  caaaagata  tacgactatc  agaataaacc  gataatgtat  aacttggaca  gaatcgttgt
14041  ttatatgcgg  ctcagaagag  taggtaataa  attttctatt  aaaacttgga  aatttgatca
14101  cattaaagac  ccagatagac  gtaaacctat  tgatatggat  gagaaagagt  ggatagatgg
14161  cggtaagttt  tatcagcgtc  cagcttctat  catagctgtc  tatagtgcga  agtataacgg
14221  ttataagtgg  atggagatga  atgggtagg  ttcattcaat  acggagattc  taccgaaacc
14281  gaaggcgca  agggatgtca  ttatacaaaa  aggtgatta  gtaaaaatag  atatgcaagc
14341  aaaaagtgtt  gtcatcaatg  aggaaccaat  gttgagcgag  aaatcgtttg  gaagtaatta
14401  tttcaatgtt  gattctgggt  acagtgaatt  aatcatacaa  cctgaaaacg  tctttgatac
14461  gacggttaaa  tggcaagata  gatatttata  gaaagagat  gagagtgtga  tacatgtttt
14521  agatttaac  gacaagatta  tagatttcct  ttctactgat  gaccctct  tagttagagc
14581  gattcataaa  cgtaatgtta  atgacaattc  agaaatgctt  gaactgctca  tatcatcaga
14641  aagagctgaa  aagttccgtg  aacgacatcg  tgttattata  agggattcaa  acaaacaatg
14701  gcgtgaattt  attattaact  gggttcaaga  tacgatggac  ggctacacag  agatagaatg
14761  tatagcgtct  tatcttgctg  atataacaac  agctaaaccg  tatgcaccag  gcaaatttga
14821  gaaaaagaca  acttcagaag  cattgaaaga  tgtgttgagc  gatacaggtt  gggaagtttc
14881  tgaacaaacc  gaatacgatg  gcttacgtac  tacgtcatgg  acttcttatc  aaactagata
14941  tgaagttta  aagcaattat  gtacaaccta  taaaatggtt  ttagatttt  atattgagct
15001  tagctctaat  accgtcaaag  gtagatatgt  agtactcaaa  aagaaaaaca  gcttattcaa
15061  aggtaaagaa  attgaatatg  gtaaagattt  agtcgggtta  actaggaaga  ttgatatgtc
15121  agaaatcaaa  acagcattaa  ttgctgtggg  gacaaaggga  agcgtttaga
15181  gctagttgtg  acagatgacg  aagcgcaaag  acctgaaaat  ctacctatgc  gctatatttg
15241  ggggatatat  gaaccacaat  cagatgatca  tcaattcaac  gaaacacgat  taagttcttt
15301  agccaaaaca  gagttaaata  aacgtaagtc  ggcagttatg  tcatatgaga  ttacttctac
15361  tgatttggaa  gttacgtatc  cgcacgagat  tatatcaatt  ggcgatacag  tcagagtaaa
15421  acatacacc  cctgatgttg  ctgtcttgcg  cattgtatgt  agaggcagaa  gttattgctg  aagaatataa
15481  cataatttca  gaaaatagca  catatacat  agcgattgaa  cggtcaacct  caaaagttaa  acgataatat
15541  attacgagaa  gagtttaaca  ttaaagatgt  tgtagatggt  gaattaggt  gaattagaat  acgatttgaacg
15601  tagcaatatc  aacactatag  ttaaagatgt  tgtagatggt  gaattggt    gaattagaat  actttgaacg
15661  caaaatatac  aaaagtgata  caccgccaga  aaatccagtc  aatgatatgc  tttggtatga
15721  tacaagtaac  cctgatgttg  ctgtcttgcg  tagatattgg  aatggtcgat  aatggtgaagc  ggattgaagc
15781  aacaccaaat  gatgttgaaa  aattaggtgg  tataacaaga  gagaaagcgc  tattcagtga
15841  attaaacaat  attttatta   atttatctat  acaacacgct  agtcttttgt  cagaagctac
15901  agaattactg  aatagcgagt  acttagtaga  taatgattg   aaagcggact  tacaagcaag
15961  tttagacgct  gtgattgatg  tttataatca  aattaaaat   aattagaat   ctatgacacc
```

| | | | | |
|---|---|---|---|---|
| 16021 | cgaaactgca | acgattggtc | ggttggtaga | tacacaagct | ttattcttg | agtatagaaa |
| 16081 | gaaattacaa | gatgttttata | cagatgtaga | agatgtcaaa | atcgccattt | cagatagatt |
| 16141 | taaattatta | cagtcacaat | acactgatga | aaaatataaa | atcgcgttgg | aaaataatagc |
| 16201 | aacaaaattt | ggtttaacgg | tgaatgaaga | tttgcagtta | gtcggagaac | ctaatgttgt |
| 16261 | taaatcagct | attgaagcag | ctagaaacag | cacattacgtg | cgtttagata | actatgttaa |
| 16321 | aacatcggac | tataaaacag | acaagacgg | tattgttgaa | cgtttagata | ctgctgaagc |
| 16381 | tgagagaacg | actttaaaag | gtgaaatcaa | agataaagtt | acgttaaacg | aatatcgaaa |
| 16441 | cggattggaa | gaacaaaaac | aatatactga | tgaccagtta | agtgatttgt | ccaataatcc |
| 16501 | tgagattaaa | gcaagtattg | aacaagcaaa | tcaagaagct | caagaagctt | taaaatcata |
| 16561 | cattgatgct | caagatgatc | ttaaagagaa | ctatacaaga | gcgtatgctg | atggtaaaat |
| 16621 | ttcggaagaa | gagcaacgcg | ctataaagaa | tgctcaagct | aaactttgaag | aggcaaaaca |
| 16681 | aaacgcagaa | ctaaaagcta | gaaacgtcga | aagaaaagct | aatgcttata | cagacaacaa |
| 16741 | ggtcaaagaa | agcacagatg | cacgagggaa | aacattgact | cgctatggtt | ctcaaattat |
| 16801 | acaaaatggt | aaggaaatca | aattaagaac | tactaaagaa | gagtttaatg | caaccaatcg |
| 16861 | tacactttca | aatatattaa | acgagattgt | tcaaaatgtt | acagatggaa | caacaatcag |
| 16921 | atatgatgat | aacgagtgg | ctcaagcttt | gaatgtgggg | ccacgtggta | ttagattaaa |
| 16981 | tgctgataaa | attgatatta | acggtaatag | acggtaatag | agaaataaac | cttcttatcc | aaaatatgcg |
| 17041 | agataaagta | gataaaaacc | atattgtcaa | cagtcttaat | ttatcaagag | agggtcttga |
| 17101 | tatcaatgtt | aatagaattg | gaattaaagg | gaattaaagg | cggtgacaat | aacagatatg | ttcaaataca |
| 17161 | gaattgattct | attgaactag | gtggtatttgt | tgaaagacgg | gcaacgtact | tggaagaggga | aacgttcaac |
| 17221 | agacgatatt | tttacgcgac | tatatgttct | tcacctaaga | gttagaaata | acaccgctgg |
| 17281 | cggttcactt | tctggtacga | atttggtttat | ttcgacttat | attgatggtg | aaggtgaaga |
| 17341 | cggtggttca | atcaattcct | ttcggttacga | ggataaaact | tacagtcaga | gtggcatgaa |
| 17401 | tggtataaca | tcttacgctt | atgtggtgt | cgttgcacta | acgtcagata | ataatcggt |
| 17461 | tgttctggag | catcgaatat | catcgaatat | caaaagcaaa | caggcaccgg | tgtatttata |
| 17521 | tccaaacaca | gacaaagtgc | ctggattaaa | ccgatttgca | ttcacgctgt | ctaatgcaga |
| 17581 | taatgcttat | tcgagtgacg | gttatatatt | gtttatattat | gatgagaact | atgattacgg |
| 17641 | tgcgggtatc | aggttttcta | aagaaagaaa | taaaggttctt | gttcaaattt | ttaatggacg |
| 17701 | atatgcaaca | ggtggagata | caacaatcga | agcaggtat | ggcaattta | atatgctgaa |
| 17761 | acgacgtgat | tcttacgctt | atatcatat | acagagtaca | gacctactgt | ctgtaggttc |
| 17821 | agatgatgca | ggagatagga | tagcttctaa | ctcaatttat | agacgtactt | attcggccgc |
| 17881 | agctaattig | catattactt | ctgctggcac | aattgggcgt | tcgacatcag | cgcgtaaata |
| 17941 | caagttatct | atcgaaaatc | aatataacga | tagagatgaa | caactggaac | attcaaaagc |
| 18001 | tattcttaac | ttacctatta | gaacgtggtt | tgataaagct | gagtctgaaa | ttttagctag |

```
22141  gaatataaac  cctctatcaa  catagcttgg  ttccattgt   tgcatctttt  tatttctaa
22201  cattattttt  ttcaatacat  ttgctatcct  tgaattgatg  gcgattttc   ttcttgaacc
22261  tgcggtctta  gtagtatctt  tgtgaccaaa  tccagcatta  catttgattc  tgtgaatagt
22321  gccattaata  gcgatcgttt  tattttgag   gtcaacatct  ttaacttgga  gagctaataa
22381  ctcacctatg  cgcataccctg ttaagcttg   aacttctaca  gcccagcaa   ctaaaatacg
22441  agctctatac  tgcatgttat  tatcgttcag  tataaaatcg  cgtatctgta  ttacctgttc
22501  catctctaaa  tagttataca  tttcgcttc   ttctttttct  atatcttcta  tcgtcttact
22561  cttctttggt  agtgtgacgc  tatttaatat  gtgttcgttt  ggataattgt  aaaatttaac
22621  gggcgtattta atagcttctt  tcatatgtcc  aagttgacgc  tttacctgat  ttgcagaata
22681  tacgtttgat  aatttgttaa  taaatgtttg  catgtactt   gtatcaattt  tgtttaaaag
22741  taaatttga   gaactgttct  ttttgatgtt  tttgattctt  tttttcaaat  tatcaagcgt
22801  cgttacttta  aagccagatg  tttttatatg  atattcaagc  gtttttcaaat catcatcta  ataacgcgtg
22861  aaaagtcaaa  gtttttaatt  cgcttgacga  ctgttgtttt  agttttttctt ttatttttc
22921  ttctaaacga  aacattgcct  cttttttgcga tttcttattca agacaacact
22981  tacacgtttc  catttatctg  tatacggatc  tttgtattc   tcgtagtatc  tatcttcgt
23041  ttcattgttc  ttattttta   attttttcaaa ccacatttta  catccctcct  caaaattggc
23101  aaaaataat   aagggtaggc  gggctaccca  tgaaaattgt  ataaaaaaag  acgcctgtat
23161  aaaatacaga  cgccactat   aattataaga  ttacatggtt  aattaccaaa  aatggtaacg
23221  aatatatacg  tgttttaaag  gataaaactt  taataatatt  aaattatatt  atcttatatc
23281  agggatctgc  aatataatat  tattatttct  atttatcagt  aacataatat  cgaagaatc
23341  tattactgga  tttcttaatt  tttggggtaa  aacttttctt  atgcgaaact  tactaatcgg
23401  ctggaaagaa  tttatgcaag  cgtaactatt  accttttacct tttttacct   tatcaattgc
23461  tgatactatg  ttattaatgt  ttctgtcaat  tttatttaat  ttatttcaa   ttctaaact
23521  atcagatata  aattcaataa  aatacttct   agtgatgaat  tctgtgttgt  ttttttggta
23581  ttttttatcg  aaaacttctg  ttattatatgc gtttttctat  tgcgcgctaa  ttaaatttaa
23641  aaacaatctt  agtaaatagt  gaatatctga  atctaacttt  atcattttg   acttttttgtt
23701  ttctttagag  gataaggaa   cccatttcaa  taacatttag  ttcttatta   acgtttttga  cattttatt
23761  catcactatt  gcaaagtgtg  aattagaaaa  aattagaaat tcttatta    acgtttattac cgaaatctac
23821  aaaactatt   tctccttgtt  taaacttttgg ataaaacct   ttatgttt    ttcaccttc
23881  aaatctttg   agtaaatagc  gaatatctga  atctaacttt  ttaaattttg  gatttccaga
23941  agtttttaat  ttattaatgc  gttttttctat attatgcgtc  atcattttctc ctttattctc
24001  gctcacactc  tcaccaccat  cttctttggt  tcaacgtcta  cgttgtagg   ttagtaaaat
24061  cataatgaat  cttctttggt  taacttatcg  tttgtgaaat  aaattccaag
24121  tatttacgcg  cattatgtga  cgataaatct  ttaggtaact  cataagtgaa  tggttgatta
```

FIG. 2M

```
24181  ccactagtta  aaacttcata  tactatagtt  tcttttttta  tttgcaatt   agttattttc
24241  attataaact  cctttaaac   actgctgaaa  tagacgtctt  tttcaaataa  gcatgattaa
24301  tactttaatt  ctttaatcca  catatattta  aaagtgaggt  agtaggtaat  aaatataaga
24361  cttaaagtta  agattgcttt  tttcatgtca  atttctctt   tgtttatatt  tatattaaag
24421  cgctaaatat  acgttattaa  tcacaataca  actttgccca  ttactttaat  atcactaaac
24481  gaagcgactt  tgatatcatc  atacttcgga  tttagagata  ccaaattaat  atagtcttcg
24541  catatatcta  cacgcttgat  aagacttact  caacgagtgc  aattgtacca  ataggttcc
24601  tcttttaatag aatcttttt   cttaataaaa  gcgtatgttc  ctgttttaa   catagcttcc
24661  attgaatcac  cattaactaa  aatacaaaaa  tcagcatttg  atggcgtttc  gtcttcttta
24721  aaaatactt   cttcatgcaa  tatgtcatca  tataattctt  ctcctatgcc  agcaccagtt
24781  gcaccacatg  caatatacga  tactagttta  gactcttat   attcatctat  agaagtgact
24841  ttattctgtt  catctaattg  ctcatttgca  tagttaagta  cgttttcttg  gcgggagg
24901  gtgagttgag  aaaatatgtt  attgattttt  gacattatct  tttcatcttg  acgttcttcg
24961  tcaggaactc  gataagaatc  tacatcatac  cccataagcc  acgcttcacc  gacatttaaa
25021  gttttagata  ataagaataa  tttatgttgg  tctgagaaag  accttccatt  aacatactgg
25081  gataagtgac  ttttttgacat ttaatattc   aattcttttt  gaaaggttt   cgactttctt
25141  agaatatcta  cttgacgcaa  gtttctatct  ttcataattt  gttttaatct  ttcagaagtg
25201  tttgcattg   gtaatgcctc  cttgaaattc  attatatagg  aaggaaata   aaaatacaata
25261  caaagttca   actttttaa   cttttgtgt   tgacattgtt  caaattggg   gttatagtta
25321  ttatagttca  aatgtttgaa  cttaggaggt  gattattttga atactaatac  aactttgat
25381  tttcgttat   tgaacggtaa  gatagtcgaa  gtgtactcga  cacaattaa   ctttgctata
25441  gcttaggtg   tatcagaaag  aacttgtct   ttgaagttga  acaacaaagt  accatggaaa
25501  acaacagaca  ttattaagc   ttgtaagtta  ttgggaatac  ctataaaaga  tgttcacaaa
25561  tatttttta   aacagaaagt  tcaaatgttt  gaacttaata  agtaaaggag  gcataacaca
25621  tgcaagaacg  agaaaaggtt  aataaaagta  acacatcttc  aaatgaagca  tcaaaaccttt
25681  ttaggacaaa  ttgaagctta  cgacaaaacg  cttaaagaaa  gacgcattcg  tcgagacctt
25741  tacaacaaac  acctaagcat  cgatataaca  aatatagaaa  taaagtacac  aatggtagag
25801  gatgaaatta  ctaaaaagct  acgaagtgct  atcaaagagt  tccaaaaagt  agtgaaagcg
25861  ttagacaagc  ttaacggtgt  tgaaagcgat  aacaaagtta  ctgatttaac  agagtggcgg
25921  aaagtgaatc  agtaacattc  acttcttaat  ataaccacgc  ttatcaacat  ccacattgag
25981  cagatgtgag  cgagagctgg  cgatgatatg  agccgcgttt  aaatacattc  gatagtcatt
26041  gcgataacg   tctgctgaat  gtggtttg    aggaaaaagg  aggataactca aatgcaagca
26101  ttacaaacat  ttaattttaa  agagctacca  gtaagaacag  ttaggaaattga aaacgaacct
26161  tattttgtat  gaaaagatat  tgctgagatt  ttaggatatg  caagatcaaa  caatgccatt
```

```
28261 caaaacggta taaacatcgg gcaacgcaga ttgttttgagt ggttacgtca aaacggattc
28321 cttattaaac gcaaggtgt ggattataac atgcctacac agtattcaat ggaacgtgag
28381 ttattcgaaa ttaaagaaac ctactggaat cattcggacg gtcacacatc aattagtaag
28441 acgccaaaag taacaggtaa aggacaacaa tactttgtta acaaagtttt aggagaaaaa
28501 caaacaactt aataggagga attacaaatg aacgcactat acaaaacaac cctcctcatc
28561 acaatggcag ttgtgacgtg gaaggtttgc aagattgaga agcacactga aaaactgtg
28621 attagtagca ggggcgttgag tgactatcta aacaaccat cttaaccat accgaaagat
28681 gctgaaaatt ctactgaatc tgctcgtcgc cttttgaagt tcgccgaaca aactattagc
28741 aaataacaac attatacacg aaaggaaaaga aagtttgtaa aaaatttgtaa gtaccaccaa
28801 caccagaaaa cacatataga ggagtactata atttcacagt atacaactgg gcaacactta
28861 acccgcaaaga tcaattgttt gtaagatgta ttatacattga ttattcacca ttgaaatatt
28921 tgattaatat taatttaggt gaagagtatt tgatcagaaa gcataaaaaa acaggcactc
28981 aggatattaa atgagcaaca cgttcctata ctacctagta gcagtattat gcttcacagt
29041 cttagcgatt gtacttatgc tgtactacaa cttcactaca ttcaaagaat ttgcgggatt
29101 cgcaagtatc gcaacattca cagtatcaaa agaatgcttt aaaaatcata aaaaaactc
29161 ctacttgttg gagcaagtaa aagatgtcgat ttcaagaa cacttaaaagc cgaaatcata ttcaatataa
29221 aacgaaaaac ggagcaagtc aagatgcgat tttaagctat acgaaatcatg cgcatatcaa ggcatatcaa
29281 ttcatgttaa cggattgaac agatatgaac aacgtaccaa ttaagctaat taagcatgc ttatgtcgta
29341 tacaagttaa agatagatat ggcatcagac ttatttaacc ttatttaacc aagcaataga tgaatggatt
29401 acttagatat ggcatcagac ttatttaacc ttattaact ttatttaact tcatgaaatg gtaggaggtc
29461 cagacgaaca ggacagacta attaacttag cgtcatagc atatgaaaat ttatataact aacaaacca
29521 agactgtaac ttatatcatt agttactcca caataggaaa tagagctagg aatcaagaaa aacaaacca
29581 ctgataacaa ttcagatatt aatagtatc caacacttt gttatgttg gagtttaacg gagtttaacg
29641 gtatggaaga agcgagtatc aatatggatt gtgaacatc actgaggaaa acaagaaac acagtgacag
29701 aaactattga gtacgaggag gtagaagatc aaagataaat aataaaattggc tacaaggat
29761 gtaagcatac tcaaaaaact aaaaattttg cattaacgaa ccacgttgc tacaaggatca
29821 tataaatttg cagtatacgg ttatacatt cgtcatacga cggttacgaa cgggttacga
29881 aaagacgctt tcgtcattga ttcaaactt gttatgttg taaatttttt accctcaaatt
29941 gacgtagaaa tcgagaacta agcgagtatc aatatgttg tagttatttg aactattcaa
30001 gtatggaaga tgagagaaga tgagagaaga atcaatgatt atgaaaataa accaacgttt
30061 ttacaggaga tgagagaaga atatgacatt gaatgatgtg gtcagtatgt acagaggat
30121 aaacttagag atatgacatt gaacgaatt tgaacgaatt gtcagtatgt acagaggat
30181 aatgattggg gagaagttgc gaagaattg gtaacgaatt gtcagtatgt acagaggat
30241 caagaagaat acaaattcca ctttgttatt acaggtcatg aaggtatcaa caaagataaa
```

FIG. 2P

```
30301 gatgatgaag gtagcactat caaccctact atcactattg aagcgcaaga acaaattaaa
30361 aaagctatta cttctcaaag tgatgtgtta gctaggcaa tgattgaaga atttgatgat
30421 aacggagaaa agaaagctag atatattcta aacgctgaac cttctaatac ctttgaaaca
30481 aagattagac attcacttc aataacaatt aacaataaga aattgcaaa tcctagcatt
30541 acggacgtag tagaagcaat tagaaatgga aagcgcaat acaatagaag gacggtattt
30601 aattatgaaa atcacaggac aagcgcaat tactaaagaa acaaatcaag aaaagttta
30661 taacggctca gcagggttc aagctggaga attcacagtg attcacacaat atattgaatt
30721 caatgataga gaaaatagat atttcacaat cgtatttgaa aatgatgaag gcaaacaata
30781 taaacataat caattgtac cgccgtataa atatgattc caagaaaaac aattgattga
30841 attagttact cgattaggta ttaagttaaa tcttcctagc ttagatttg ataccaatga
30901 tcttattggt aagttttgtc acttggtatt gaaatggaaa ttcaatgaag atgaaggtaa
30961 gtattacg gattttcat ttattaaacc ttacaaaag ttatttaacaa ttgttaacaa
31021 acctattcg aagacagata agcaaaaagc aaccattga aacgggcac aacaacaaac
31081 atcaatgtct caacaagca atccttga aacagcgtgc caatttggat atgacgacca
31141 agatttagc tttaaggtg tggtttaat gcaatacatt acaagatacc agaaagataa
31201 cgacggtact tattccgtcg ttgctactgg tgttgaactt gaacaaagtc acattgact
31261 actagaaaac ggatatccac taaagcaca tattcgcaat ccgacaata aaaaactatc
31321 tatagaacaa cgcaaaaaaa cgcaaaaaaa tattattaca atagaacttc actgggcga
31381 accagtagaa tcaactagaa aattgcgcaat gttctatgaa gaaattatga aaggttatga
31441 agaaatcagt ctgcgcgact gttctatgaa aatacctatt gagtgtagaa acgagtaagt
31501 agcgttatg tttcatcatc aaataccttat caacgcaaac bagtgtagaa acgagtaagt tgttaagcga
31561 agataaagcg ttattatatt gggctacaat atgaagcagt caaccgcaac cggcagaggc atgaacagaa acaaatgaa
31621 tcacgcagac ctgccacatt agcgttatg ataaatacca tcgcgaacat aacatgcgat
31681 ccactatgac aaacatgtat tcgtttgatg ataaatacca cttgcatgac aagttgatga
31741 tggcgttaag aaaatgttga aaatgttgga aaggagagaa aaagaggagaa aataataaaa
31801 gaggctcaat taatcgtcat cttggcggaa gagattagaa aatctatgca tgctgtaaaa
31861 atagcactcc tttaaaatc tccgttagt taatacaggt tttacaaaa gctttaccat
31921 gtggagaaaa actaattgag cctttttga tgtctattac ccaggctg taatgtaact
31981 aggcggacaa aaatacttc ccagaaagtt tacttattgt ttcttggttg tgctcggact
32041 ttaatacttc aaattcaatg tctaatccg aaacaaatct ttgttttct ataatcttat
32101 ttaacattct tttaacaat aaaatgttga aaggcataaa acttattata tttgttaaagt
32161 taaagtgatt taaaactga ggagcataaa acttattata ttgttaagt
32221 aagacatgtc aaaagttca tttaaaaacc ctaaccttac taggttatta attgaaattt
32281 cggttgattc tatatctaac ggagagtctt ttattaacgt gtccgatata ttcataccgt
```

FIG. 2Q

```
32341 cattctttgg gtttaaaacc gctctatatt taacggcagg atgtacttcg tgattcttta
32401 aatgttttaa aagaatagca tcatttgggg ataattgttt aattattca acaaatgaat
32461 ggtggggttaa tgagttttt ctgtcatcca tagatgatgc tattagtttt gcgaacatat
32521 tacttaaagt ttttcacta atgtaaaact ttgaagcttc tagagaagag cctagaagag
32581 aaaattgtgg ttcttgtaaa ttatttttag gtacagaaga tatttctttt ttaaattgtt
32641 ctttgaattt ttcaaattct actctctttt gataaataac tttatccaca taaaggtgga
32701 atttcccaaa gacaagttcc caagttttag agaatgtttc tacaggccct tttgatgcgc
32761 cttcaataat tttatcaata cctttaccta aatataggatc cataattatt cacccccaat
32821 ctaacgcaat agcgataata aaattatacc agaaaggaga atcaacatga ctgaccaacc
32881 aagttactac tcaataatta cagcaaatgt cagatacgat cagataactta ctgacagcga
32941 aaagttactt tttgcagaaa taacatcttt aagtaacaaa tacggatact gcacagcaag
33001 taatggttac tttgcaactt tatacaacgt tgttaaggaa actatatctc gtagaatttc
33061 gaaccttacc aactttggtt atctaaaat aaagaaggta atgaagttaa aaatcaatac
33121 acaaaggaag atgtaccct tgacgcaaac gtcaataact attgacgcaa atattacaag
33181 cctattgat aattctgtca ataccctat tgacgcaaat gtcaaagaga atattgtcgg gcaacccgac
33241 tattaataat acaagtaata acaatatata tagaatagat atattgtcgg gcaaccgac
33301 agcatcttct atacagcta aagaaattat cgattactta aacaaaaaag cgggcaagca
33361 ttttaaacac aatacagcta aagaaattat tttattaaa gcaagatgga atcaagattt
33421 tagtttggag gattttaaaa aaacaaagga tttcattaaa gcaagatgga atcaagattt
33481 tagcgataaa tacctagac cagaacact tatcaaaaca gctgagtggc taaacacgga
33541 tcaaaaata caaccaactg gcacggatca ttttggcagt aaatttgagg ggtacctcaa
33601 ttgggattag gggatatatta tgaaaccact attcagcgaa atgaaatgt gagagatacg aagcttgaa
33661 aaaatatcaa cctactcatg tcgaaaaagg attgaaatgt gaagatgtg gaagtgaata
33721 cgacttatat aagtttgctc ctactaaaaa acacccgaat ggttacgagt ataaagacgg
33781 ttgcaaatgt gaaatctatg aggatatataa gcgaaacaag cgaaacaag taaacaacat
33841 attcaatcaa tcaaacgtta atccgtctta aagagatgca acagcaata actacagcc
33901 acaaagaa acaacaagtac acgctaaaca acagcaata agttcatgc gagtacgta aaggcttctc
33961 tacaaagaa ccaaaatcat taatattgca aggttcatgc taaaggcat aaagccact
34021 cgacttatat atcgcaaaag cagtcaaagc tcaaagcgac atacaacaaa aatgcagtag agactacaga
34081 ttgcaaatgt atggatcgta atttgcaa gtgatatgta ctagatgata tggtgtaga
34141 cgagctagtc agattgctaa cacttgta ataactttt cagcatttgt gaacagag taggtaaaaa
34201 aaacacagag cacatctaa ataactaact ttagtgataa agaacttaaa actggcacg
34261 caacatcttt acaactaact ttagtgataa agaacttaaa actggcaacg acgattcag
34321 tataaattcg agaatgaaaa aaaagtaaga gtaatcggag acgattcag
```

```
36421  tgtgactgga  tatgtatcaa  ttaacgataa  atttactgtt  caagaggaga  tataacaatg
36481  aaaatcaaag  ttaaaaaaga  aatgagatta  gatgaattaa  ttaaatgggc  gcgagaaaat
36541  ccggatctat  cacaaggaaa  aatattttt   tcaacaggat  ttagtgatgg  attcgttcgt
36601  tttcatccaa  atacaaataa  gtgttcgacg  tcaagttta   ttccaattga  tatcccttc
36661  atagttgata  ttgaaaaaga  agtaacggaa  gagactaagg  ttgataggtt  gattgaatta
36721  ttcgagattc  aagaaggaga  ctataactct  acactatatg  agaacactag  tataaaagaa
36781  tgtttatatg  gcagatgtgt  gcctaccaaa  gcattctaca  tcttaaacga  tgacctaact
36841  atgacgttaa  tctggaaaga  tggggagttg  ctagtatgat  gttgaaattt  aaagcttggg
36901  ataaagataa  aaaagttatg  agtattattg  acgaaatcga  ttttaatagt  gggtacattt
36961  tgatttcaac  aggttataaa  agtttcaatg  aagtaaact   attacaatac  acaggattta
37021  aagatgtgca  cggtgtggag  atttatgaag  gggatatatt  tcaagattgt  tattcgagag
37081  aagtaagttt  tatcgagttt  aagagaaggag gccttttatat aacttttagc  aatgtaactg
37141  aattactaag  tgaaaatgac  gatattattg  aaattgttgg  aaatattttt  gaaaatgaga
37201  tgctattgga  ggttatgaga  tgacgttcac  cttatcagat  gaacaatata  aaaatctttg
37261  tactaactct  aacaagttat  tagataaact  tcacaaagca  ttaaaagatc  gtgaagagta
37321  caagaagcaa  cgagatgagc  ttattggga   tatagcgaag  ttacagagatt gtaacaaaga
37381  tctagagaag  aaagcaagcg  catggatagg  gtattgcaag  agcgttgaaa  aagatttaat
37441  aaacgaattc  ggtaacgatg  atgaaagagt  taaattcgga  atggaattaa  acaataaaat
37501  ttttatggag  gatgacacaa  atgaataatc  gcgaaaaaat  cgaacagtcc  gttattagtg
37561  ctagtgcgta  taacggtaat  gacacagagg  ggttgctaaa  agagattgag  gacgtgtata
37621  agaaagcgca  agcgtttgat  gaaaatgac   agggaatgac  aaatgctatt  caacattcag
37681  ttaaagaagg  tattgaactt  gatgaagcag  tagggattat  ggcaggtcaa  gttgtctata
37741  aatatgagga  ggaataggaa  aatgactaac  acattacaag  taaaactatt  atcaaaaaat
37801  gctagaatgc  ccgaacgaaa  tcataagacg  gatgcaggtt  atgacatatt  ctcagctgaa
37861  actgtcgtac  tcgaaccaca  agaaaaagca  gtgatcaaaa  atgacatagt  tgtgagtata
37921  ccagaggct   atgtcggact  attaactagt  cgtagtgttg  taagtaagtg  aacgtattg
37981  gtgattgaa   caggcaagat  agacgcggga  aataccctt   ttatatgatg  atttaggga
38041  aatgatgaag  aacgtgatgg  ggaatattaaaa ataccctt   ttataactatg  atataacgc
38101  gatggattaa  taagcatttt  agatataaaa  ggtaactatg  taccaagatgg aagaggcata
38161  agaagagttt  accaaaatcaa caaaggcgat  aaactagctc  aattggttat  cgtgcctata
38221  tggacaccgg  aactaaagca  agtggaggaa  ttcgaaaagtg tttcagaaagtg tggagcaaaa
38281  ggcttcgaa   gtagcggagt  gtaaagacat  cttagatcga  gttaaggagg  ttttggggaa
38341  gtgacgcaat  acttagtcac  aacattcaaa  gattcaacag  gacgaccaca  tgaacatatt
38401  actgtggcta  gagataatca  gacgttaca   gttattgagg  cagagagtaa  agaagaagcg
```

FIG. 2T

```
38461  aagagaagt  acgaggcaca  agttaaaaga  gatgcagtta  ttaaagtggg  tcagttgtat
38521  gaaaatataa  gggagtgtgg  gaaatgacgg  atgttaaaat  taaaactatt  tcaggtggag
38581  tttattttgt  aaaaacagct  gaaccttttg  aaaaatatgt  tgaaagaatg  acgagtttta
38641  atggttatat  ttacgcaagt  actataatca  agaaaccaac  gtatattaaa  acagatacga
38701  ttgaatcaat  cacacttatt  gaggagcatg  ggaaatgaat  cagctgagaa  ttttattaca
38761  tgacggtagt  agtttgatat  tacatgaaga  tgaattattt  aacgaaatag  tatttgtttt
38821  ggacaatttt  agaaatgatg  atgactattt  aacgatagaa  aaagattatg  gcagagaact
38881  tgtattgaac  aaaggtttata  tagttgggat  caatgttgag  gaggcagatg  atgattaaca
38941  tacctaaaat  gaaattccg  aaaaagtaca  ctgaaataat  caaaaaatat  aaaaataaag
39001  cacctgaaga  aaaggctaag  attgaagatg  attttattaa  agaaattaaa  gataaagaca
39061  gtgaatttta  cagtcctacg  atggctaata  tgaatgaata  tgaattaagg  gctatgttaa
39121  gaatgatgcc  tagtttaatt  gatactggag  atgacaatga  tgattaaaaa  acttaaaaat
39181  atggatgggt  tcgacatctt  tattgttgga  atactgtcat  tattcggtat  attcgcattg
39241  ctacttgtta  tcacattgcc  tatctataca  gtgctagtt   accaacacaa  agaattacat
39301  caaggaacta  ttacagataa  atataacaag  agacaagata  aagaagacaa  gttctatatt
39361  gtattagaca  acaaacaagt  cattgaaaat  tccgacttat  tattcaaaaa  gaaatttgat
39421  agcgcagata  tacaagctag  gttaaaagta  ggcgataagg  tagaagttaa  aacaatcggt
39481  tatagaatac  actttttaaa  tttatatccg  gtcttatacg  aagtaaagaa  ggtagataaa
39541  caatgattaa  acaaatacta  agactattat  tcttactagc  aatgtatgag  ttagttaagt
39601  atgtaactga  gcaagtgtat  attatgatga  cggctaatga  tgatgtagag  gcgccgagtg
39661  attacgtctt  tcgagcggag  gtgagtgaat  aatgagaata  tttattatg   atttgatcgt
39721  tttgctgttt  gctttcttaa  tatccatata  tattattgat  gatggagtga  taataaatgc
39781  attaggaatt  tttggttatgt  ataaaattat  agattccttt  tcagaaaata  gaggtgttgt
39841  gtagataaaa  atgaacgagc  aaataatagg  aagcatatat  actttagcag  aacgtaaaaa
39901  gctttattca  gttaaagaga  tttttaggta  aagcatatat  tctaacttac  ctaaaaagat
39961  aatcaattta  gaacaaatat  atccgataca  caacagaaca  tctaaaaagg  ttgatattga
40021  gattggagct  tatattattc  caacagaaca  gcatgaattt  tttaaaaggt  ttgatttag
40081  agtctttaat  aatttagata  agcaaagtaa  aaaagcgtat  gaaaatgtta  ttggatttag
40141  acaaatgatt  aatttatcaa  atagagttaa  ggcaatggaa  gatttttaaga  tgagtttcaa
40201  caatgaattt  gtaaagagc   agatttttt   taatccttct  tttgttatgg  aaacaattgc
40261  tattataaat  agtacaaatc  agatacaaaa  aagatatcaa  taatcttaaaa  atataattaa
40321  tgaaaataga  gcttataatc  atattgatag  ttgataaatt  tttatcact   tcagagtacc  gacgaaaaat
40381  aaacgattat  aatctttatc  tgataaaag  aaagaattat  tattaattta  acaagagga  gatttaaatg
```

```
40501  atgtggatta ctatgactat tgtatttgct atattgctat tagtttgtat cagtattaat
40561  agtgatcgtg caagagagat acaagcactt agatatatga atgattatct acttgatgaa
40621  gtagttaaaa ctaaaggta caacggtta gaagaataca ggattgaatt gaagcgaatg
40681  aataacgata ttaaaaagta atttatatta tcggaggtat tgcattgaat gataaagatt
40741  gagaaacacg atatcaaaaa gcttgaagaa tacattcagc acatcgataa ctatcgaaga
40801  gagttgaaga tgcgagaata tgaattactt gaaagtcagc gaaagtgat tgcggagct
40861  ggcaaaagta atttgccggg taacccgatt gaacgatgtg caataaagaa gtttagtgat
40921  aacaggtaca atacattaag aaatatagag atagattgat attgtcctat aggtgaaagt
40981  gatgaggata cgcttgagtt attaaggttt attaaggttt acaagtagaa tggttgttat
41041  gaatgggaag atatagcaca agatattggg agatattggg acaagtaaga attggttatg acgtagaagg
41101  aatgcactga tcgataagtt agcaaagtat attggttatg tgtagcggac ttttaccta
41161  tgtaagtccg cattaaaaca gtttattatg ttagtatcag attaatattt aaagttatta
41221  aatgctaata cgacgcatga acaagaggcg catcactatg tgatgtgtct tttatttat
41281  gagtatgaat catgttcaaa ctaattgtaa atacattact acacatcaag tatagatgag
41341  tcttgatact acttaagtta tataagtga aacattatga tgactaaaga cgaacgtata
41401  cgattctata agtctaaaga atggcaaata acaagaaaa gagtgctaga aagagataat
41461  tatgaatgtc aacaatgtaa gagagacggc aagttaacga catatgacaa aagcaagcgt
41521  aagtcgttgg atgtagatca tatattatcg ctagaacatc atccggagtt tgctcatgac
41581  ttaaacaatt tagaaacact gtgtattaaa tgtcacaaca aaaagaaaa gagatttata
41641  aaaaagaga ataaatggaa agacgaaaa tggtaaaata cccgggtca aaaaaatcaa
41701  aagcgatc
```

FIG. 2U

A.  SEQ ID NO: 4
1    ATGGTAACCA AAGAATTTTT AAAAACTAAA CTTGAGTGTT CAGATATGTA
51   CGCTCAGAAA CTCATAGATG AGGCACAGGG CGATGAAAAT AGGTTGTACG
101  ACCTATTTAT CCAAAAACTT GCAGAACGTC ATACACGCCC CGCTATCGTC
151  GAATATTAA

B.  SEQ ID NO: 5
1   MVTKEFLKTK LECSDMYAQK LIDEAQGDEN RLYDLFIQKL AERHTRPAIV EY

FIG. 4

Predicted Tryptic Peptide Masses of Conceptual ORF in Contig 1383 :

MGGGQSIMKQFKSIINTSQDFEKRIEKIKKEVINDPDVKQFLEAHRAELTNAMIDED
LNVLQEYKDQQKHYDGHKFADCPNFVK|GHVPELYVDNNR|KIRYLQCPCKIKYDEE
RFEAELITSHHMQRDTLNAKLKDIYMNHRDRLDVAMAADDICTAITNGEQVKGLY
LYGPFGTGKSFILGAIANQLKSKKVR|STIIYLPEFIR|TLKGGFKDGSFEKKLHRVREA
NILMLDDIGAEEVTPWVRDEVIGPLLHYRMVHELPTFFSSNFDYSELEHHLAMTRDG
EEKTKAARJIERVK|SLSTPYFLSGENFR|NN

Tryptic peptide fragment :

GHVPELYVDNNR         Predicted Peptide Mass MH$^+$ = 1413.538

STIIYLPEFIR          Predicted Peptide Mass MH$^+$ = 1352.6221

SLSTPYFLSGENFR       Predicted Peptide Mass MH$^+$ = 1618.7923

FIG. 5

SEQ ID NO: 6   DnaC nucleotide *B. subtilis*

|  |  |  |  |  |  |
|---|---|---|---|---|---|
| 1 | ATGACAGACC | TTCTGAATGA | CCGGCTTCCT | CCGCAAAATA | TAGAAGCCGA |
| 51 | ACAAGCCGTG | TTAGGCGCTA | TTTTTTACA | GCCGTCTGCT | TTAACACTGG |
| 101 | CTTCAGAAGT | ATTGATTCCA | GATGATTCT | ATAGAATGTC | CCACCAAAAA |
| 151 | ATCTATAATG | CGATGCTGGT | GCTCGGTGAC | CGAGGTGAAC | CGGTTGATCT |
| 201 | GGTGACAGTT | ACATCAGAGC | TTGCGAACAC | AGACCTGCTG | GAAGAAGTAG |
| 251 | GCGGTATTTC | ATATTTGACA | GATATCGCAA | ACTCGGTGCC | GACAGCGCT |
| 301 | AACATAGAAT | ATTACGCGAA | AATCGTTGAG | GAAAAATCGA | TTCTTCGCCG |
| 351 | ATTAATCAGA | ACTGCGACAA | CGATTGCTCA | AGACGGGTAT | ACCCGTGAGG |
| 401 | ATGAGGTCGA | GGATTACTC | AGTGAAGCGG | AAAAAACGAT | TATGGAAGTG |
| 451 | GCACAGCGCA | AAAACACGAG | TGCCTTCCAA | AATATTAAGG | ACGTCCTTGT |
| 501 | CCAGACCTAT | GATAATATCG | AACAGCTTTA | CAATCGAAAA | GGTGATATCA |
| 551 | CGGGAATTCC | AACAGGGTTT | ACGGAGCTTG | ACCGGATGAC | TGCGGGTTTC |
| 601 | CAGCGCAACG | ACTTGATCAT | TGTGGCTGCC | CGTCCTTCAG | TAGGGAAAAC |
| 651 | AGCCTTTGCC | CTGAACATCG | CACAAAACGT | GGCGACGAAG | ACCGATGAGA |
| 701 | GCGTAGCGAT | TTTCAGTCTT | GAGATGGGTG | CCGAGCAGCT | CGTTATGCGT |
| 751 | ATGCTCTGTG | CCGAGGGAAA | TATCAATGCC | CAGAATCTCC | GTACAGGTAA |
| 801 | CCTGACCGAA | GAGGATTGGG | GCAAGCTGAC | GATGGCAATG | GGAAGCCTAT |
| 851 | CGAACAGCGG | GATTTACATC | GATGATACAC | CGGGTATTCG | AGTGAGTGAA |
| 901 | ATCCGTGCCA | AGTGCCGCCG | CTTGAAGCAG | GAAAGCGGGC | TGGGCATGAT |
| 951 | TTTGATCGAT | TACCTGCAAT | TGATTCAGGG | AAGCGGGTCGT | TCAAAGGACA |
| 1001 | ACCGTCAGCA | GGAAGTATCT | GAAATTTCCC | GTGAACTGAA | GTCGATTGCG |
| 1051 | AGGGAGCTGC | AAGTCCCTGT | TATCGCGCTT | TCTCAGCTTT | CCAGGGGTGT |
| 1101 | TGAGCAGCGT | CAGGATAAAC | GTCCGATGAT | GTCTGATATC | CGGGAATCAG |
| 1151 | GAAGTATCGA | GCAGGACGCG | GATATTGTCG | CGTTCCTTTA | TCGTGATGAC |
| 1201 | TACTATGACA | AAGAAACCGA | GAATAAAAAT | ATTATCGAAA | TTATTATCGC |
| 1251 | CAAACAGCGT | AACGGCCCCGG | TAGGAACCGT | GTCTCTTGCG | TTCGTAAAAG |
| 1301 | AATACAACAA | ATTCGTCAAC | CTGGAACGGC | GTTTGATGA | CGCAGGCGTT |
| 1351 | CCGCCCGGCG | CA |  |  |  |

SEQ ID NO: 7      DnaC nucleotide S. aureus

```
   1  ATGGATAGAA  TGTATGAGCA  AAATCAAATG  CCGCATAACA  ATGAAGCTGA
  51  ACAGTCTGTC  TTAGGTTCAA  TTATTATAGA  TCCAGAATTG  ATTAATACTA
 101  CTCAGGAAGT  TTTGCTTCCT  GAGTCGTTTT  ATAGGGGTGC  CCATCAACAT
 151  ATTTTCCGTG  CAATGATGCA  CTTAAATGAA  GATAATAAAG  AAATTGATGT
 201  TGTAACATTG  ATGGATCAAT  TATCGACGGA  AGGTACGTTG  AATGAAGCGG
 251  GTGGCCCGCA  ATATCTTGCA  GAGTTATCTA  CAAATGTACC  AACGACGCGA
 301  AATGTTCAGT  ATTATACTGA  TATCGTTTCT  AAGCATGCAT  TAAAACGTAG
 351  ATTGATTCAA  ACTGCAGATA  GTATTGCCAA  TGATGGATAT  AATGATGAAC
 401  TTGAACTAGA  TGCGATTTTA  AGTGATGCAG  AACGTCGAAT  TTTAGAGCTA
 451  TCATCTTCTC  GTGAAAGCGA  TGGCTTTAAA  GACATTCGAG  ACGTCTTAGG
 501  ACAAGTGTAT  GAAACAGCTG  AAGAGCTTGA  TCAAAATAGT  GGTCAAACAC
 551  CAGGTATACC  TACAGGATAT  CGAGATTTAG  ACCAATGGAC  AGCAGGGTTC
 601  AACCGAAATG  ATTTAATTAT  CCTTGCAGCG  CGTCCATCTG  TAGGTAAGAC
 651  TGCGTTCGCA  CTTAATATTG  CACAAAAAGT  TGCAACGCAT  GAAGATATGT
 701  ATACAGTTGG  TATTTTCTCG  CTAGAGATGG  GTGCTGATCA  GTTAGCCACA
 751  CGTATGATTT  GTAGTTCTGG  AAATGTTGAC  TCAAACCGCT  TAAGAACGGG
 801  TACTATGACT  GAGGAAGATT  GGAGTCGTTT  TACTATAGCG  GTAGGTAAAT
 851  TATCACGTAC  GAAGATTTTT  ATTGATGATA  CACCGGGTAT  TCGAATTAAT
 901  GATTTACGTT  CTAAATGTCG  TCGATTAAAG  CAAGAACATG  GCTTAGACAT
 951  GATTGTGATT  GACTACTTAC  AGTTGATTCA  AGGTAGTGGT  TCACGTGCGT
1001  CCGATAACAG  ACAACAGGAA  GTTTCTGAAA  TCTCTCGTAC  ATTAAAAGCA
1051  TTAGCCCGTG  AATTAGAATG  TCCAGTTATC  GCATTAAGTC  AGTTATCTCG
1101  TGGTGTTGAA  CAACGACAAG  ATAAACGTCC  AATGATGAGT  GATATTCGTG
1151  AATCTGGTTC  GATTGAGCAA  GATGCCGATA  TCGTTGCATT  CTTATACCGT
1201  GATGATTACT  ATAACCGTGG  CGGCGATGAA  GATGATGACG  ATGATGGTGG
1251  TTTCGAGCCA  CAAACGAATG  ATGAAAACGG  TGAAATTGAA  ATTATCATTG
1301  CTAAGCAACG  TAACGGTCCA  ACAGGCACAG  TTAAGTTACA  TTTTATGAAA
1351  CAATATAATA  AATTTACCGA  TATCGATTAT  GCACATGCAG  ATATGATGTA
1401  A
```

FIG. 6A-3

Optimal global alignment

Sequence 1  SEQ ID NO: 6  DnaC nucleotide B. subtillis(1471 letters)
Sequence 2  SEQ ID NO: 7  DnaC nucleotide S. aureus(1513 letters)

```
seq1    1 AT-GACAGACCTTCTGAATGACCGGCTTC---CTCCGCAAAATATAGAAGCCGAACAAGC   56
            || ||| |||  ||||||||  |   ||    ||||  ||||||| ||||| || || |
seq2    1 ATGGATAGA----ATGTATGAGCAACAAATCAAATGCCGCATAACAATGAAGCTGAACAGTC  56 seq1   57 CGTGTTAGGCGCTATTTTTTACAGCC-GTCTGCTTAACACTGGCTTCAGAAGTATTGA    115
           ||||| ||  |||||| ||| ||| ||||| || || || ||||||||||| ||||
seq2   57 TGTCTTAGGTTCAATTATTATAGATCCAGAATTGATTAAATACT-ACTCAGGAAGTTTTGC  115 seq1  116 TTCCAGATGATTTCTATAGAAATGTCCCACCAAAAAATCTATAATGCGATGCTGGTGCTCG  175
           |||| ||  ||| ||||| ||||| || ||||||||||||  |||| || ||  |||
seq2  116 TTCCTGAGTCGTTTTATAGGGGTGCCCATCAACATATTTCCGTGCAATGATGCACTTAA    175 seq1  176 GTGACCGAGGTGAACCGGTTGATCTGGTGACA--GTTACATCAGAGCTTGCGAACACAGA  233
           || |||  || |||  || || | |||| ||  || || ||||||  ||| || |||
seq2  176 ATGAAGATAAAGAAATTGATGTTGTAACATTGATGATC--AATTATCGACGGAAGG     233 seq1  234 CCTGCTGGAAGAAGTAGGCGCGGGTGGCCCGCAATATCTTGCAGAGTTATCTACAAAT--GTACCA  291
           || || ||  || || || || ||| ||  ||  || ||   ||| || ||| ||||  |  ||
seq2  234 TACGTTGAATGAAGCGGGTGGCCCGTATACCCGTGAGGATGAGGTCGA    291 seq1  292 ACAGCGCGGCTAACATAGAATATTCAGTATTATACGCGAAAAATGTCGATT-CTTCGCCG  350
           |||||||  |||| ||||| ||| || ||  |||  ||||||| || |   ||  |
seq2  292 ACGACGCGAAATGTTCAGTATTATACTGATATCGTT-TCTAAGCATGCATTAAAACGTAG  350 seq1  351 ATTAATCAGAACTGCGACAACGATTGCTCAAGACGGGTATACCCGTGAGGATGAGGTCGA  410
           || ||||| ||||| ||| | ||| || |||| |||  || ||| ||||||| |  |||
seq2  351 ATTGATTCAAACTGCAGATAGTATTGCCAATGATGGATATATGATGAACTTGAACTAGA  410
```

FIG. 6A-4

```
seq1  411  --GGATTTACTCAGTGAAGCGGAAAAAAACGATTATGAAGTGGCA-CAGCGCAAAAACAC  467
              ||||||||||||||||||||  ||||||||||||||||||| ||||||||||||||||
seq2  411  TGCGATTT---TAAGTGATGCAGAACGTCGAATTTAGAGCTATCATCTTCTCGTGAAAGC  468 seq1  468  GAGTGCCTTCCAAAATATTAAGGACGTCCTTGTCCAGACCTATGATAATATC-GAACAGC  526
              ||||||||||||||||||||||||||||||||||||||||||||||||| |||||||
seq2  469  GA-TGGCTTTAAAGACATTCGAGACGTCTTAGGACAAGTGTATGA-AACAGCTGAAGAGC  526 seq1  527  TTTACAATCGAAAAGGTGAT--ATCA-CGGGAATTCCAACAGGGTTTACGGAGCTTGACC  583
              |||||||||||||||||||  |||| |||||||||||||||||||||||||||||||
seq2  527  TT---GATCAAAATAGTGGTCAAACACCAGTATACCTACAGGATATCGAGATTTAGACC  583 seq1  584  GGATGACTGCGGGTTTCCAGCGCAACTTGATCATTGTGGCTGCCCGTCCTTCAGTAG    643
              ||||||||||||||||||||||||||||||||||||||||||||||||||||||||
seq2  584  AAATGACACAGGGTTCAACGAAAATGATTTAATTATCCTTGCAGCGCGTCCATCTGTAG  643 seq1  644  GGAAAAACAGCCCTTTGCCCGTGAACATCGCACAAAAACGTGGCGAC-----GAAGACCGATG-A  698
              ||||||||||||||||||||||||||||||||||||||||||||||      |||||||||| |
seq2  644  GTAAGACTGCGTTCGCACTTAATATTGCACAAAAAGTTGCAACGCATGAAGA--TATGTA    701 seq1  699  GAGCGTAGCGATTTTCAGTCTTGAGATGGGTGCCGAGCAGCTCGTTATGCGTATGCTCTG  758
              ||||||||||||||||||||||||||||||||||||||||||||||||||||||||||
seq2  702  TACAGTTGGTATTTTCTCGCTAGAGATGGGTGCTGATCAGTAGCCACACGTATGATTTG  761 seq1  759  TGCCCGAGGGAAATATCAATGCCCAGAATC---TCCGTACAGGTAACCTGACCGAAGAGGA  815
              ||||||||||||||||||||||||||||||    ||||||||||||||||||||||||
seq2  762  TAGTTCTGGAAATGT---TGACTCAAACCGCTTAAGAACGGGTACTATGACTGAGGAAGA  818 seq1  816  TTTGGGCAAGCTGACGATGGCAATGGAAGCCTATCGAACAGCGGGATTTACATCGATGA  875
              ||||||||||||||||||||||||||||||||||||||||||||||||||||||||||
seq2  819  TTGGAGTCGTTTTACTATAGCGGTAGTGAATATCACGTACGAAGATTTTTATTGATGA  878 seq1  876  TACACCGGGTATTCGAGTGATTCGACGCCAAGTGCCGCGCTTGAAGCAGGAAAG       935
              ||||||||||||||||||||||||||||||||||||||||||||||||||||||
seq2  879  TACACCGGGTATTCGAATTAATGATTTACGTTCTAAATGTCGTCGATTAAAGCAAGAACA  938
```

```
seq1   936 CGGGCTGGGCATGATTTGATCGATTACCTGCAATTGATTCAGGAAGCGGT----CGTTC     992
           |||  ||| ||||||| || ||| |||| | |||||||||||||||||||    ||| |
seq2   939 TGGCTTAGACATGATTGTGATTGACTACTTACAGTTGATTCAAGGTAGTGTTCACGTGC     998 seq1   993 AAAGGACAACCGTCAGCAGGAAGTATCTGAAATTCCCGTGAACTGAAGTCGATTGCGAG  1052
           |  |||||||||||||||||||||||||||||||  ||||||||||| ||| ||||| 
seq2   999 GTCCGATAACACAGGAAGAAGTTTCTGAAATCTCTGTACATTAAAAGCATTAGCCCG    1058 seq1  1053 GGAGCTGCAAGTCCCTGTTATCGCGTTTCTCAGCTTTCCAGGGTGTTGAGCAGCGTCA   1112
           |||||||||||||| ||||||||| ||| |||| ||||||||| ||||||||  |||
seq2  1059 TGAATTAGAAGTCCAGTTATCGCATTAAGTCAGTTATCTCGTGGTTGTTGAACAACACA  1118 seq1  1113 GGATAAACGTCCGATGATGTCTGATATCCGGAATCAGGAAGTATCGAGCAGGACGCGGA  1172
           ||||||||||||  ||||||| | || |||||||||| |  | |||| | | || || 
seq2  1119 AGATAAACGTCCAATGATGAGTGATATTCGTGAATCTGTGGTTCGATTGAGCAGAGCCGA  1178 seq1  1173 TATTGTCGCGTTCCTTTATCGTGATGACTACT-------------------------ATGA  1208
           || ||| | ||| ||| |  ||||||| |||
seq2  1179 TATCGTTGCATTCTTATACCGTGATGATTACTATAACCGTGGCGGCGATGAAGATGATGA  1238 seq1  1209 CAAAGA---------------AACCGA--GAATAAAA--ATATTATCGAAATTATTAT   1247
                                 |||||   ||||||||   | |  || ||||||| | 
seq2  1239 CGATGATGGTGGTTTCGAGCCACACAACGAATGATGAAAACGTGAAATTGAAATTATCAT  1298 seq1  1248 CGCCAAACAGCGTAACGGCCCGGTAGGAACCGTGTCTCTTGC-GTTCGTAAAAGAATACA  1306
           |||  |||| |||||||| || |  ||   |||     |||| | | ||||||  |||
seq2  1299 TGCTAAGCAACGTAACGGTCCAAACAGGCACAGT-TAAGTTACATTTTATGAAACAATATA  1357 seq1  1307 ACAAATTCGTCAACCTGGAACGGGCGTTTTGATGACGCAGGCGTTCCGCCCCGGCGCA   1362
           | |||||       |  ||| |         ||| |||||  ||     || ||
seq2  1358 ATAAATT-----TACCGATATCG--ATTATGCACATGCAGATATGATG------TAA   1401
```

FIG. 6A-5

SEQ ID NO: 8  DnaC B. subtilis

| | | | | |
|---|---|---|---|---|
| 1 | MTDLLNDRLP | PQNIEAEQAV | LGAIFLQPSA | LTLASEVLIP | DDFYRMSHQK |
| 51 | IYNAMLVLGD | RGEPVDLVTV | TSELANTDLL | EEVGGISYLT | DIANSVPTAA |
| 101 | NIEYYAKIVE | EKSILRRLIR | TATTIAQDGY | TREDEVEDLL | SEAEKTIMEV |
| 151 | AQRKNTSAFQ | NIKDVLVQTY | DNIEQLYNRK | GDITGIPTGF | TELDRMTAGF |
| 201 | QRNDLIIVAA | RPSVGKTAFA | LNIAQNVATK | TDESVAIFSL | EMGAEQLVMR |
| 251 | MLCAEGNINA | QNLRTGNLTE | EDWGKLTMAM | GSLSNSGIYI | DDTPGIRVSE |
| 301 | IRAKCRRLKQ | ESGLGMILID | YLQLIQGSGR | SKDNRQQEVS | EISRELKSIA |
| 351 | RELQVPIAL | SQLSRGVEQR | QDKRPMMSDI | RESGSIEQDA | DIVAFLYRDD |
| 401 | YYDKETENKN | IEIIAKQR | NGPVGTVSLA | FVKEYNKFVN | LERRFDDAGV |
| 451 | PPGA | | | | |

SEQ ID NO: 9  DnaC S. aureus

| | | | | |
|---|---|---|---|---|
| 1 | MDRMYEQNQM | PHNNEAEQSV | LGSIIIDPEL | INTTQEVLLP | ESFYRGAHQH |
| 51 | IFRAMMHLNE | DNKEIDVVTL | MDQLSTEGTL | NEAGGPQYLA | ELSTNVPTTR |
| 101 | NVQYYTDIVS | KHALKRRLIQ | TADSIANDGY | NDELELDAIL | SDAERRILEL |
| 151 | SSSRESDGFK | DIRDVLGQVY | ETAEELDQNS | GQTPGIPTGY | RDLDQMTAGF |
| 201 | NRNDLIILAA | RPSVGKTAFA | LNIAQKVATH | EDMYTVGIFS | LEMGADQLAT |
| 251 | RMICSSGNVD | SNRLRTGTMT | EEDWSRFTIA | VGKLSRTKIF | IDDTPGIRIN |
| 301 | DLRSKCRRLK | QEHGLDMIVI | DYLQLIQGSG | SRASDNRQQE | VSEISRTLKA |
| 351 | LARELECPVI | ALSQLSRGVE | QRQDKRPMMS | DIRESGSIEQ | DADIVAFLYR |
| 401 | DDYYNRGGDE | DDDDDGGFEP | QTNDENGEIE | IIAKQRNGP | TGTVKLHFMK |
| 451 | QYNKFTDIDY | AHADMM | | | |

FIG. 6B-1

```
Sequence 1    SEQ ID NO: 8    DnaC B. subtilis (490 letters)
Sequence 2    SEQ ID NO: 9    DnaC S. aureus (503 letters)

seq1     1  MTDLLNDRLPPQNIEAEQAVLGAIFLQPSALTLASEVLIPDDFYRMSHQKIYNAMLVLGD    60
            :  :        ||||||||: :       |||:: ||   :|: |||
seq2     1  MDRMYEQNQMPHNNEAEQSVLGSIIDPELINTTQEVLLPESFYRGAHQHIFRAMMHLNE    60 seq1    61  RGEPVDLVTVTSELANTDLLEEVGGISYLTDIANSVPTAANIEYYAKIVEEKSILRRLIR   120
              : :||:         :|    ||   :||      ||   |::  ||:  ||::
seq2    61  DNKEIDVVTLMDQLSTEGTLNEAGGPQYLAELSTNVPTTRNVQYYTDIVSKHALKRRLIQ   120 seq1   121  TATTIAQDGYTREDEVEDLLSEAEKTIMEVAQRKNTSAFQNIKDVLVQTYDNIEQLYNRK   180
             |  ||:|||||||||||||||  :::  ||:||||||||||||| |||||:|::|
seq2   121  TADSIANDGYNDELELDAILSDAERRILELSSSRESDGFKDIRDVLGQVYETAEELDQNS   180 seq1   181  GDITGIPTGFTELDRMTAGFQRNDLIIVAARPSVGKTAFALNIAQNVATKTD-ESVAIFS   239
             | ||||||| |:|||||||||||||:||||||||||||||||:|:||||| :|||||:
seq2   181  GQTPGIPTGYRDLDQMTAGFNRNDLIILAARPSVGKTAFALNIAQKVATHEDMYTVGIFS   240 seq1   240  LEMGAEQLVMRMLCAEGNINAQNLRTGNLTEEDWGKLTMAMGSLSNSGIYIDDTPGIRVS   299
            ||||:: ||  ::  ||| :||:|||| |||||| |||  |:|:|||:|||||||||:
seq2   241  LEMGADQLATRMICSSGNVDSNRLRTGTMTEEDWSRFTIAVGKLSRTKIFIDDTPGIRIN   300 seq1   300  EIRAKCRRLKQESGLGMILIDYLQLIQGSG-RSKDNRQQEVSEISRELKSIARELQVPVI   358
             :: || || ||||| ||:|||:||||||| |||:|||||||:||:|| |||:|: ||:
seq2   301  DLRSKCRRLKQEHGLDMIVIDYLQLIQGSGSRASDNRQQEVSEISRTLKALARELECPVI   360 seq1   359  ALSQLSRGVEQRQDKRPMMSDIRESGSIEQDADIVAFLYRDDYYDK--------------   404
            ||||||||||||||||||||||||||||||||||||||||:|
seq2   361  ALSQLSRGVEQRQDKRPMMSDIRESGSIEQDADIVAFLYRDDYYNRGGDEDDDDGFEP    420 seq1   405  ETENKN-IEIIIAKQRNGPVGTVSLAFVKEYNKFVNLERRFDDAGVPPGA            454
             :: || |||||||||||| ||| | || |  |||  ::|| : :
seq2   421  QTNDENGEIEIIIAKQRNGPTGTVVKLHFMKQYNKFTDIDYAHADM-----M          466
```

FIG. 6B-2

Table 1
Similarities in sequence between SEQ ID NO: 2 and sequences deposited in the GenBank database Sequences producing most significant alignments

| | Score (bits) | E Value |
|---|---|---|
| gi|140025|sp|P06567|DNAI_BACSU PRIMOSOMAL PROTEIN DNAI >gi|2797... | 231 | 8e-60 |
| gi|10175766|dbj|BAB06863.1| (AP001517) primosome component (hel... | 220 | 2e-56 |
| gi|468268|gb|AAA22405.1| (M15183) ORFY [Bacillus subtilis] | 125 | 9e-28 |
| gi|2072367|emb|CAA70453.1| (Y09255) primosomal protein DnaI [Ba... | 84 | 2e-15 |
| gi|7481923|pir||S77882 dnaA protein homolog - Mycoplasma capric... | 67 | 3e-10 |
| gi|6537212|gb|AAF15559.1|AF179373_1 (AF179373) putative DNA hel... | 62 | 8e-09 |
| gi|11356757|pir||B82907 conserved hypothetical ATP/GTP-binding ... | 56 | 5e-07 |
| gi|7514782|pir||E70378 DNA replication protein DnaC - Aquifex a... | 52 | 7e-06 |
| gi|1176732|sp|P45910|YQAM_BACSU HYPOTHETICAL 36.1 KD PROTEIN IN... | 50 | 3e-05 |
| gi|9635698|ref|NP_061611.1| orf 21 [Staphylococcus aureus proph... | 48 | 1e-04 |
| gi|1722861|sp|P39782|XKDC_BACSU PHAGE-LIKE ELEMENT PBSX PROTEIN... | 48 | 2e-04 |
| gi|2127076|pir||I40411 PBSX prophage ORF xkdC - Bacillus subtil... | 48 | 2e-04 |

Sequence alignments between Seq ID no 2 and the two first sequences above

```
>gi|140025|sp|P06567|DNAI_BACSU PRIMOSOMAL PROTEIN DNAI
gi|279708|pir||IQBS44 primosome component (helicase loader) dnaI - Bacillus subtilis
gi|39881|emb|CAA28633.1| (X04963) ORF 311 (AA 1-311) [Bacillus subtilis]
gi|1769996|emb|CAA99605.1| (Z75208) replication protein [Bacillus subtilis]
gi|2293281|gb|AAC00359.1| (AF008220) DnaI [Bacillus subtilis]
gi|2635363|emb|CAB14858.1| (Z99118) helicase loader [Bacillus subtilis]
         Length = 311

Score =  231 bits (583), Expect = 8e-60
 Identities = 120/280 (42%), Positives = 177/280 (62%), Gaps = 2/280 (0%)
```

```
Seq 2:   35  DPDVKQFLEAHRAELTNAMIDEDLNVLQEYKDQQKHYDG-HKFADCPNFVKGHVPELYVD  93
             D DV+ FL+ +     MI++ LN L EY +Q K+        +C N ++G+ P+L V+
Sbjct:   31  DQDVQAFLKENEEVIDQKMIEKSLNKLYEYIEQSKNCSYCSEDENCNNLLEGYHPKLVVN  90

Seq 2:   94  NNRIKIRYLQCPCIKYDEERFEAELITSHHMQRDTLNAKLKDIYMNHRDRLDVAMAADD  153
                 I I Y +CP K K D+++   L+ S ++Q+D L A + ++      RL +     D
Sbjct:   91  GRSIDIEYYECPVKRKLDQQKKQQSLMKSMYIQQDLLGATFQQVDISDPSRLAMFQHVTD  150

Seq 2:  154  ICTAITNGEQVKGLYLYGPFGTGKSFILGAIANQLKSKKVRSTIIYLPEFIRTLKGGFKD  213
                +   KGLYLYG FG GK+F+L AIAN+L  K+  S I+Y+PEF+R LK      +D
Sbjct:  151  FLKSYNETGKGKGLYLYGKFGVGKTFMLAAIANELAEKEYSSMIVYPEFVRELKNSLQD  210

Seq 2:  214  GSFEKKLHRVREANILMLDDIGAEEVTPWVRDEVIGPLLHYRMVHELPTFFSSNFDYSEL  273
             + E+KL+       V+      +LMLDDIGAE +T WVRDEVIG +L +RM  +LPTFFSSNF     EL
Sbjct:  211  QTLEEKLNMVKTTPVLMLDDIGAESMTSWVRDEVIGTVLQHRMSQQLPTFFSSNFSPDEL  270

Seq 2:  274  EHHLAMTRDGE-EKTKAARIIERVKSLSTPYFLSGENFRN  312
             +HH        ++ GE E+ KAAR++ER+  L+ P  L GEN R+
Sbjct:  271  KHHFTYSQRGEKEEVKAARLMERILYLAAPIRLDGENRRH  310
```

>gi|10175766|dbj|BAB06863.1| (AP001517) primosome component
(helicase loader) [Bacillus halodurans]
Length = 311

Score = 220 bits (554), Expect = 2e-56
Identities = 114/281 (40%), Positives = 176/281 (62%), Gaps = 6/281 (2%)

```
Seq 2:   36  PDVKQFLEAHRAELTNAMIDEDLNVLQEYKDQQKHYDGH--KFADCPNFVKGHVPELYVD  93
             P V+ FLE H + L+    +++ L+ EY+ +Q H    H       CPN +KG+ P LYV+
Sbjct:   32  PHVQLFLEEHPS-LSPITLEQGLSKLYEYQKEQSHC-AHCPGLQKCPNLMKGYQPTLYVE  89
```

```
Seq 2:   94  NNRIKIRYLQCPCKIKYDEERFEAELITSHHMQRDTLNAKLKDIYMNHRDRLDVAMAADD  153
             + +++ Y  CP K + + E+ +   LI S ++ ++ L AK  D+  +  R   A +
Sbjct:   90  RDSLELSYSPCPLKEEEEREKKKRSLIRSLYIPKEILEAKFDDVE-SEPGRSIASHRALE  148

Seq 2:  154  ICTAITNGEQVKGLYLYGPFGTGKSFILGAIANQLKSKKVRSTIIYLPEFIRTLKGGFKD  213
                  GE   GLYLYG FG GK+F++GAIAN+LK + +   STI+Y+P+F R LK     D
Sbjct:  149  FALSAKPGEDGMGLYLYGKFGVGKTFLMGAIANELKDRGIDSTIVYVPDFFRELKQSIGD  208

Seq 2:  214  GSFEKKLHRVREANILMLDDIGAEEVTPWVRDEVIGPLLHYRMVHELPTFFSSNFDYSEL  273
             G+F++KL  V+ A +L+ DDIGAE +T WVRD+V+G +L YR++ +LPT F+SN+DY EL
Sbjct:  209  GTFQQKLDFVKNAQVLIFDDIGAETMTSWRDDVLGVILQYRIMEKLPTLFTSNYDYDEL  268

Seq 2:  274  EHHLAMT-RDGEEKTKAARIIERVKSLSTPYFLSGENFRNN  313
             E HLA    + G E  KA R++ER++  +    G+N R +
Sbjct:  269  EEHLAYNDKSGTELLKAKRVMERIRHYTVSVMVQGQNRREH  309
```

FIG. 6B-5

YEAST TWO-HYBRID ASSAY
C-
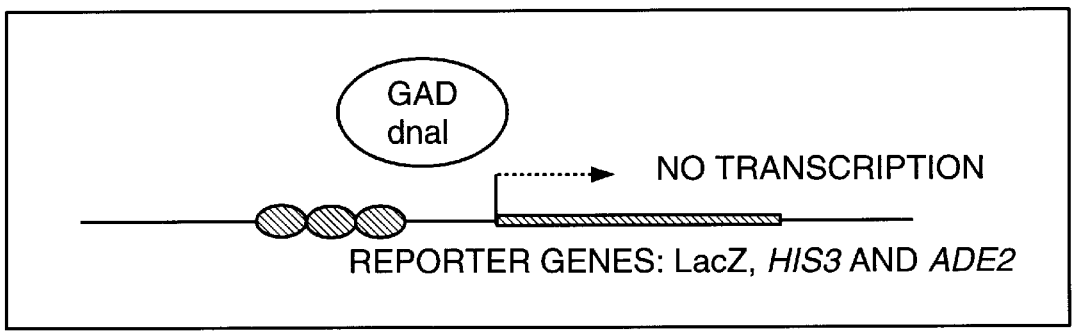
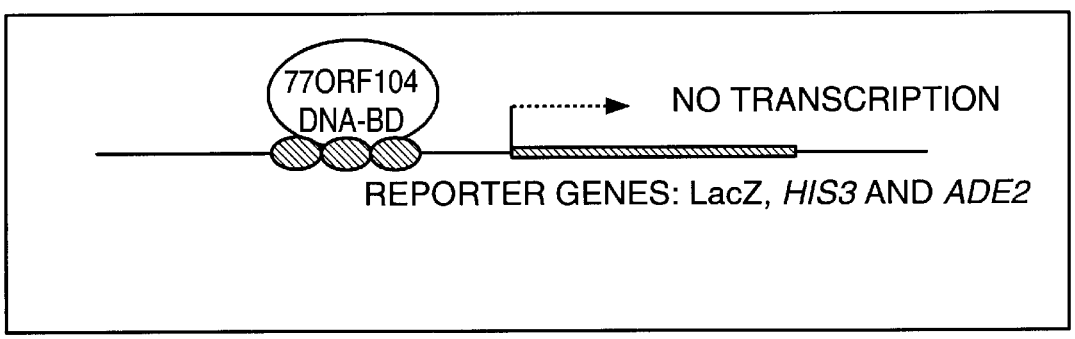
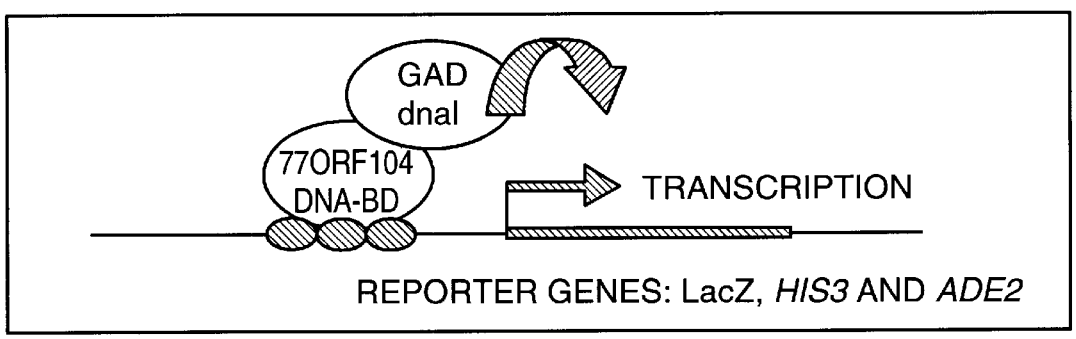
FIG. 12C

Results of growth of yeast co-transformed with the indicated
two plasmids (from 1 to 6 below) on selective plates.

SD: Synthetic medium, Trp: tryptophan,
Leu: leucine, His: histidine, Ade: adenine

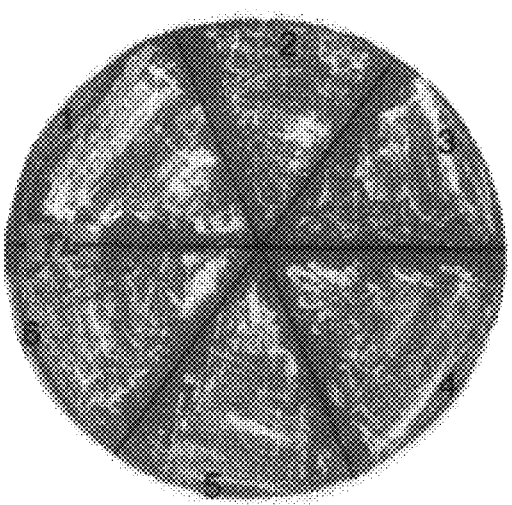
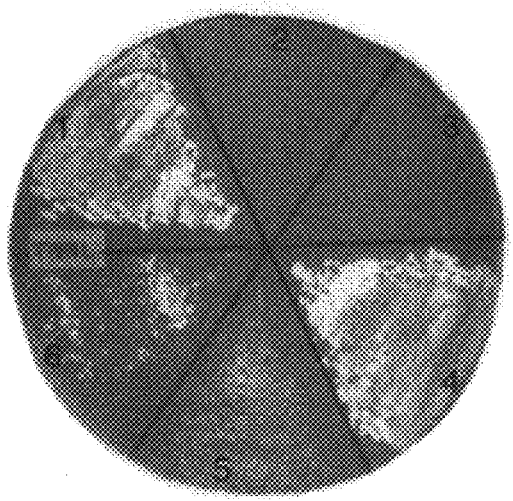

SD plate without Trp and Leu

SD plate without Trp, Leu, His and Ade 1) pGBKT7-53 and pGADT7-T
2) pGBKT7-53 and pGAD dnaI
3) pGBK77ORF104 and pGADT7-T
4) pGBKT7-LAM and pCL1
5) pGBK77ORF104 and pGAD dnaI
5) pGBK dnaI and pGAD77ORF104

FIG. 12D

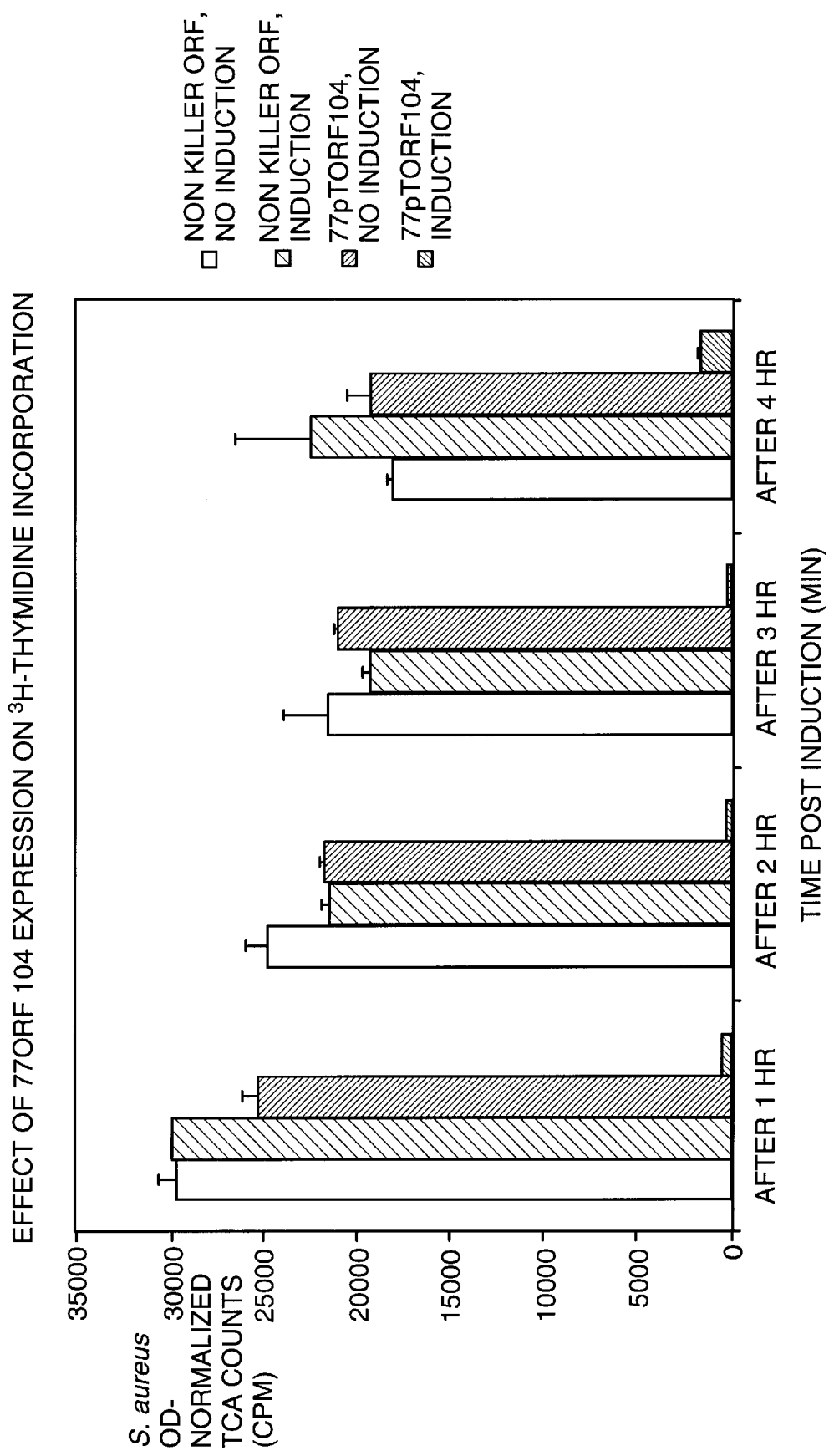

COMPOSITIONS AND METHODS INVOLVING AN ESSENTIAL *STAPHYLOCOCCUS AUREUS* GENE AND ITS ENCODED PROTEIN

This Application claims Priority under 35 U.S.C. Section 119 from U.S. Patent Application No. 60/110,992 filed Dec. 3, 1998 and is a Continuation-In-Part under 35 U.S.C. Section 120 of U.S. patent application Ser. No. 09/407,804 filed Sep. 28, 1999.

FIELD OF THE INVENTION

The invention relates to bacterial and bacteriophage genes.

BACKGROUND OF THE INVENTION

The Staphylococci make up a medically important genera of microbes known to cause several types of diseases in humans. *S. aureus* is a Gram positive organism which can be found on the skin of healthy human hosts. It is responsible for a large number of bacteremias, where its portal of entry can be the skin, lungs, urinary tract or infected intravascular devices (Steinberg et al., (1996)) Clin. Infect. Dis. 23: 255–259; Røder et al., (1999) Arch. Intern. Med. 159: 462–469). It can cause fatal endocarditis or damage to the heart and, due to its exotoxin, can cause death via "Toxic Shock" (Frimodt-Møller et al., (1997) Clin. Microbiol. Infect. 3: 297–305; Sanabria et al., (1990) Arch. Intern. Med. 150: 1305–1309).

Only *S. aureus* and *Staphylococcus epidermidis*, of the nineteen species of Staphylococcus described in Bergey's Manual (1992), have significant interactions with humans. They are among the normal flora of humans, and are found on nasal passages, skin and mucous membranes. *S. aureus*, when pathogenic in humans, can cause a number of suppurative (pus-forming) infections, as well as food poisoning, endocarditis, and toxic shock syndrome.

*S. aureus* causes superficial skin lesions, such as boils, styes and furunculosis; more serious infections such as pneumonia, mastitis, phlebitis, meningitis, and urinary tract infections, in addition to osteomyelitis and endocarditis. *S. aureus* is also a major cause of hospital acquired (nosocomial) infection of surgical wounds and infections associated with inserted and implanted medical devices. Lastly, *S. aureus* causes food poisoning through the release of enterotoxins into food, and toxic shock syndrome through the release of superantigens into the blood stream. *S aureus* also secretes two types of toxin with superantigen activity: 1) enterotoxins, of which there are six antigenic types (named SE-A, B, C, D, E and G) and 2) toxic shock syndrome toxin (TSST-1).

*S. aureus* has been successfully treated with the penicillin derivative Methicillin in the past, but is now becoming increasingly resistant (MRSA—Methicillin Resistant *S. aureus*) to this antibiotic (Harbath et al., (1998) Arch. Intern. Med. 158: 182–189.). For example, *S. aureus* endocarditis mortality can range from 26–45%, and combined β-lactam/ aminoglycoside therapy is proving increasingly ineffective in disease eradication (Røder et al., (1999) Arch. Intern. Med. 159: 462–469). However, MRSA infections continued to be sensitive to treatment with vancomycin which is the drug of last resort. Infections caused by MRSA have been increasing in children and adults; isolates have been found in 97% of all large, university-based teaching hospitals in the United States. Since 1996, three cases of vancomycin resistant *S. aureus* have been reported. This new strain represents a particularly dangerous development of an aggressive bacterial pathogen which does not respond to any known antibiotic. The emergence of resistance to vancomycin has the potential to result in untreatable (and thus fatal) *S. aureus* infections.

It is no longer uncommon to isolate *S. aureus* strains which are resistant to most of the standard antibiotics, and thus there is an unmet medical need and demand for new anti-microbial agents, vaccines, drug screening methods, and diagnostic tests for this organism.

SUMMARY OF THE INVENTION

The present invention relates to dnaI and dnaI related proteins, in particular *S. aureus* DnaI polypeptides and dnaI polynucleotides, recombinant materials and methods for their production. The invention also relates to a pair of interacting proteins, a growth-inhibitory (or killer) bacteriophage P77 ORF 104 gene product that interacts with the *S. aureus* DnaI polypeptide, the interacting regions of the *S. aureus* DnaI related protein and the protein encoded by the *S. aureus* bacteriophage 77 ORF 104, forming the basis for screening assays. It also relates to polynucleotides and polypeptides of a multiprotein complex believed to be involved in initiation of DNA replication containing DnaI as a subunit, and also may include DnaC and related proteins, as well as variants of them. In another aspect, the invention relates to methods for using such polypeptides and polynucleotides, including treatment of microbial diseases, amongst others. In a further aspect, the invention relates to methods for identifying agonists and antagonists using the materials provided by the invention, and for treating microbial infections and conditions associated with such infections with the identified agonist or antagonists compounds. In a still further aspect, the invention relates to diagnostic assays for detecting diseases associated with microbial infections and conditions associated with such infections, such as assays for detecting dnai expression or activity.

The invention encompasses a method of identifying a compound that is active on a *S. aureus* DnaI polypeptide, comprising contacting a candidate compound with the DnaI polypeptide, and detecting binding of the candidate compound to the DnaI polypeptide, wherein detection of binding is indicative that the compound that is active on the DnaI polypeptide.

In one embodiment, the step of detecting comprises the step of measuring the binding of a candidate compound, wherein the compound is directly or indirectly detectably labeled, to the DnaI polypeptide.

In another embodiment, the step of detecting comprises measurement by surface plasmon resonance.

In another embodiment, the step of detecting comprises measurement by FRET.

In another embodiment, the step of detecting comprises measurement of fluorescence polarization changes.

In another embodiment, the step of detecting comprises a scintillation proximity assay.

In another embodiment, the step of detecting comprises a biosensor assay.

The invention further encompasses a method of identifying a compound that is active on a DnaI polypeptide, comprising the steps of contacting a candidate compound with cells expressing a DnaI polypeptide and detecting DnaI polypeptide activity in the cells, wherein a decrease in activity relative to DnaI activity in cells not contacted with a candidate compound is indicative of inhibition of DnaI activity.

In one embodiment, the step of detecting comprises measuring the incorporation of $^3$H-thymidine into DNA.

In another embodiment, the step of detecting comprises measuring plasmid replication.

The invention further encompasses an agonist or an antagonist of the activity of a DnaI polypeptide or a gene encoding the polypeptide.

The invention further encompasses a method of identifying a compound that is active on a polypeptide complex comprising a S. aureus DnaI polypeptide and a polypeptide of S. aureus DnaC, the method comprising: providing the polypeptide complex and a candidate compound; and detecting an increase or decrease in the amount of the complex in the presence of the candidate compound, wherein an increase or decrease in the amount in the presence of the candidate compound relative to its absence is indicative of a compound that is active on the complex.

In one embodiment, the providing step comprises permitting said polypeptide complex to form in the presence of the candidate compound.

The invention further encompasses a method of making an antibacterial compound, comprising the steps of: i) determining whether a candidate compound is active on a DnaI polypeptide or a gene encoding the polypeptide; and ii) synthesizing or purifying the candidate compound in an amount sufficient to provide a therapeutic effect when administered to an organism infected by a bacterium naturally producing the polypeptide.

In one embodiment, the candidate compound is selected from the group consisting of a small molecule, a peptidomimetic compound, and a fragment or derivative of a bacteriophage inhibitor protein.

The invention further encompasses a method for inhibiting a bacterium, comprising contacting the bacterium with a compound active on a S. aureus DnaI polypeptide or a gene encoding the polypeptide.

In one embodiment, the step of contacting is performed in vitro.

In another embodiment, the step of contacting is performed in vivo in an animal.

The invention further encompasses a method for treating a bacterial infection in an animal suffering from an infection, comprising administering to the animal a therapeutically effective amount of a compound active on a S. aureus DnaI polypeptide or a gene encoding the polypeptide.

In one embodiment, the compound is selected from the group consisting of a small molecule, a peptidomimetic compound, and a bacteriophage inhibitor protein.

The invention further encompasses a method of prophylactic treatment to prevent bacterial infection comprising contacting an indwelling device with a compound active on a S. aureus DnaI polypeptide before its implantation into a mammal, such contacting being sufficient to prevent S. aureus infection at the site of implantation.

The invention further encompasses a method of prophylactic treatment to prevent infection of an animal by a bacterium comprising administering to the animal a compound that is active on a S. aureus DnaI polypeptide or a gene encoding the polypeptide in an amount sufficient to reduce adhesion of the bacterium to a tissue surface of a tissue of the mammal.

The invention further encompasses a method of diagnosing in an individual an infection with Staphylococcus aureus, comprising: determining the presence in the individual of a S. aureus DnaI polypeptide.

In one embodiment, the determining step comprises contacting a biological sample of the individual with an antibody specific for an epitope present on a S. aureus DnaI polypeptide.

The invention further encompasses a method of diagnosing in an individual an infection with Staphylococcus aureus, comprising: determining the presence in the individual of a nucleic acid sequence encoding a S. aureus DnaI polypeptide.

In one embodiment, the determining step comprises contacting a nucleic acid sample of said individual with an isolated, purified or enriched nucleic acid probe of at least 15 nucleotides in length that hybridizes under stringent hybridization conditions with the sequence of SEQ ID NO:1, or the complement of such probe.

The invention further encompasses an isolated, purified or enriched polynucleotide comprising a nucleotide sequence that has at least 60% identity to the sequence of SEQ ID NO:1, or the complement of said nucleotide sequence.

The invention further encompasses an isolated, purified or enriched polynucleotide comprising a nucleotide sequence encoding the polypeptide of SEQ ID NO:2, or the complement of such nucleotide sequence.

The invention further encompasses an isolated, purified or enriched polynucleotide comprising the polynucleotide of SEQ ID NO:1, or the complement of said polynucleotide of SEQ ID NO:1.

The invention further encompasses an isolated, purified or enriched polynucleotide of at least 15 nucleotides in length having at least 80% identity to a sequence selected from the group consisting of nucleotides 1–113, 101–496, 484–529, 518–538, 526–548, 551–606, 596–614, 602–693, 694–736, 736–791, 780–794, and 791–942, inclusive, of SEQ ID NO:1, or the complement of such a nucleotide sequence.

The invention further encompasses an isolated, purified or enriched polynucleotide of at least 16 nucleotides in length having at least 81% identity to a sequence selected from the group consisting of nucleotides 1–530, 517–549, 540–555, 550–607, 595–694, 693–737, 729–744, 735–795, and 790–942, inclusive, of SEQ ID NO:1, or the complement of such a nucleotide sequence.

The invention further encompasses an isolated, purified or enriched polynucleotide of at least 16 nucleotides in length having at least 75% identity to a sequence selected from the group consisting of nucleotides 1–68, 55–103, 90–111, 102–122, 112–496, 484–502, 489–529, 519–538, 528–543, 530–547, 551–603, 597–613, 602–691, 697–736, 736–790, 791–828, 816–832, and 820–942, inclusive, of SEQ ID NO:1, or the complement of such a nucleotide sequence.

The invention further encompasses an isolated, purified or enriched polynucleotide of at least 17 nucleotides in length having at least 76% identity to a sequence selected from the group consisting of nucleotides 1–112, 99–115, 101–123, 111–530, 518–540, 527–548, 550–604, 596–614, 600–692, 696–737, 735–791, 777–794, 790–829, 815–833, and 819–942, inclusive, SEQ ID NO:1, or the complement of such a nucleotide sequence.

The invention further encompasses an isolated, purified or enriched polynucleotide of at least 17 nucleotides in length having at least 70% identity to a sequence selected from the group consisting of nucleotides 1–68, 56–97, 83–100, 86–103, 91–107, 102–121, 113–200, 186–496, 485–501, 489–521, 507–526, 512–529, 551–598, 584–601, 587–603, 602–691, 697–718, 704–736, 740–757, 743–767, 753–790, 791–828, 816–832, 820–877, and 863–942, inclusive, SEQ ID NO:1, or the complement of such a nucleotide sequence.

The invention further encompasses an isolated, purified or enriched nucleic acid probe of at least 15 nucleotides in length that hybridizes under stringent hybridization conditions with the sequence of SEQ ID NO:1, or the complement of the probe.

The invention further encompasses an isolated, purified or enriched polynucleotide consisting of the sequence of SEQ ID NO:1.

The invention further encompasses an isolated, purified or enriched polypeptide having at least 50% identity to the amino acid sequence of SEQ ID NO:2.

The invention further encompasses an isolated, purified or enriched polypeptide of at least 5 amino acids in length having at least 80% identity to a sequence selected from the group consisting of amino acids 1–23, 21–167, 171–176, 174–184, 185–202, 200–204, 202–231, 235–243, 247–262, 266–275, 273–290, 289–308, 306–310, and 308–313, inclusive, of SEQ ID NO:2.

The invention further encompasses an isolated, purified or enriched polypeptide of at least 6 amino acids in length having at least 66% identity to a sequence selected from the group consisting of amino acids 1–23, 22–41, 38–62, 60–108, 105–167, 175–180, 177–183, 185–201, 204–231, 236–243, 248–262, 266–275, 273–289, 291–308, and 308–313, inclusive, of SEQ ID NO:2.

The invention further encompasses an isolated, purified or enriched polypeptide of at least 6 amino acids in length having at least 83% identity to a sequence selected from the group consisting of amino acids 1–168, 170–185, 182–187, 184–232, 234–244, 246–263, and 265–313, inclusive, of SEQ ID NO:2.

The invention further encompasses an isolated, purified or enriched polypeptide of at least 7 amino acids in length having at least 57% identity to a sequence selected from the group consisting of amino acids 1–23, 22–28, 24–37, 33–40, 38–58, 54–62, 60–66, 62–68, 64–104, 100–106, 102–108, 106–131, 127–167, 186–200, 204–222, 218–231, 248–260, 268–275, 273–288, and 291–307, inclusive, of SEQ ID NO:2.

The invention further encompasses an isolated, purified or enriched polypeptide of at least 7 amino acids in length having at least 71% identity to a sequence selected from the group consisting of amino acids 1–25, 21–63, 59–168, 172–178, 174–184, 184–202, 198–204, 200–206, 203–232, 235–244, 247–263, 265–290, 286–293, 290–310, and 306–313, inclusive, SEQ ID NO:2.

The invention further encompasses an isolated, purified or enriched polypeptide of at least 8 amino acids in length having at least 50% identity to a sequence selected from the group consisting of amino acids 1–23, 24–37, 33–40, 38–58, 55–62, 64–91, 86–103, 106–131, 127–167, 186–200, 204–219, 214–222, 218–231, 250–260, 273–288 and 291–307, inclusive SEQ ID NO:2.

The invention further encompasses an isolated, purified or enriched polypeptide of at least 8 amino acids in length having at least 62% identity to a sequence selected from the group consisting of amino acids 1–25, 21–41, 36–63, 59–110, 105–168, 175–182, 185–201, 203–232, 247–261, 267–289, 286–293, 290–308, 303–310, and 306–313, inclusive, of SEQ ID NO: 2.

The invention further encompasses an isolated, purified or enriched polypeptide of at least 8 amino acids in length having at least 75% identity to a sequence selected from the group consisting of amino acids 1–169, 172–185, 180–187, 182–207, 202–233, 234–245, 246–264, 264–294, and 289–313, inclusive, of SEQ ID NO:2.

The invention further encompasses an isolated, purified or enriched polypeptide having at least 70% similarity to the amino acid sequence of SEQ ID NO:2.

The invention further encompasses an isolated, purified or enriched polypeptide of at least 20 amino acids in length having at least 60% similarity to the amino acid sequence of SEQ ID NO:2.

The invention further encompasses an isolated, purified or enriched polypeptide of at least 9 amino acids in length having at least 44% sequence similarity to a sequence selected from the group consisting of amino acids 2–11, 8–21, 43–54, 65–80, 94–102, and 141–166, inclusive, of SEQ ID NO:2.

The invention further encompasses an isolated, purified or enriched polypeptide of at least 10 amino acids in length having at least 50% sequence similarity to a sequence selected from the group consisting of amino acids 1–13, 6–22, 42–55, 64–82, 91–100, 93–103, 129–138, 133–143, 140–167, and 297–306, inclusive, of SEQ ID NO:2.

The invention further encompasses an isolated, purified or enriched polypeptide of at least 20 amino acids in length having at least 50% sequence similarity to a sequence selected from the group consisting of amino acids 1–23, 57–84, 68–87, and 129–170, inclusive, of SEQ ID NO:2.

The invention further encompasses an isolated, purified or enriched polypeptide of at least 20 amino acids in length having at least 60% sequence similarity to a sequence selected from the group consisting of amino acids 1–27, 32–55, 38–66, 54–91, 87–106, 89–113, 115–134, 117–136, 123–175, 208–228, and 268–288, inclusive, of SEQ ID NO:2.

The invention further encompasses an isolated, purified or enriched polypeptide of at least 20 amino acids in length having at least 70% sequence similarity to a sequence selected from the group consisting of amino acids 1–30, 29–127, 110–129, 112–178, 192–212, 203–230, 263–290, 285–290, 287–306, and 291–313, inclusive, of SEQ ID NO:2.

The invention further encompasses an isolated, purified or enriched polypeptide of at least 25 amino acids in length having at least 48% sequence similarity to a sequence selected from the group consisting of amino acids 127–173, inclusive, of SEQ ID NO:2.

The invention further encompasses an isolated, purified or enriched polypeptide of at least 25 amino acids in length having at least 60% sequence similarity to a sequence selected from the group consisting of amino acids 1–28, 33–58, 36–60, 38–98, 76–100, 86–111, 91–115, 93–119, 114–139, and 117–178, inclusive, of SEQ ID NO:2.

The invention further encompasses an isolated, purified or enriched polypeptide of at least 25 amino acids in length having at least 68% sequence similarity to a sequence selected from the group consisting of amino acids 1–32, 10–34, 27–126, 105–180, 158–182, 187–214, 192–217, 202–233, 263–293, 277–301, and 282–306, inclusive, of SEQ ID NO:2.

The invention further encompasses an isolated polypeptide comprising the amino acid sequence of SEQ ID NO:2.

The invention further encompasses an isolated polypeptide consisting of the amino acid sequence of SEQ ID NO:2.

The invention further encompasses an isolated, purified or enriched antibody specific for a polypeptide of the invention.

The invention further encompasses a composition comprising two polypeptides, a bacteriophage P77 ORF 104-encoded polypeptide and a *S. aureus* DnaI polypeptide.

The invention further encompasses a composition comprising at least three polypeptides, a bacteriophage P77 ORF 104-encoded polypeptide, a *S. aureus* DnaI polypeptide and a *S. aureus* DnaC polypeptide.

The invention further encompasses a composition comprising at least two polypeptides, a *S. aureus* DnaI polypeptide and a *S. aureus* DnaC polypeptide.

The invention further encompasses a composition comprising two nucleic acid sequences, bacteriophage P77 ORF 104 and *S. aureus* dnaI nucleic acid sequence.

The invention further encompasses a composition comprising at least two nucleic acid sequences, a *S. aureus* dnaI nucleic acid sequence and a *S. aureus* dnaC nucleic acid sequence.

The invention further encompasses a composition comprising at least three nucleic acid sequences, bacteriophage P77 ORF 104 nucleic acid sequence, a *S. aureus* dnaI nucleic acid sequence, and a *S. aureus* dnaC nucleic acid sequence.

Further features and advantages of the invention will become more fully apparent in the following description of the embodiments and drawings thereof, and from the claims.

BRIEF DESCRIPTION OF THE DRAWINGS

FIGS. 1A–1B show the nucleotide (A; SEQ ID NO:1) and amino acid (B; SEQ ID NO:2) sequences of *S. aureus* DnaI.

Figure 2J:
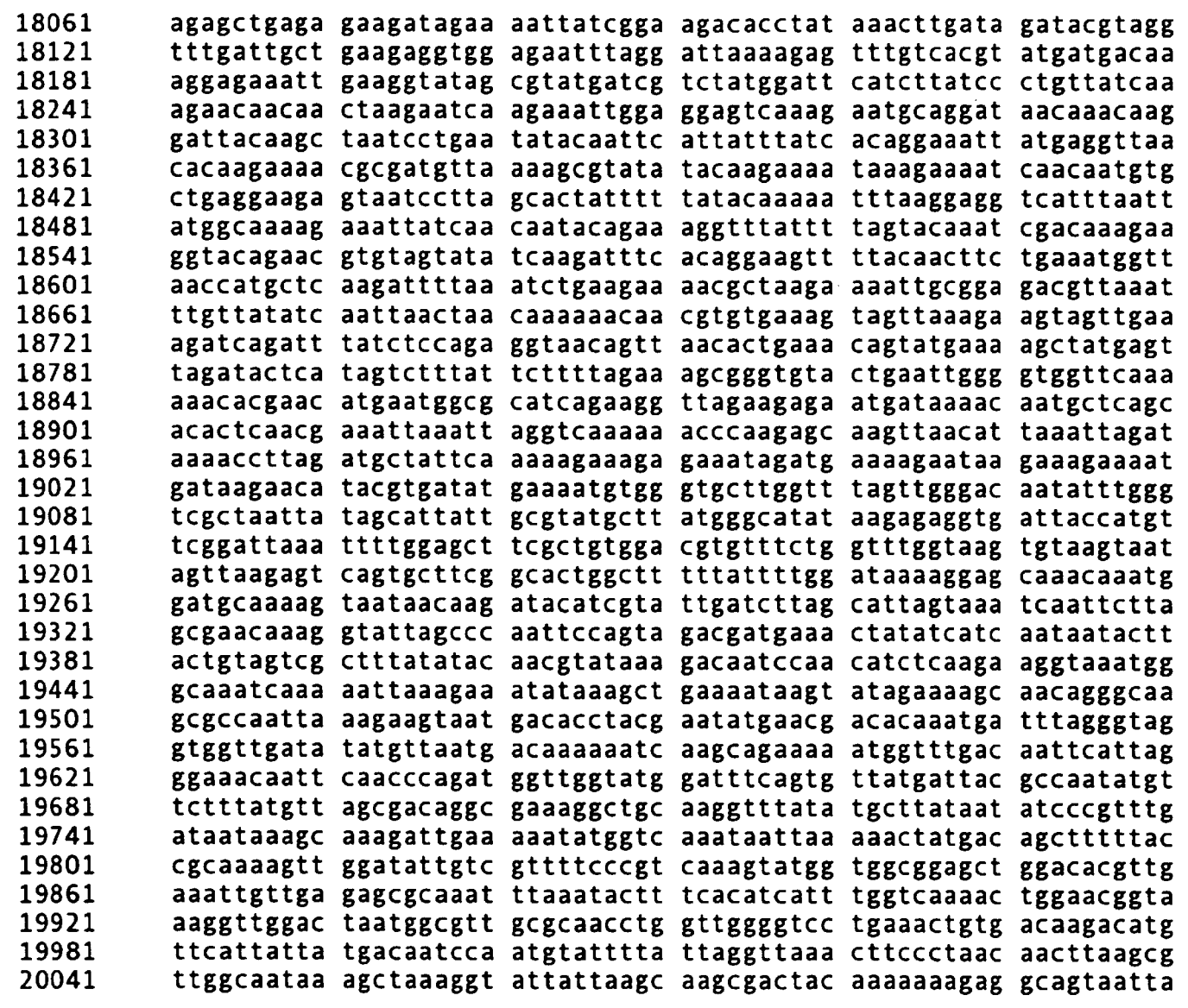
Figure 2K:
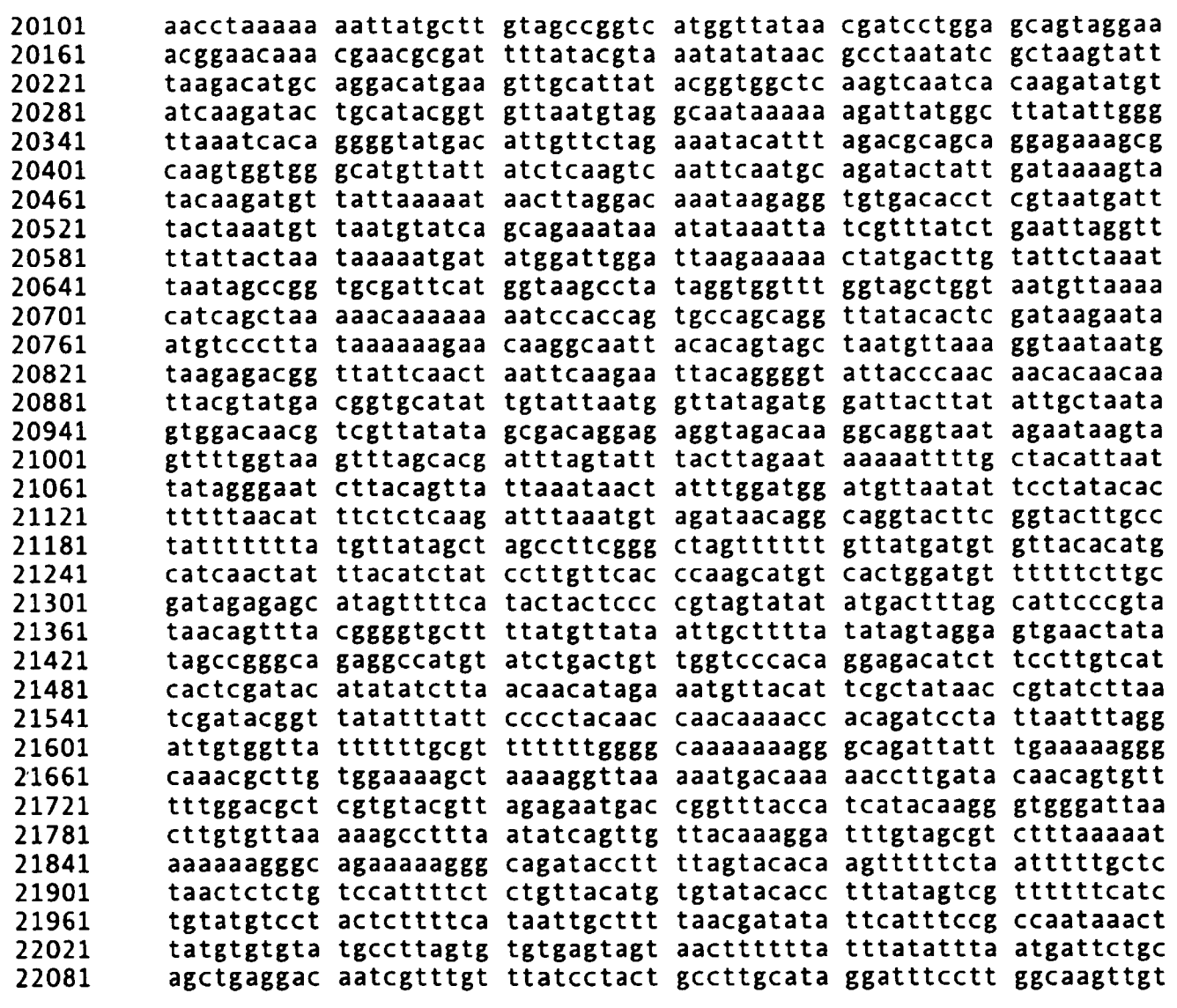
Figure 2N:
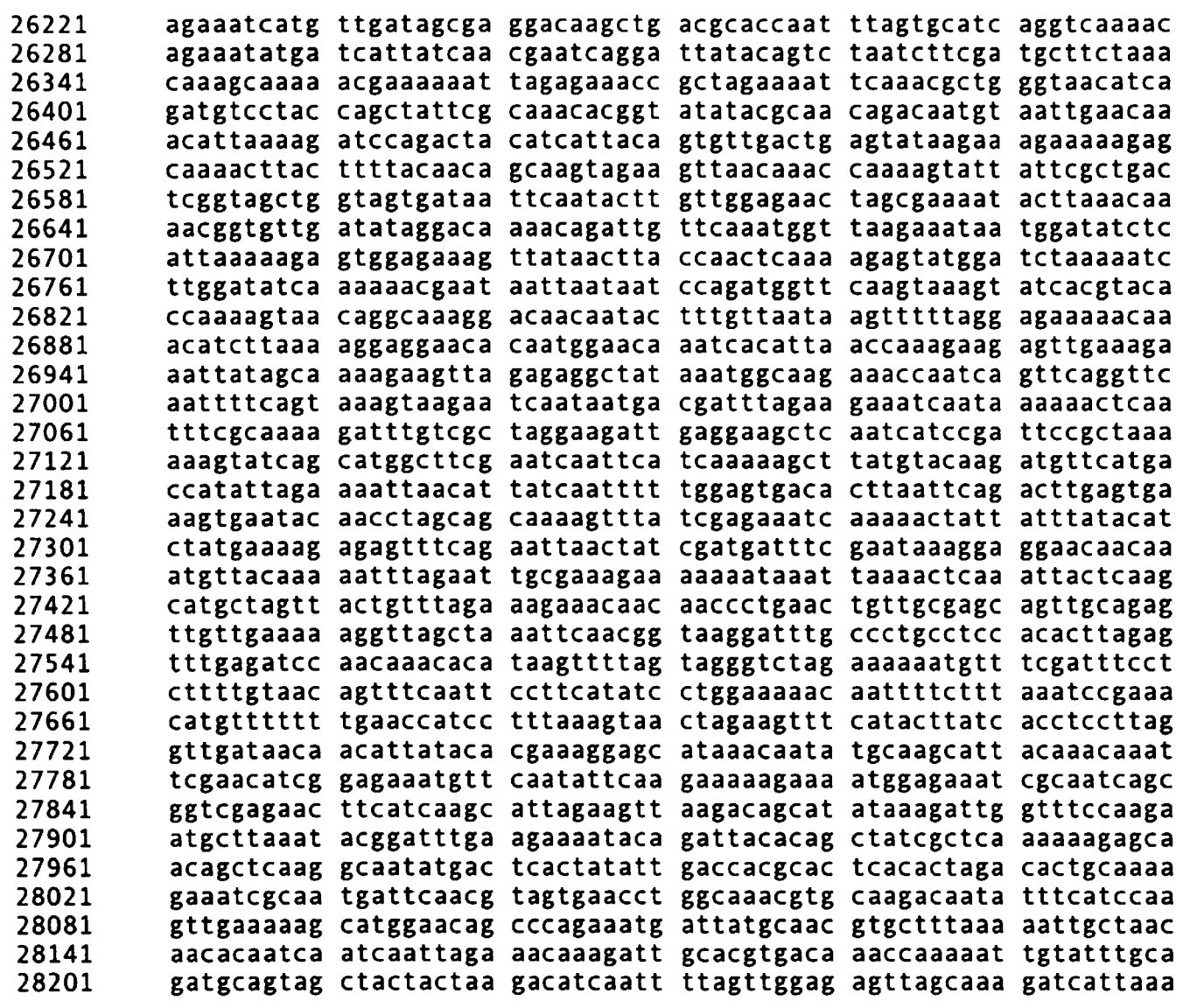
Figure 2R:
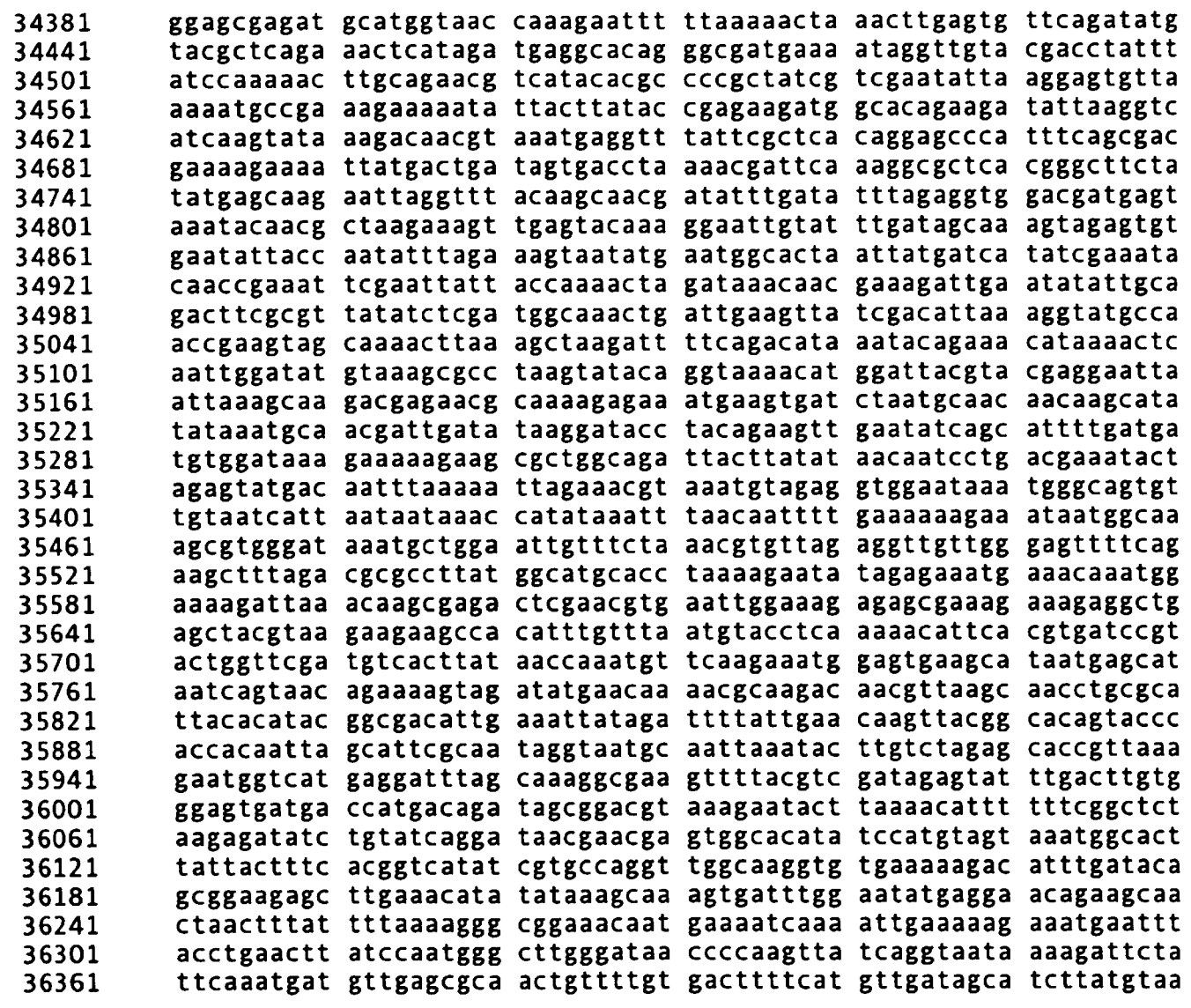

FIG. 2 shows the complete nucleotide sequence of the *S. aureus* bacteriophage 77 genome (SEQ ID NO:3).

FIGS. 4A–4B shows A) the nucleotide (SEQ ID NO:4) and B) the amino acid (SEQ ID NO:5) sequences of *S. aureus* Bacteriophage P77 ORF 104.

FIG. 5 shows the predicted tryptic peptide masses of the ORF (SED iD NO: 10–13) identified in the University of Oklahoma *S aureus* genomic database that closely matches the tryptic peptide profile of the polypeptide bound by P77ORF104.

FIGS. 6A–6B shows alignments of *B. subtilis* DnaC sequences with the homologous sequences from *S. aureus*. FIG. 6A shows an alignment of *B. subtilis* dnaC polynucleotide sequence (SEQ ID NO:6) with the homologous *S. aureus* dnaC polynucleotide sequence (SEQ ID NO:7) identified by BLAST searching the *S. aureus* database at http://www.tigr.org with the *B. subtilis* dnaC sequence. FIG. 6B shows an alignment of *B. subtilis* DnaC amino acid sequence (SEQ. ID NO:8) with the predicted amino acid sequence of the polypeptide (SEQ ID NO:9) encoded by the *S. aureus* dnaC polynucleotide sequence shown in FIG. 6A.

FIGS. 12A–12E shows the results of yeast two hybrid analyses designed to test the interaction of *S. aureus* DnaI and P77 ORF 104. FIG. 12A shows the construction of the yeast pGADT7 vector expressing the fusion protein Gal4 activation domain (GAD) and *S. aureus* DnaI homolog. FIG. 12B shows the construction of the yeast pGBKT7 vector expressing the fusion protein Gal4 binding domain (GBD) and phage 77 ORF104. FIG. 12C shows a schematic of the yeast two-hybrid assay. FIG. 12D shows the results of yeast co-transformants plated on selective plates containing minimal synthetic medium (SD), without tryptophan (Trp), leucine (Leu), histidine (His) or adenine (Ade). FIG. 12E shows the results of luminescent β-galactosidase assays with the yeast co-transformants. The list of 1–6 at the bottom of FIG. 12D indicates each two-plasmid combination co-transformed in the spaces/columns indicated by numbers 1–6 in FIGS. 12D and 12E.

FIG. 13 shows inhibition of *S. aureus* DNA synthesis by bacteriophage 77 ORF 104 protein.

DESCRIPTION OF THE INVENTION

Figure 3:
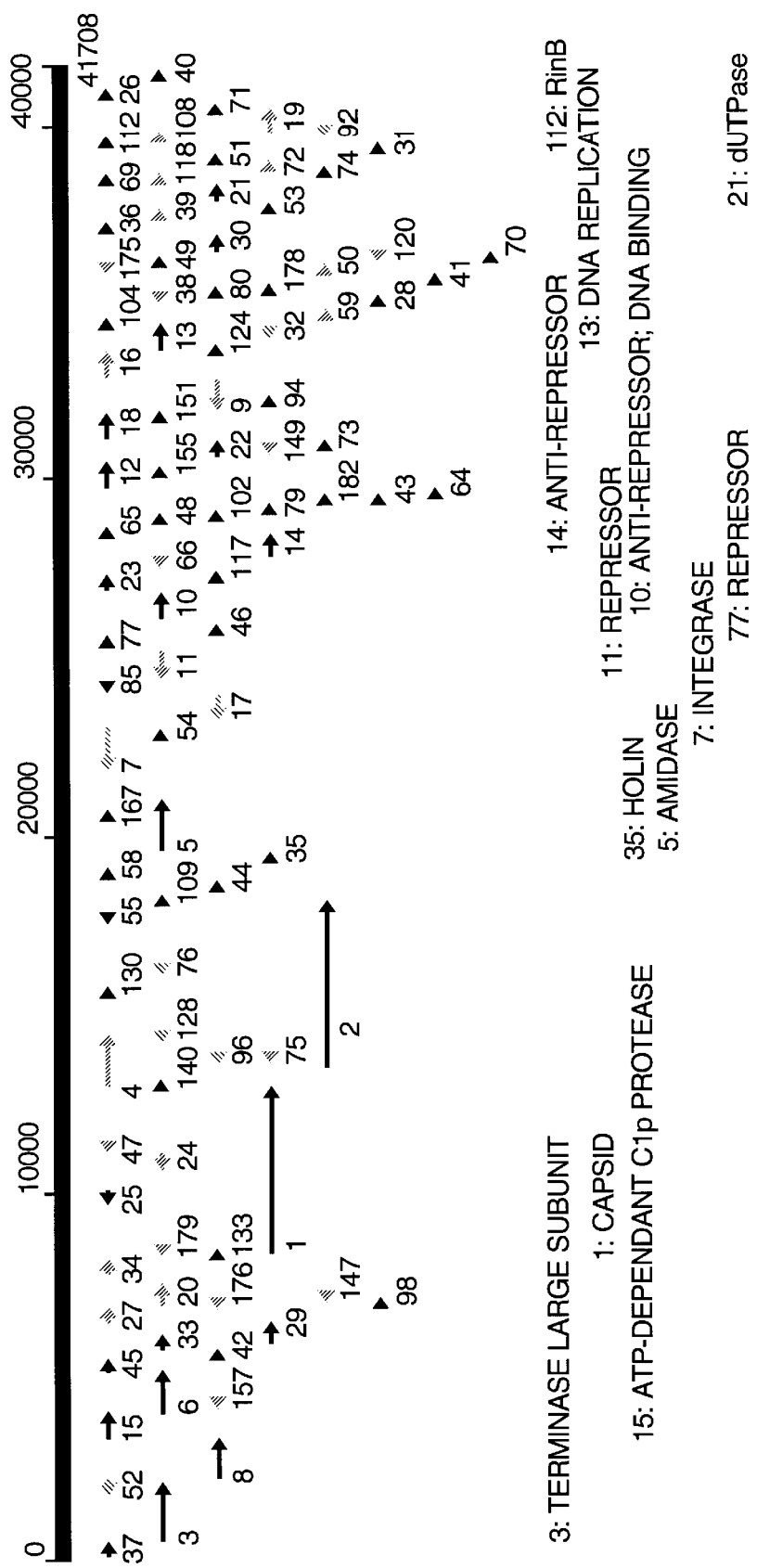
FIG. 3 shows an ORF map of the *S. aureus* bacteriophage 77 genome.

The invention is based on the discovery of an essential gene and its encoded polypeptide in *S. aureus* and portions thereof useful in screening, diagnostics, and therapeutics. The invention also relates to *S. aureus* DnaI polypeptides and polynucleotides as described in greater detail below, and to a pair of polynucleotides encoding a pair of interacting polypeptides, and the pair of polypeptides themselves, or interacting domains thereof, where the pair includes an *S. aureus* DnaI polypeptide and a P77 ORF 104 polypeptide. Also, the invention relates to polynucleotides and polypeptides of a protein complex, thought to be involved in initiation of DNA replication, containing DnaI and DnaC related proteins, as well as their variants. In particular, the invention relates to polypeptides and polynucleotides of a DnaI of *S. aureus*, which is related by amino acid sequence homology to *B. subtilis* DnaI polypeptide. The invention relates especially to DnaI having the nucleotide and amino acid sequences disclosed as SEQ ID NO:1 and SEQ ID NO:2, respectively. The sequences presented as SEQ ID NOs: 1 and 2 represent an exemplification of the invention, since those of ordinary skill will recognize that such sequences can be usefully employed in polynucleotides in general, including ribopolynucleotides.

We have used the methodology of two previous inventions (U.S. Provisional Patent Application Serial No. 09/407.804, filed Sep. 28, 1999, and U.S. Provisional Patent Application 60/110,992 filed Dec. 3, 1998) to identify and characterize an essential polynucleotide and polypeptide sequence from *S. aureus* . Thus, the present invention provides polynucleotide and polypeptide sequences isolated from *S. aureus* which can be used in a drug screening assay to identify compounds with anti-microbial activity. The polynucleotide and polypeptide sequences can be isolated using a method similar to those described herein, or using another method. In addition, such polynucleotide and polypeptide sequences can be chemically synthesized.

Definitions

The phrase "active on", with reference to a particular cellular target, such as the product of a particular gene, means that the target is an important part of a cellular pathway which includes that target and that an agent or compound acts on that pathway. Thus, in some cases the agent or compound may act on a component upstream or downstream of the stated target, including a regulator of that pathway or a component of that pathway. In general, an antibacterial agent is active on an essential cellular function, often on a product of an essential gene.

As used herein, the terms "inhibit", "inhibition", "inhibitory", and "inhibitor" all refer to a function of reducing a biological activity or function. Such reduction in activity or function can, for example, be in connection with a cellular component (e.g., an enzyme), or in connection with a cellular process (e.g., synthesis of a particular protein), or in connection with an overall process of a cell (e.g., cell growth). In reference to cell growth, the inhibitory effects may be bacteriocidal (killing of bacterial cells) or bacteriostatic (i.e.-stopping or at least slowing bacterial cell growth). The latter slows or prevents cell growth such that fewer cells of the strain are produced relative to uninhibited cells over a given time period. From a molecular standpoint, such inhibition may equate with a reduction in the level of, or elimination of, the transcription and/or translation of a specific bacterial target(s), or reduction or elimination of activity of a particular target biomolecule.

As used herein, the term "DnaI polypeptide" refers to a polypeptide encompassing *S. aureus* DnaI (SEQ ID NO:2) or an active domain of *S. aureus* DnaI. As used herein, the term "active domain of *S. aureus* DnaI" is a polypeptide fragment or portion of *S. aureus* DnaI that retains the activity of *S. aureus* DnaI. The term "DnaI polypeptide" is meant to encompass *S. aureus* DnaI or an active domain of *S. aureus* DnaI that is fused to another, non-DnaI polypeptide sequence, and does not encompass the known *Bacillus subtilis* DnaI polypeptide and nucleotide sequences.

"DnaI activity" is defined as one or more of the following:

A) The activity of a polypeptide having the *S. aureus* DNA I sequence provided herein, a fragment or analog thereof or a protein comprising a *S. aureus* DnaI polypeptide that directly interacts with bacteriophage 77 ORF 104 protein or a DnaI-binding fragment thereof in a manner that results in at least a 10-fold reduction of $^3$H-thymidine incorporation in a bacterial DNA replication assay relative to $^3$H-thymidine incorporation in an assay lacking bacteriophage 77 ORF 104 or a DnaI-binding fragment thereof.

To assay for DnaI activity by $^3$H thymidine incorporation, the level of radiolabeled thymidine incorporation into DNA is measured in *S. aureus* cells expressing an arsenite-inducible P77 ORF104 construct in the presence or absence of 5 $\mu$M sodium arsenite. Samples (0.5 ml) are withdrawn from cultures at appropriate time intervals and mixed with 4.5 $\mu$l of labeling solution (0.2 $\mu$Ci/ml of $^3$H-thymidine (73 Ci.mmol, NEN Life Science Products, Inc.) And 70 pmol of unlabeled thymidine). After 15 minutes of reaction, incorporation is stopped by adding 5 $\mu$l of 0.2% NaN$_3$ and 5 $\mu$l of 30 $\mu$g/ml unlabeled thymidine. Samples are precipitated with 10% (w/v) trichloroacetic acid and filtered through glass fiber filters (GF-C, Whatman). The results are expressed as $^3$H -thymidine counts incorporated, normalized to the OD of the culture.

B) The activity of a polypeptide having the *S. aureus* DNA sequence provided herein, or a fragment or analog thereof, or a protein comprising a *S. aureus* DnaI polypeptide that is necessary for at least a 10% inhibition of plasmid replication by bacteriophage 77 ORF 104 protein in the plasmid replication assay. This assay is as follows, the plasmid pC194 replicates in *S. aureus* by a rolling circle mechanism. The single-stranded origin, sso, of pC194 is involved in the synthesis of the lagging strand of DNA. The plasmid pADG6406 is a derivative of pC194 lacking sso. The absence of sso leads to the accumulation of single-stranded plasmid DNA. The single stranded initiation site, ssiA, is located on the lagging strand of pAM 1, and is a site for replicative primosome assembly. SsiA was inserted into plasmid pADG6406. *S. aureus* cells carrying plasmids are grown to mid-log phase and their total DNA is extracted and analyzed by Southern hybridization using $^{32}$P-labeled plasmid DNA as probe. The presence of pADG6406 with ssiA is associated with a decrease in the ratio of single-stranded to double-stranded plasmid DNA compared to the ratio in cells bearing the same plasmid lacking the ssiA insert. This system is used to measure the effect of P77 ORF 104 expression on single-stranded DNA synthesis. A plasmid containing P77 ORF 104 under an arsenite-indicible promoter is transformed into *S. aureus* harboring pADG6406. The ratio of single-stranded to double-stranded DNA of pADG6406 is measured in the presence and absence of sodium arsenite. An increase in the ratio of single-stranded to double-stranded DNA of 10% or more in the presence of P77 ORF 104 indicates an effect on DnaI activity.

C) The activity of a polypeptide having the *S. aureus* sequence provided herein, a fragment or analog thereof, or a protein comprising a *S. aureus* DnaI polypeptide in the loading of *S. aureus* DnaC helicase onto replicative primosomes. The following helicase assay can be adapted from an in vitro assay with SPPI phage G38P(DnaA), G39P (DnaI) and G40P (DnaC) (Ayora et al., 1999, J. Mol. Biol. 288:

71–85). Helicases are capable of unwinding DNA with a 5' to 3' unwinding polarity. To determine the role of S. aureus DnaI on the helicase unwinding activity, an annealed substrate with a 3' single-stranded (ss) DNA tail (preformed fork) is incubated with a constant quantity of purified dnaC helicase and increasing amounts of either purified DnaI, DnaA or preformed DnaA-DnaI complex. The reaction mixture is subjected to conditions that support helicase activity. The reaction contains 50 mM NaCl, 1 mM ATP, 50 µg/ml BSA and 0.24 nM $^{32}$P-labelled oligomer annealed to M13 ssDNA offered as substrate. The DNA molecule in the reaction mixture is analyzed for whether it is converted to single-stranded (ss) DNA. The reaction is stopped by the addition of 5 µof stopping solution (100 mM EDTA, 2% (w/v) SDS in DNA loading buffer (Sambrook 1989)) and subsequently loaded onto a 10% non-denaturing PAGE gel. The gel is run and dried prior to autoradiography. The ratio of the oligo released from the M13 ssDNA is evaluated.

The activity of the dnaI gene is defined as the expression of an RNA encoding a S. aureus DnaI polypeptide according to the invention.

As used herein, the term "polynucleotide encoding a polypeptide" or equivalent language encompasses polynucleotides that include a sequence encoding a polypeptide of the invention, particularly a bacterial polypeptide and more particularly a polypeptide of S. aureus DnaI protein having an amino acid sequence set out in FIG. 1, SEQ ID NO:2. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

As used herein, the term "dnaI gene" is meant to encompass a polynucleotide encoding a S. aureus DnaI polypeptide. Any additional nucleotide sequences necessary to direct transcription of RNA encoding a S. aureus DnaI polypeptide, either in a cell or in vitro, will be termed "regulatory sequences", which include but are not limited to transcriptional promoters and enhancers, and transcription terminators.

As used herein, the term "ORF 104" or "phage P77 ORF 104" encompasses a polynucleotide having the sequence provided in FIG. 4 (SEQ ID No:4), which encodes a gene product known as the P77 ORF 104 gene product.

As used herein, the term "polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide (s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation, selenoylation, sulfation and transfer-RNA mediated addition of amino acids to proteins, such as arginylation, and ubiquitination. See, for instance: PROTEINS—STRUCTURE AND MOLECULAR PROPERTIES, 2nd Ed., T. E. Creighton, W.H. Freeman and Company, New York (1993); Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990); and Rattan et al., Protein Synthesis: Posttranslational Modifications and Aging, Ann. N.Y. Acad. Sci. 663: 48–62(1992). Polypeptides may be branched or cyclic, with or without branching. Cyclic, branched and branched circular polypeptides may result from post-translational natural processes and may be made by entirely synthetic methods, as well.

As used herein, the term "variant(s)" refers to a polynucleotide or polypeptide that differs from a reference polynucleotide or polypeptide, respectively, but retains one or more of the biological activities of DnaI as described herein. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, and truncations in the polypeptide encoded by the reference sequence, or in the formation of fusion proteins, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes variants of each of the polypeptides of the invention, that is polypeptides that vary from the referents by conservative amino acid substitutions whereby a residue is substituted by another with like characteristics. Typically, such substitutions are among Val, Leu and Ile; among Ser and Thr; among the acidic residues Asp and Glu; and among the basic residues Lys and Arg; or aromatic residues Phe and Tyr. Particularly preferred are variants in which 1–10, 1–5, 1–3, 2–3, or 1 amino acid or amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

As uses herein, the term "fragment", when used in reference to a polypeptide, is a variant polypeptide having an amino acid sequence that is entirely the same as part but not all of the amino acid sequence of DnaI polypeptide according to the invention. As with *S. aureus* DnaI polypeptides, fragments may be "free-standing" ("consisting of"), or comprised within a larger polypeptide of which they form a part or region, most preferably as a single continuous region in a single larger polypeptide.

The term "isolated", when used in reference to a nucleic acid means that a naturally occurring sequence has been removed from its normal cellular (e.g., chromosomal) environment or is synthesized in a non-natural environment (e.g., artificially synthesized). Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

The term "enriched", when used in reference to a polynucleotide means that the specific DNA or RNA sequence constitutes a significantly higher fraction (2–5 fold) of the total DNA or RNA present in the cells or solution of interest than in normal or diseased cells or in cells from which the sequence was originally taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased.

As used herein, the term "significantly higher fraction" indicates that the level of enrichment is useful to the person making such an enrichment and indicates an increase enrichment relative to other nucleic acids of at least about 2-fold, or 5- to 10-fold or even more. The term also does not imply that there is no DNA or RNA from other sources. The other source DNA may, for example, comprise DNA from a yeast or bacterial genome, or a cloning vector such as pUC 19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

As used herein, the term "purified" in reference to nucleic acid does not require absolute purity (such as a homogeneous preparation). Instead, it represents an indication that the sequence is relatively more pure than in the natural environment (compared to the natural level, this level should be at least 2–5 fold greater, e.g., in terms of mg/mL). Individual clones isolated from a genomic or cDNA library may be purified to electrophoretic homogeneity. The claimed DNA molecules obtained from these clones could be obtained directly from total DNA or from total RNA. cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message over its proportion in naturally occurring cells. Thus, purification of at least one order of magnitude, preferably two or three orders, and more preferably four or five orders of magnitude is expressly contemplated. A genomic library can be used in the same way and yields the same approximate levels of purification.

The terms "isolated", "enriched", and "purified" used with respect to nucleic acids, above, may similarly be used to denote the relative purity and abundance of polypeptides. These, too, may be stored in, grown in, screened in, and selected from libraries using biochemical techniques familiar in the art. Such polypeptides may be natural, synthetic or chimeric and may be extracted using any of a variety of methods, such as antibody immunoprecipitation, other "tagging" techniques, conventional chromatography and/or electrophoretic methods. Some of the above utilize the corresponding nucleic acid sequence.

As used herein, the term "complement" when used in reference to a given polynucleotide sequence refers to a sequence of nucleotides which can form a double-stranded heteroduplex in which every nucleotide in the sequence of nucleotides is base-paired by hydrogen bonding to a nucleotide opposite it in the heteroduplex with the given polynucleotide sequence. The term may refer to a DNA or an RNA sequence that is the complement of another RNA or DNA sequence. As used herein, the term "hybridizes" refers to the formation of a hydrogen-bonded heteroduplex between two nucleic acid molecules. Generally, a given nucleic acid molecule will hybridize with its complement, or with a molecule that is sufficiently complementary to the given molecule to permit formation of a hydrogen-bonded heteroduplex between the two molecules.

As used herein, the term "probe" refers to a polynucleotide of at least 15 nucleotides (nt), 20 nt, 30 nt, 40 nt, 50 nt, 75 nt, 100 nt, 200 nt, 500 nt, 1000 nt, and even up to 10,000 nt in length.

"Identity" and "similarity," as used herein and as known in the art, are relationships between two or more polypeptide sequences or two or more polynucleotide sequences, as the case may be, as determined by comparing the sequences.

Amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443–453). "Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide . In contrast to identity, "similarity" encompasses amino acids that are conservative substitutions. A "conservative" substitution is any substitution that has a positive score in the blosum62 substitution matrix (Hentikoff and Hentikoff, 1992, Proc. Natl. Acad. Sci. USA 89: 10915–10919). By the statement "sequence A is n% similar to sequence B" is meant that n% of the positions of an optimal global alignment between sequences A and B consists of conservative substitutions. By the statement "sequence A is n% identical to sequence B" is meant that n% of the positions of an optimal global alignment between sequences A and B consists of identical residues or nucleotides. Optimal global alignments in this disclosure used the following parameters in the Needleman-Wunsch alignment algorithm:

For polypeptides:
Substitution matrix: blosum62.
Gap scoring function: -A -B*LG, where A=11 (the gap penalty), B=1 (the gap length penalty) and LG is the length of the gap.
For nucleotide sequences:
Substitution matrix: 10 for matches, 0 for mismatches.
Gap scoring function: -A -B *LG where A=50 (the gap penalty), B=3 (the gap length penalty) and LG is the length of the gap.

Typical conservative substitutions are among Ala, Val, Leu and Ile; among Ser and Thr; among the acidic residues Asp and Glu; among Asn and Gln; and among the basic residues Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

As used herein, the term "antibody" is meant to encompass constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate. Neutralizing antibodies are especially useful according to the invention for diagnostics, therapeutics and methods of drug screening and drug design.

As used herein, the term "specific for an epitope present on a *S. aureus* DnaI polypeptide", when used in reference to an antibody, means that the antibody recognizes and binds an antigenic determinant present on a *S. aureus* DnaI polypeptide according to the invention.

As used herein, the term "antigenically equivalent derivative(s)" encompasses a polypeptide, polynucleotide, or the equivalent of either which will be specifically recognized by certain antibodies which, when raised to the protein, polypeptide or polynucleotide according to the invention, interferes with the immediate physical interaction between pathogen and mammalian host.

As used herein, the term "essential", when used in connection with a gene or gene product, means that the host cannot survive without, or is significantly growth compromised, in the absence or depletion of functional product. An "essential gene" is thus one that encodes a product that is beneficial, or preferably necessary, for cellular growth in vitro in a medium appropriate for growth of a strain having a wild-type allele corresponding to the particular gene in question. Therefore, if an essential gene is inactivated or inhibited, that cell will grow significantly more slowly than a wild-type strain or even not at all. Preferably, growth of a strain in which such a gene has been inactivated will be less than 20%, more preferably less than 10%, most preferably less than 5% of the growth rate of the wild-type, or the rate will be zero., in the growth medium. Preferably, in the absence of activity provided by a product of the gene, the cell will not grow at all or will be non-viable, at least under culture conditions similar to normal in vivo growth conditions. For example, absence of the biological activity of certain enzymes involved in bacterial cell wall synthesis can result in the lysis of cells under normal osmotic conditions, even though protoplasts can be maintained under controlled osmotic conditions. Preferably, but not necessarily, if such a gene is inhibited, e.g., with an antibacterial agent or a phage product, the growth rate of the inhibited bacteria will be less than 50%, more preferably less than 30%, still more preferably less than 20%, and most preferably less than 10% of the growth rate of the uninhibited bacteria. As recognized by those skilled in the art, the degree of growth inhibition will generally depend upon the concentration of the inhibitory agent. In the context of the invention, essential genes are generally the preferred targets of antimicrobial agents. Essential genes can encode "target" molecules directly or can encode a product involved in the production, modification, or maintenance of a target molecule.

As used herein, target refers to a biomolecule or complex of biomolecules that can be acted on by an exogenous agent or compound, thereby modulating, preferably inhibiting, growth or viability of a bacterial cell. A target may be a nucleic acid sequence or molecule, or a polypeptide or a region of a polypeptide.

As used herein, the term "signal that is generated by activation or inhibition of a *S. aureus* DnaI polypeptide" refers to the measurable indicator of DnaI activity in an assay [Modify of necessary to agree with def of activity] of DnaI activity. For example, $^3$H-thymidine incorporation, plasmid replication, helicase loading, or simply signal resulting for binding of P770RF104 to a DnaI polypeptide.

As used herein, the term "standard", used in reference to polypeptide activity, means the amount of activity observed or detected (directly or indirectly) in a given assay performed in the absence of a candidate compound. A "standard" serves as a reference to determine the effect, positive or negative, of a candidate compound on polypeptide activity.

A "candidate compound" as used herein, is any compound with a potential to modulate the expression or activity of a *S. aureus* DnaI polypeptide.

As used herein, the term "increase in activity" refers to an enhanced level of measurable activity of a polypeptide in a given assay in the presence of a candidate compound relative to the measurable level of activity in the absence of a candidate compound. Activity is considered increased according to the invention if it is at least 10% greater, 20% greater, 50% greater, 75% greater, 100% greater or more, up to 2-fold, 5-fold, 10-fold, 20-fold, 50-fold, 100-fold or more than in the absence of a candidate compound.

As used herein, the term "decrease in activity" refers to a reduced level of measurable activity of a polypeptide in a given assay in the presence of a candidate compound relative to the measurable level of activity in the absence of a candidate compound. Activity is considered decreased according to the invention if it is at least 10% less, preferably 15% less, 20% less, 50% less, 75% less, or even 100% less (i.e., no activity) than that observed in the absence of a candidate compound.

As used herein, the term "conditions that permit their interaction", when used in reference to a *S. aureus* DnaI polypeptide and a candidate compound means that the two entities are placed together, whether both in solution or with one immobilized or restricted in some way and the other in solution, wherein the parameters (e.g., salt, detergent, protein or candidate compound concentration, temperature, and redox potential, among others) of the solution are such that the *S. aureus* DnaI polypeptide and the candidate compound may physically associate. Conditions that permit protein:candidate interaction include, for example, the conditions described herein for Surface Plasmon Resonance and FRET assays.

As used herein, the term "detectable change in a measurable parameter of DnaI" refers to an alteration in a quantifiable characteristic of a *S. aureus* DnaI polypeptide.

As used herein, the term "agonist" refers to an agent or compound that enhances or increases the activity of a *S. aureus* DnaI polypeptide or polynucleotide. An agonist may be directly active on a *S. aureus* DnaI polypeptide or polynucleotide, or it may be active on one or more constituents in a pathway that leads to enhanced or increased activity of a *S. aureus* DnaI polypeptide or polynucleotide.

As used herein, the term "antagonist" refers to an agent or compound that reduces or decreases the activity of a *S. aureus* DnaI polypeptide or polynucleotide. An antagonist may be directly active on a *S. aureus* DnaI polypeptide or polynucleotide, or it may be active on one or more constituents in a pathway that leads to reduced or decreased activity of a *S. aureus* DnaI polypeptide or polynucleotide.

As used herein, the term "antibacterial agent" or "antibacterial compound" refers to an agent or compound that has a bacteriocidal or bacteriostatic effect on one or more bacterial strains, preferably such an agent or compound is bacteriocidal or bacteriostatic on at least *S. aureus*.

As used herein, the term "synthesizing" refers to a process of chemically synthesizing a compound.

As used in the context of treating a bacterial infection a "therapeutically effective amount", "pharmaceutically effective amount" or "amount sufficient to provide a therapeutic effect" indicates an amount of an antibacterial agent which has a therapeutic effect. This generally refers to the inhibition, to some extent, of the normal cellular functioning of bacterial cells required for continued bacterial infection. Further, as used herein, a therapeutically effective amount means an amount of an antibacterial agent that produces the desired therapeutic effect as judged by clinical trial results and/or animal models. This amount can be routinely determined by one skilled in the art and will vary depending on several factors, such as the particular bacterial strain involved and the particular antibacterial agent used. In the same context, an "amount sufficient to reduce adhesion" of a bacterium to a tissue or tissue surface indicates an amount of an antibacterial agent that is effective for prophylactically preventing or reducing the extent of bacterial infection of the given tissue or tissue surface.

As used herein, a "tissue" refers to an aggregation of cells of one or more cell types which together perform one or more specific functions in an organism. As used herein, a "tissue surface" refers to that portion of a tissue that forms a boundary between a given tissue and other tissues or the surroundings of the tissue. A tissue surface may refer to an external surface of an animal, for example the skin or cornea, or, alternativley, the term may refer to a surface that is either internal, for example, the lining of the gut, or to a surface that is exposed to the outside surroundings of the animal only as the result of an injury or a surgical procedure.

As used herein, the term "measuring the binding of a candidate compound" refers to the use of an assay permitting the quantitation of the amount of a candidate compound physically associated with a *S. aureus* DnaI polypeptide.

As used herein, the term "directly or indirectly detectably labeled" refers to the attachment of a moiety to a candidate compound that renders the candidate compound either directly detectable (e.g., an isotope or a fluorophore) or indirectly detectable (e.g., an enzyme activity, allowing detection in the presence of an appropriate substrate, or a specific antigen or other marker allowing detection by addition of an antibody or other specific interactor).

As used herein, the term "small molecule" refers to compounds having molecular mass of less than 3000 Daltons, preferably less than 2000 or 1500, still more preferably less than 1000, and most preferably less than 600 Daltons. Preferably but not necessarily, a small molecule is not an oligopeptide.

As used herein, the term "mimetic" refers to a compound that can be natural, synthetic, or chimeric and is structurally and functionally related to a reference compound. In terms of the present invention, a "peptidomimetic," for example, is a non-peptide compound that mimics the activity-related aspects of the 3-dimensional structure of a peptide or polypeptide, for example a compound that mimics the structure of a peptide or active portion of a phage- or bacterial ORF-encoded polypeptide.

As used herein, the term "bacteriophage inhibitor protein" refers to a protein encoded by a bacteriophage nucleic acid sequence, which inhibits bacterial function in a host bacterium. Thus, it is a bacteria-inhibiting phage product. The term "bacteriophage inhibitor protein" encompasses a fragment, derivative, or active portion of a bacteriophage inhibitor protein.

As used herein, the term "active portion" refers to an epitope, a catalytic or regulatory domain, or a fragment of a bacteriophage inhibitor protein that is responsible for, or a significant factor in, bacterial target inhibition. The active portion preferably may be removed from its contiguous sequences and, in isolation, still effect inhibition.

As used herein, the term "treating a bacterial infection" refers to a process whereby the and/or metabolic activity of a bacterium or bacterial population in a host, preferably a mammal, more preferably a human, is inhibited or ablated.

As used herein, the term "bacterium" refers to a single bacterial strain and includes a single cell and a plurality or population of cells of that strain unless clearly indicated to the contrary. In reference to bacteria or bacteriophage, the term "strain" refers to bacteria or phage having a particular genetic content. The genetic content includes genomic content as well as recombinant vectors. Thus, for example, two otherwise identical bacterial cells would represent different strains if each contained a vector, e.g., a plasmid, with different inserts.

As used herein, the term "diagnosing" refers to the identification of an organism or strain of an organism responsible for a bacterial infection.

As used herein, the term "infection with *Staphylococcus aureus*" refers to the presence, growth or proliferation of cells of a *S. aureus* strain within, or on a surface of, an animal, such as a mammal, preferably a human.

As used herein, the term "bacteriophage P77 ORF 104-encoded polypeptide" refers to a polypeptide encoded by SEQ ID NO:4 or to a fragment or derivative thereof encompassing an active portion of a bacteriophage P77 ORF 104-encoded polypeptide of sequence disclosed in SEQ ID NO:5.

As used herein, the term "DnaC" refers to a polypeptide of SEQ ID NO:9, including that encoded by a polynucleotide of SEQ ID NO:7 or to a fragment or derivative of such polypeptide encompassing an active portion of *S. aureus* DnaC. In this context, an active portion of *S. aureus* DnaC refers to that fragment or portion of *S. aureus* DnaC that interacts with or is part of a complex including *S. aureus* DnaI or a fragment or derivative of *S. aureus* DnaI.

As used herein, the term "polypeptide complex" refers to a combination of two or more polypeptides in a physical association with each other. It is preferred that such a physical association be required for some aspect of the activity of one or more of the polypeptides in such a polypeptide complex.

As used herein, the term "physical association" refers to an interaction between two moieties involving contact between the two moieties.

As used herein, the term "bodily material(s)" means any material derived from an individual or from an organism infecting, infesting or inhabiting an individual, including but not limited to, cells, tissues and waste, such as, bone, blood, serum, cerebrospinal fluid, semen, saliva, muscle, cartilage, organ tissue, skin, urine, stool or autopsy materials.

As used herein, the term "disease(s)" means any disease caused by or related to infection by a bacterium, including, for example, otitis media, conjunctivitis, pneumonia, bacteremia, meningitis, sinusitis, pleural empyema and endocarditis, and most particularly meningitis, such as for example infection of cerebrospinal fluid.

As used herein, the term "fusion protein(s)" refers to a protein encoded by a gene comprising amino acid coding sequences from two or more separate proteins fused in frame such that the protein comprises fused amino acid sequences from the separate proteins.

As used herein, the term "host cell(s)" is a cell which has been transformed or transfected, or is capable of transformation or transfection by an exogenous polynucleotide sequence.

As used herein, the term "immunologically equivalent derivative(s)" encompasses a polypeptide, polynucleotide, or the equivalent of either which when used in a suitable formulation to raise antibodies in a vertebrate, results in antibodies that act to interfere with the immediate physical interaction between pathogen and mammalian host.

As used herein, the term "immunospecific" means that characteristic of an antibody whereby it possesses substantially greater affinity for the polypeptides of the invention or the polynucleotides of the invention than its affinity for other related polypeptides or polynucleotides respectively, particularly those polypeptides and polynucleotides in the prior art.

As used herein, the term "individual(s)" means a multicellular eukaryote, including, but not limited to a metazoan, a mammal, an ovid, a bovid, a simian, a primate, and a human.

As used herein, the term "Organism(s)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, *Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis,* (ii) an archaeon, including but not limited to Archaebacter, and (iii) a unicellular or filamenous eukaryote, including but not limited to, a protozoan, a fungus, a member of the genus Saccharomyces, Kluveromyces, or Candida, and a member of the species *Saccharomyces ceriviseae, Kluveromyces lactis,* or *Candida albicans.*

As used herein, the term "recombinant expression system (s)" refers to a system in which vectors comprising sequences encoding polypeptides of the invention or portions thereof, or polynucleotides of the invention are introduced or transformed into a host cell or host cell lysate for the production of the polynucleotides and polypeptides of the invention.

In addition to the standard single and triple letter representations for amino acids, the term "X" or "Xaa" may also be used in describing certain polypeptides of the invention. "X" and "Xaa" mean that any of the twenty naturally occurring amino acids may appear at such a designated position in the polypeptide sequence.

How to Identify a *S. aureus* DnaI Sequence

Using methodology described in detail in Example 1, a *S. aureus* polypeptide that specifically bound the P77 phage ORF 104 protein was isolated. The sequence of a tryptic peptide of the *S. aureus* polypeptide, GHVPENVTDNDR (SEQ ID NO:16), was used to BLAST search the *S. aureus* nucleotide sequence in the University of Oklahoma *S. aureus* genomic database at http://www.genome.ou.edu/staph.html. One sequence contig of 4850 nucleotides in length (Contig 981), when converted into amino acid sequence, contained within it the similar amino acid sequence GHVPELYVDNNR (SEQ ID NO:11; FIG. 5). This tentative identification of the candidate protein was then confirmed upon in silico tryptic digestion of the open reading frame found in the contig (FIG. 5). The obtained PSD/CID spectra for tryptic peptides with monoisotopic MH+ masses of 1351.8, 1412.7, and 1617.8 Da were similar to the predicted PSD/CID fragmentation patterns of the tryptic peptides with monoisotopic MH+ masses of 1351.8 and 1617.8 Da found in the contig's +3 open reading frame (FIG. 5).

Comparison of the ORF of the *S. aureus* contig that encodes a tryptic peptide similar to that identified in the *S. aureus* P77ORF binding studies with all other sequences in the public domain databases revealed that the ORF is related to the DnaI protein from *Bacillus subtilis* (Table 1)—a protein implicated in chromosome replication. No other significant similarity was found with any other protein in publicly accessible databases. The degree of relatedness of the identified ORF to the *B. subtilis* DnaI protein shows 41% identity and 63% similarity (Table 1).

Many genes of *B. subtilis* involved in DNA replication have been identified through the isolation of thermosensitive mutants. One of these, dnaI2, affected an unknown step of chromosome replication at the restrictive temperature (Karamata, D. and Gross, J. D. (1970) Mol. Gene. Genet. 108, 277–287). The gene was mapped around 250° on the *B subtilis* chromosome and resides immediately downstream of the dnaB gene on the *B. subtilis* chromosome (Bruand, C. and Ehrlich, S. D. (1995) Microbiology 141, 1199–1200). The dnaI2 mutation has been characterized and resides within the dnaI gene and consists of a G to A substitution at nucleotide position 922 (FIG. 1; SEQ ID NO:1) resulting in a glycine to glutamate change at position 307 (FIG. 1; SEQ ID NO:2) (Bruand, C. and Ehrlich, S. D. (1995) Microbiology 141, 1199–1200). DnaC has been genetically identified to be the major component DNA helicase of chromosome replication (Sakamoto, Y., Nakai, S., Moriya, S., Yoshikawa, H., and Ogasawara, N. (1995) Microbiology 141, 641–644) and is thought to unwind duplex DNA progressively and allow for binding of the DNA polymerase III haloenzyme necessary for priming and DNA synthesis. One possible function of DnaI is as a helicase loader, being responsible for transferring DnaC helicase to the oriC. The product of the dnaC and dnaI genes are required for chromosome replication and are all essential for DNA replication in *B. subtilis* (Ceglowski, P., Lurz, R., Alonso, J. C. J. (1993) Mol. Biol. 236, 1324–1340).

Databases were searched for *S. aureus* genes which may be related to the *B. subtilis* dnaC gene. Utilizing the *B. subtilis* amino acid sequence for DnaC (Accession Number P37469), a BLAST search was performed of the Staphylococcus database at http://www.tigr.org and revealed the presence of an ORF within the *S. aureus* genome encoding a related protein. The nucleotide sequence and corresponding protein sequence are presented in FIG. 6A (SEQ ID NO:7 and FIG. 6B (SEQ ID NO:9, respectively.

*S. aureus* DnaI Polypeptides

In one aspect of the invention there are provided polypeptides of *S. aureus* referred to herein as "DnaI" and "DnaI polypeptides" as well as biologically, diagnostically, prophylactically, clinically or therapeutically useful variants thereof, and compositions comprising the same.

Among the particularly preferred embodiments of the invention are variants of *S. aureus* DnaI polypeptides encoded by naturally occurring alleles of the dnai gene. The present invention provides for an isolated polypeptide which comprises or consists of: (a) an amino acid sequence which has at least 50% identity, preferably at least 80% identity, more preferably at least 90%, yet more preferably at least 95%, most preferably at least 97–99% or exact identity, to that of SEQ ID NO:2 over the entire length of SEQ ID NO:2 or b) an amino acid sequence that has at least 70% similarity, at least 80% similarity, at least 90% similarity, at least 95% similarity, at least 97–99% similarity or even 100% similarity over the entire length of SEQ.D. No.2.

The polypeptides of the invention include a polypeptide of FIG. 1 (SEQ ID NO:2) (in particular the mature polypeptide) as well as polypeptides and fragments, particularly those which have the biological activity of DnaI, and also those which have at least 50% identity over 20, 40, 50 or more amino acids to a polypeptide of SEQ ID NO:2 or the relevant portion, preferably at least 60%, 70%, or 80% identity, more preferably at least 90% identity to a polypeptide of SEQ ID NO:2 and more preferably at least 90% identity to a polypeptide of SEQ ID NO:2 and still more preferably at least 95% identity to a polypeptide of SEQ ID NO:2 and yet still more preferably at least 99% identity to a polypeptide of SEQ ID NO:2.

The polypeptides of the invention also include a polypeptide or protein fragment that has at least 60%, 70%, 80% or 90% similarity, 95% similarity or even 97–99% similarity over 10, 20, 25, 30 or more amino acids to a polypeptide of SEQ ID NO:2. It is preferred that a polypeptide of the invention has at least 60% similarity to a polypeptide of SEQ ID NO: 2 over at least 20 amino acids.

It is most preferred that a polypeptide of the invention is derived from *S. aureus*, however, it may be obtained from other organisms of the same taxonomic genus. A polypeptide of the invention may also be obtained, for example, from organisms of the same taxonomic family or order.

Fragments of DnaI also are included in the invention. These fragments may include, for example, truncation polypeptides having a portion of an amino acid sequence of FIG. 1 (SEQ ID NO:2), or variants thereof, such as a continuous series of residues that includes an amino- and/or carboxyl-terminal amino acid sequence. Degradation forms of the polypeptides of the invention produced by or in a host cell, particularly *S. aureus*, are also preferred. Further preferred are fragments characterized by structural or functional attributes such as fragments that comprise alpha-helix and alpha-helix-forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Fragments of DnaI may be expressed as fusion proteins with other proteins or protein fragments.

Preferred fragments also include an isolated polypeptide comprising an amino acid sequence having at least 20, 30, 40, 50, or 100 contiguous amino acids from the amino acid sequence of SEQ ID NO:2.

Also preferred are biologically "active" fragments which are those fragments that mediate activities of *S. aureus* DnaI, including those with a similar activity or an improved activity, or with a decreased undesirable activity. Also included are those fragments that are antigenic or immunogenic in an animal, especially in a human. Particularly preferred are fragments comprising domains that confer a function essential for viability of S. aureus.

Fragments of the polypeptides of the invention may be employed for producing the corresponding full-length polypeptide by peptide synthesis; therefore, these variants may be employed as intermediates for producing the full-length polypeptides of the invention.

S. aureus Polynucleotides

It is an object of the invention to provide polynucleotides that encode DnaI polypeptides, particularly polynucleotides that encode the polypeptide herein designated S. aureus DnaI.

In one aspect of the invention a polynucleotide is provided that comprises a region encoding a S. aureus DnaI polypeptide, the polynucleotide comprising a sequence set out in SEQ ID NO:1. Such a polynucleotide encodes a full length DnaI gene, or a variant thereof. It is contemplated that this full length gene is essential to the growth and/or survival of an organism which possesses it, such as S. aureus.

As a further aspect of the invention there are provided isolated nucleic acid molecules encoding and/or expressing a fragment of a full length DnaI polypeptide, particularly a S. aureus DnaI polypeptide or a variant thereof. Further embodiments of the invention include biologically, diagnostically, prophylactically, clinically or therapeutically useful polynucleotides and polypeptides, and variants thereof, and compositions comprising the same.

A polynucleotide of the invention is obtained using S. aureus cells as starting material, the nucleotide sequence information disclosed in SEQ ID No:1, and standard cloning and screening methods, such as those for cloning and sequencing chromosomal DNA fragments from bacteria. For example, to obtain a polynucleotide sequence of the invention, such as the polynucleotide sequence disclosed as in SEQ ID NO:1, a library of clones of chromosomal DNA of S. aureus in E. coli or another suitable host is probed with a radiolabeled oligonucleotide, preferably a 17-mer or longer, derived from a partial sequence. Clones carrying DNA identical to that of the probe can be distinguished using stringent hybridization conditions. As herein used, the terms "stringent conditions" and "stringent hybridization conditions" mean hybridization occurring only if there is at least 95% and preferably at least 97% identity between the sequences. A specific example of stringent hybridization conditions is of a overnight incubation of hybridization support (e.g., a nylon or nitrolcellulose membrane overnight incubation at 42° C. in a solution comprising: $1 \times 10^6$ cpm/ml labeled probe, 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention. By sequencing the individual clones thus identified by hybridization it is possible to confirm the identity of the clone.

Alternatively, an amplification process can be utilized to isolate the poylnucleotide. In this approach, the sequence disclosed as SEQ ID NO:1 is targeted by two oligonucleotides, one identical to a sequence on the coding DNA strand at or upstream of the ATG initiation codon and the other which anneals to the opposite strand at or downstream of the stop codon. Priming from these oligonucleotides in a polymerase chain reaction yields a full length gene coding sequence. Such suitable techniques are described by Maniatis, T., Fritsch, E. F. and Sambrook, MOLECULAR CLONING: A LABORATORY MANUAL, $2^{nd}$ Edition, Cold Spring Harbor Laboratory Press, Cold Spring Harbor, N.Y. (1989).

In a further aspect, the present invention provides for an isolated polynucleotide comprising or consisting of: (a) a polynucleotide sequence which has at least 60% identity, preferably at least 70% identity, more preferably at least 80% identity, more preferably at least 90% identity, yet more preferably at least 95%, most preferably at least 97–99% or exact identity, to that of SEQ ID NO:1 over the entire length of SEQ ID NO:1; (b) a polynucleotide sequence encoding a polypeptide which has at least 50% identity, preferably at least 60% identity, more preferably at least 70% identity, more preferably at least 80% identity, more preferably at least 90%, yet more preferably at least 95%, most preferably at least 97–99% or exact identity to SEQ ID NO:2 over the entire length of SEQ ID NO:2; or the complement of a sequence of (a) or (b) above.

The invention provides a polynucleotide sequence identical over its entire length to the coding sequence of SEQ ID NO:1. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro-, or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize or destabilize mRNAs, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., Proc. Natl. Acad. Sci. 86: 821–824 (1989), or an HA peptide tag (Wilson et al., Cell 37: 767 (1984), both of which may be useful in purifying polypeptide sequences fused to them. Polynucleotides of the invention also include, but are not limited to, polynucleotides comprising a structural gene and its naturally associated sequences that control gene expression.

It is most preferred that a polynucleotide of the invention is derived from Staphylococcus aureus, however, it may also be obtained from other organisms of the same taxonomic genus. A polynucleotide of the invention may also be obtained, for example, from organisms of the same taxonomic family or order.

Further preferred embodiments are polynucleotides encoding S. aureus dnaI variants that have the amino acid sequence of S. aureus DnaI polypeptide of SEQ ID NO:2 in which several, a few, 5 to 10, 1 to 5, 1 to 3, 2, 1 or no amino acid residues are substituted, modified, deleted and/or added, in any combination. Especially preferred among these polynucleotides are those encoding silent nucleotide alterations, that do not alter the coding sequence or activities of S. aureus DnaI polypeptides they encode.

Preferred embodiments are polynucleotides encoding polypeptides that retain substantially the same biological function or activity as the mature polypeptide encoded by a DNA of SEQ ID NO:1.

In accordance with certain preferred embodiments of this invention there are provided polynucleotides that hybridize, particularly under stringent conditions, to S. aureus dnaI polynucleotide sequences, such as those polynucleotides in FIG. 1.

The polynucleotides of the invention are useful as hybridization probes for RNA, cDNA and genomic DNA to isolate full-length cDNAs and genomic clones encoding genes that have a high degree of sequence identity to the dnaI gene. Such probes generally will comprise at least 15 to about 100 residues or base pairs, Although, such probes will preferably have about 20 to 50 nucleotide residues or base pairs. Particularly preferred probes are about 20 to about 30 nucleotide residues or base pairs in length.

A coding region of a related dnaI gene from a bacterial species other than S. aureus may be isolated by screening a library using a DNA sequence provided in SEQ ID NO:1 to synthesize an oligonucleotide probe. A labeled oligonucleotide having a sequence complementary to that of a gene of the invention is then used to screen a library of cDNA, genomic DNA or mRNA to determine which member(s) of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., PNAS USA 85: 8998–9002, 1988). Recent modifications of the technique, exemplified by the MARATHON TM technology (Clontech Laboratories Inc.) for example, have significantly simplified the search for longer cDNAs. In the MARATHON TM technology, cDNAs are prepared from mRNA extracted from a chosen cell and an 'adaptor' sequence is ligated onto each end. Nucleic acid amplification by PCR is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor-specific primer that anneals further 3' in the adaptor sequence and a gene-specific primer that anneals further 5' in the selected gene sequence). The products of this reaction can then be analyzed by DNA sequencing and a full-length DNA constructed either by joining the product directly to the existing DNA to give a complete sequence, or by carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NO:1 are useful for the design of PCR primers in reactions to determine whether or not the polynucleotides identified herein in whole or in part are transcribed in bacteria in infected tissue. That is, the polynucleotides of the invention are useful for diagnosis of infection with a bacterial strain carrying those sequences. It is recognized that such sequences also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide. Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

A polynucleotide of the invention thus may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleotide that when taken in combination with adjacent nucleotide positions, read in the correct reading frame, would have the effect of generating a premature termination codon in such reading frame.

For each and every polynucleotide of the invention there is also provided a polynucleotide complementary to it.

Vectors. Host Cells and Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention Recombinant DnaI polypeptides of the present invention may be prepared by processes well known to those skilled in the art from genetically engineered host cells comprising expression systems. Accordingly, in a further aspect, the present invention relates to expression systems which comprise a dnaI polynucleotide or polynucleotides of the present invention, to host cells which are genetically engineered with such expression systems, and to the production of polypeptides of the invention by recombinant techniques.

For recombinant production of DnaI polypeptides of the invention, host cells can be genetically engineered to incorporate expression systems or portions thereof or polynucleotides of the invention. Representative examples of appropriate hosts include bacterial cells (gram positive and gram negative), fungal cells, insect cells, animal cells and plant cells. Polynucleotides are introduced to bacteria by standard chemical treatment protocols, such as the induction of competence to take up DNA by treatment with calcium chloride (Sambrook et al., supra). Introduction of polynucleotides into fungal (e.g., yeast) host cells is effected, if desired, bystandard chemcial methods, such as lithium acetate—medicated transformation.

A great variety of expression systems are useful to produce DnaI polypeptides of the invention. Such vectors include among others, chromosomal-, episomal- and virus-derived vectors. For example, vectors derived from bacterial plasmids, from bacteriophages, from transposons, from yeast episomes, from insertion elements, from yeast chromosomal elements, from viruses, and from vectors derived from combinations thereof, are useful in the invention.

DnaI polypeptides of the invention are recovered and purified from recombinant cell cultures by well-known methods including ammonium sulfate or ethanol precipitation, acid or urea extraction, anion or cation exchange chromatography, phosphocellulose chromatography, hydrophobic interaction chromatography, affinity chromatography, hydroxylapatite chromatography, and lectin chromatography. Well known techniques for refolding may be employed to regenerate an active conformation when the DnaI polypeptide is denatured during isolation and/or purification.

Diagnostic, Prognostic, Serotyping, and Mutation Assays

This invention is also related to the use of dnaI polynucleotides and polypeptides of the invention for use as diagnostic reagents. Detection of *S. aureus* dnaI polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the *S. aureus* dnaI gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled dnaI polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al, (1985) Science 230, 1242. Sequence changes at specific locations also may be revealed by nuclease protection assays, such as RNase, V1 and S1 protection assay or a chemical cleavage method. See, for example, Cotton et al., (1985) Proc. Natl. Acad. Sci., USA 85, 4397–4401.

In another embodiment, an array of oligonucleotide probes comprising dnaI nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., (1996) Science 274, 610).

Thus in another aspect, the present invention relates to a diagnostic kit which comprises: (a) a polynucleotide of the present invention, preferably the nucleotide sequence of SEQ ID NO:1, or a fragment thereof; (b) a nucleotide sequence complementary to that of (a); (c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, among others.

This invention also relates to the use of dnaI polynucleotides of the present invention as diagnostic reagents. Detection of a mutated form of a polynucleotide of the invention, preferably, SEQ ID NO:1, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

The dnaI nucleotide sequences of the present invention are also valuable for organism chromosome identification. The sequence is specifically targeted to, and can hybridize with, a particular location on an organism's chromosome, particularly to a *S. aureus* chromosome. The mapping of relevant sequences to chromosomes according to the present invention may be an important step in correlating those sequences with pathogenic potential and/or an ecological niche of an organism and/or drug resistance of an organism, as well as the essentiality of the gene to the organism. Once a sequence has been mapped to a precise chromosomal location, the physical position of the sequence on the chromosome can be correlated with genetic map data. Such data may be found on-line in a sequence database. The relationship between genes and diseases that have been mapped to the same chromosomal region are then identified through known genetic methods, for example, through linkage analysis (coinheritance of physically adjacent genes) or mating studies, such as by conjugation.

The differences in a polynucleotide and/or polypeptide sequence between organisms possessing a first phenotype and organisms possessing a different, second different phenotype can also be determined. If a mutation is observed in some or all organisms possessing the first phenotype but not in any organisms possessing the second phenotype, then the mutation is likely to be the causative agent of the first phenotype.

Polypeptides and polynucleotides for prognosis, diagnosis or other analysis may be obtained from a putatively infected and/or infected individual's bodily materials. Particularly DNA, Polynucleotides, from any of these sources may be used directly for detection or may be amplified enzymatically using PCR or other amplification technique with oligonucleotide amplification primers derived from the polynucleotide sequence of *S. aureus* dna 1. RNA, particularly mRNA, or RNA reverse transcribed to cDNA, is also useful for diagnostics. Following amplification of a *S aureus* dnaI—related polynucleotide from a sample, characterization of the species and strain of infecting or resident organism is made by an analysis of the amplified polynucleotide relative to one or more reference polynucleotides or sequences relative to a standard from a related organism (i.e. a known strain of *S. aureus* ).

Point mutations can be identified by hybridizing amplified DNA to known dnaI polynucleotide sequences and by detecting differences in melting temperatures or renaturation kinetics. Perfectly or significantly matched sequences can be distinguished from imperfectly or more significantly mismatched duplexes by RNase protection or S1 nuclease mapping. (See, for example, Cotton et al., (1988) Proc. Natl. Acad. Sci. USA 85:4397–4401). Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al, (1985) Science 230, 1242. Sequence changes at specific locations also may be revealed by nuclease protection assays, such as Rnase, V1 and S1 protection assay or a chemical cleavage method. (Cotton et al., 1988 Supra).

In another embodiment, an array of oligonucleotide probes comprising dnaI nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., (1996) Science 274, 610).

In another aspect, the present invention relates to a diagnostic kit which comprises: (a) a polynucleotide of the present invention, preferably the nucleotide sequence of SEQ ID NO: 1, or a fragment thereof; (b) a nucleotide sequence complementary to that of (a); (c) a polypeptide of the present invention, preferably the polypeptide of SEQ ID NO:2 or a fragment thereof; or (d) an antibody to a polypeptide of the present invention, preferably to the polypeptide of SEQ ID NO:2. Such a kit will be of use in diagnosing a disease or susceptibility to a disease, among other uses.

The invention further provides a process for diagnosing bacterial infections such as those caused by *S. aureus* , the process comprising determining from a sample derived from an individual, such as a bodily material, an increased level of expression of a polynucleotide having a sequence disclosed in SEQ ID NO:1 relative to a sample taken from a non-diseased individual. Increased or decreased expression of a dnaI polynucleotide can be measured using any one of the methods well known in the art for the quantitation of polynucleotides, such as, for example, PCR, RT-PCR, RNase protection, Northern blotting and other hybridization methods, and spectrometry.

In addition, a diagnostic assay in accordance with the invention for detecting over-expression of DnaI polypeptide compared to normal control tissue samples may be used to detect the presence of an infection, for example. Assay techniques that can be used to determine levels of a *S. aureus* DnaI polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

Gridding and Polynucleotide Subtraction of *S. aureus* Genomic Sequences

The dnaI polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as hybridization or nucleic acid amplification, using a probe obtained or derived from a bodily sample, to determine the presence a particular polynucleotide sequence or related sequence in an individual.

Antibodies Specific for *S. aureus* Peptides or Polypeptides

The DnaI polypeptides and polynucleotides of the invention or variants thereof, or cells expressing them are useful as immunogens to produce antibodies immunospecific for such polypeptides or polynucleotides, respectively.

In certain preferred embodiments of the invention there are provided antibodies against *S. aureus* DnaI polypeptides or polynucleotides encoding them. Antibodies against DnaI-polypeptide or dnaI-polynucleotide are useful for treatment of infections, particularly bacterial infections.

Antibodies generated against the polypeptides or polynucleotides of the invention are obtained by administering the polypeptides and/or polynucleotides of the invention or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures is useful. Examples include various techniques, such as those in Kohler, G. and Milstein, C., Nature 256: 495–497 (1975); Kozbor et al., Immunology Today 4: 72 (1983); and Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other mammals, are useful to express humanized antibodies immunospecific to the polypeptides or polynucleotides of the invention.

When antibodies are administered therapeutically, the antibody or variant thereof is preferably modified to make it less immunogenic in the individual. For example, if the individual is human the antibody is most preferably "humanized," where the complimentarity determining region or regions of the hybridoma-derived antibody has been transplanted into a human monoclonal antibody, for example as described in Jones et al. (1986), Nature 321, 522–525 or Tempest et al., (1991) Biotechnology 9, 266–273.

Alternatively, phage display technology is useful to select antibody genes with binding activities towards a DnaI polypeptide of the invention. PCR amplifed gene from human lymphocytes screened for anti-*S. aureus* DnaI antibody expression are selected by phage display technology. Alternatively, naive libraries are screened by phage display techiques to identify genes encoding antibodies specified for dnaI or from naive libraries (McCafferty, et al., (1990), Nature 348, 552–554; Marks, et al., (1992) Biotechnology 10, 779–783). The affinity of these antibodies can also be improved by, for example, chain shuffling (Clackson et al., (1991) Nature 352: 628).

The above-described antibodies may be employed to isolate or to identify clones expressing the polypeptides or polynucleotides of the invention, for example to purify the polypeptides or polynucleotides by affinity chromatography.

A variant polypeptide or polynucleotide of the invention, such as an antigenically or immunologically equivalent derivative or a fusion protein of the polypeptide is also useful as an antigen to immunize a mouse or other animal such as a rat or chicken. A fused protein provides stability to the polypeptide acting as a carrier, or acts as an adjuvant or both. Alternatively, the antigen is associated, for example by conjugation, with an immunogenic carrier protein, such as bovine serum albumin, keyhole limpet haemocyanin or tetanus toxoid. When antibodies are to be administered therapeutically, alternatively a multiple antigenic polypeptide comprising multiple copies of the polypeptide, or an antigenically or immunologically equivalent polypeptide thereof may be sufficiently antigenic to improve immunogenicity so as to obviate the use of a carrier.

In accordance with an aspect of the invention, there is provided the use of a dnaI polynucleotide of the invention for therapeutic or prophylactic purposes, in particular genetic immunization. The use of a dnaI polynucleotide of the invention in genetic immunization preferably employs a suitable delivery method such as direct injection of plasmid DNA into muscles (Wolff et al., Hum Mol Genet (1992) 1: 363, Manthorpe et al., Hum. Gene Ther. (1983) 4: 419), delivery of DNA complexed with specific protein carriers (Wu et al., JBiol Chem. (1989) 264: 16985), coprecipitation of DNA with calcium phosphate (Benvenisty & Reshef, PNAS USA, (1986) 83: 9551), encapsulation of DNA in various forms of liposomes (Kaneda et al., Science (1989) 243: 375), particle bombardment (Tang et al., Nature (1992) 356:152, Eisenbraun et al., DNA Cell Biol (1993) 12: 791) or in vivo infection using cloned retroviral vectors (Seeger et al., PNAS USA (1984) 81: 5849).

Antagonists and Agonists: Assays and Molecules

The invention is based inpart on the discovery that DnaI is a target for the bacteria phage P77ORF104 inhibitory factor. Applicants have recognized the utility of the interaction in the development of antibacterial agents. Specfically, the inventors have recognized that 1)DnaI is a critical target for bacterial inhibition; 2) P77 ORF104 or derivatives or functional mimetics thereof are useful for inhibiting bacterial growth; and 3) the interaction of S. aureus may be used as a target for the screening and rational design of drugs or antibacterial agents. In addition to methods of directly inhibiting DnaI activity, methods, of inhibiting DnaI expression are also attractive for antibacterial activity.

In several embodiments of the invention, there are provided methods for identifying compounds which bind to or otherwise interact with and inhibit or activate an activity or expression of a polypeptide and/or polynucleotide of the invention comprising: contacting a polypeptide and/or polynucleotide of the invention with a compound to be screened under conditions to permit binding to or other interaction between the compound and the polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the polypeptide and/or polynucleotide by detecting the presence or absence of a signal generated from the binding or interaction of the compound with the polypeptide and/or polynucleotide.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing dnaI-induced activities, thereby preventing the action or expression of S. aureus DnaI polypeptides and/or polynucleotides by excluding S. aureus DnaI polypeptides and/or polynucleotides from binding.

Potential antagonists also include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, (1991) J. Neurochem. 56, 560; see also OLIGODEOXYNUCLEOTIDES AS ANTISENSE INHIBITORS OF GENE EXPRESSION, CRC Press, Boca Raton, Fla. (1988), for a description of these molecules). Preferred potential antagonists include compounds related to and variants of P77ORF104 and of DnaI. Other examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Certain of the polypeptides of the invention are biomimetics, functional mimetics of the natural S. aureus DnaI polypeptide. These functional mimetics are useful for, among other things, antagonizing the activity of S. aureus DnaI polypeptide or as an antigen or immunogen in a manner described above. Functional mimetics of the polypeptides of the invention include but are not limited to truncated polypeptides. For example, preferred functional mimetics include a polypeptide comprising the polypeptide sequence set forth in SEQ ID NO:2 lacking 20, 30, 40, 50, 60, 70 or 80 amino- or carboxy-terminal amino acid residues, including fusion proteins comprising one or more of these truncated sequences. Polynucleotides encoding each of these functional mimetics may be used as expression cassettes to express each mimetic polypeptide. It is preferred that these cassettes comprise 5' and 3' restriction sites to allow for a convenient means to ligate the cassettes together when desired. It is further preferred that these cassettes comprise gene expression signals known in the art or described elsewhere herein.

Screening Assays According to the Invention

DnaI polypeptides and polynucleotides of the invention are also useful to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991).

It is desirable to devise screening methods to identify compounds which stimulate or which inhibit the function of the DnaI polypeptide or polynucleotide of the invention. Accordingly, the present invention provides for a method of screening compounds to identify those which modulate the function of a polypeptide or polynucleotide of the invention. In general, antagonists may be employed for therapeutic and prophylactic purposes. It is contemplated that an agonist of DnaI may be useful, for example, to enhance the growth rate of bacteria is a sample being cultured for diagnostic other purposes. Compounds may be identified from a variety of sources, for example, cells, cell-free preparations, chemical libraries, and natural product mixtures. Screening methods generally fall into two broad categories: those that assay binding of candidate compounds; and those that assay a functional aspect of the target.

a) Binding Assays

There are a number of methods of examining binding of a candidate compound to a protein target such as DnaI. Screening methods that measure the binding of a candidate compound to the DnaI polypeptide or polynucleotide, or to cells or supports bearing the polypeptide or a fusion protein of comprising the polypeptide, by means of a label directly or indirectly associated with the candidate compound, are useful in the invention.

The screening method may involve competition for binding of a labeled competitor such as P77ORF104 or a fragment that is competent to bind DnaI.

i) Surface Plasmon Resonance

One powerful assay for protein: protein interaction screening of inhibitors is surface plasmon resonance. Surface plasmon resonance is a quantitative method that measures binding between two (or more) molecules by the change in mass near the sensor surface caused by the binding of one protein from the aqueous phase to a second immobilized on the sensor. This change is measured as resonance units with time after injection of the protein or its removal and is measured using a Biacore Biosensor (Biacore AB). DnaI is immobilized on a sensor chip using the covalent linkage method (Biacore AB). A blank surface is prepared by activating and inactivating a sensor chip without protein immobilization . The binding of P77ORF104 to DnaI is measured by adding to the sensor an increasing quantity of purified P77ORF104. Measurements are performed at room temperature. Conditions used for the assay (i.e., those permitting binding) are as follows: 25 mM HEPES-KOH (pH 7.6), 150 mM sodium chloride, 15% glycerol, 1 mM dithiothreitol, and 0.001% Tween 20 with a flow rate of 10 ul/min at room temperature. Preincubation of the sensor chip with candidate inhibitors will decrease 770RF104 interaction. Inhibition of interaction by a canadidate inhibitor is measured by preincubating the sensor chip with a candidate inhibitor prior to adding P77ORF104 protein. A decrease in P77ORF104 binding is indicative of competitive binding by the candidate compound.

ii) Fluorescence Resonance Energy Transfer (FRET)

Another method of measuring inhibition of binging of two proteins uses fluorescence resonance energy transfer FRET (de Angelis, 1999, Physiological Genomics).

FRET is a quantum mechanical phenomenon that occurs between a fluorescence donor (D) and a fluorecence acceptor (A) in close proximity (usually<100 A of separation.) if the emission spectrum of D overlaps with the excitation spectrum of A. Variants of the green fluorescent protein (GFP) from the jellyfish *Aequorea victoria* is fused to protein and serve as D-A pairs in a FRET scheme to measure protein-protein interaction. Cyan (CFP: D) and yellow (YFP: A) fluorescence proteins are linked with DnaI polypeptide and 770RF104 protein respectively. Under optimal proximity, interaction between DnaI and P77ORF104 causes a decrease in intensity of CFP concomitant with an increase in YFP fluorescence.

The addition of a candidate modulator to the mixture of appropriately labeled DnaI and P77ORF104 protein, will result in an inhibition of energy transfer evidenced by, for example, a decease in YFP fluorescence at a given concentration of P77ORF104 relative to a sample without the candidate inhibitor.

iii) Fluorescence Polarization

In addition to the surface plasmon resonance and FRET methods, fluorescence polarization measurement is useful to quatitate protein-protein binding.

The fluorescence polarization value for a fluorescently-tagged molecule depends on the rotational correlation time or tumbling rate. Protein complexes, such as those formed by *S. aureus* DnaI polypeptide associating with fluorescence labeled polypeptide (e.g., *S. aureus* DnaC, P77ORF104 or a binding fragment thereof), labeled to comprise a fluorescently-labeled molecule have higher polarization values than a fluorescently labeled monomeric protein. Inclusion of a candidate inhibitor of the DnaI interaction results in a decrease in fluorescence polarization relative to a mixture without candidate inhibitor if the candidate inhibitor disrupts or inhibits the interaction of DnaI with its polypeptide binding partner. It is preferred that this method be used to characterize small molecules that disrupt polypeptide complexes.

iv) Scintilliation Proximity Assay

A scintillation proximity assay may be used to characterize the interaction between an association of *S. aureus* DnaI polypeptide and another polypeptide. *S. aureus* DnaI polypeptide can be coupled to beads. Addition of radio-labeled P77ORF104 results in binding where the radioactive source molecule is in close proximity to the scintillation fluid. Thus, signal is emitted upon P77ORF104 polypeptide binding, and compounds that prevent *S. aureus* DnaI polypeptide association with P77ORF104 diminish the signal scintillation.

v. Bio Sensor Assay

ICS biosensors have been described by AMBRI (Australian Membrane Biotechnology Research Institute). They couple the self-association of macromolecules to the closing of gramacidin-facilitated ion channels in suspended membrane bilayers and hence to a measurable change in the admittance (similar to impedence) of the biosensor. This approach is linear over six decades of admittance change and is ideally suited for large scale, high through-put screening of small molecule combinatorial libraries.

b. Assays of DnaI Activity i. Assay for DNA Replication, $^3$H-thymidine Incorporation To measure the effect of 770RF104 expression on *S. aureus* DNA replication, the level of radiolabeled thymidine incorporation into DNA is measured in the presence or in the absence of sodium arsenite (5 uM). Samples (0.5 ml) are withdrawn from the cultures at appropriate time intervals and mixed to 4.5 ul of labeling solution (0.2 uCi/ml of $^3$H-thymidine (73 Ci/mmol, NEN Life Science Products, Inc) and 70 pmol of cold thymidine). After 15 min of reaction,, incorporation is stopped by adding solution containing 0.2% $NaN_3$ and 1 mM cold thymidine. Samples are precipitated with 10% w/v trichloroacetic acid and filtered through glass fiber filters (GF-C, Whatman). The results are expressed as $^3$H-thymidine counts incorporated normalized to OD culture.

The assay is performed in the presence of varying concentrations of candidate inhibitors in place of P77 ORF104 to screen for inhibitors. At least a 10-fold reduction in $^3$H-thymidine incorporation in the presence of P77 ORF104 or other inhibitor indicates a reduction in DnaI activity.

ii: Plasmid Replication

The plasmid pC194 replicates in *S. aureus* by rolling circle mechanism. The single stranded origin, sso of the pC194 is involved in the synthesis of the lagging DNA strand. The plasmid pADG6406 is a derivative of pC 194 lacking sso. The absence of sso leads the the accumulation of plasmid single-stranded DNA. The single-stranded initiation site, ssiA, is located on the lagging strand of pAM 1 and is a site for primosome assembly. SsiA was inserted into plasimd pADG6404. *S aureus* harboring plasmids are grown to mid-log phase and their total DNA is extracted and analyzed by Southern hybirdization, using $^{32}$P-labelled plasmid DNA as probe. The presence of pADG6406n with ssiA is associated to a decrease in the ratio of ss to ds DNA compared to that of the plasmid without ssiA. This system is used to measure the effect of 77ORF104 an candidate inhibitor polypeptides expression on ss DNA synthesis. A plasmid containing 77ORF104 or a candidate inhibitor polypeptide coding sequence under an arsenite inducible promotor will be insert into *S aureus* harboring pADG6406. The ratio of ss to ds DNA of pADG6406 is measured in the presence or in the absence of sodium arsenite (5 uM). An increase in the ratio of ss to ds DNA (10% or more) indicates an effect of the candidate modulator.

In another aspect, the present invention relates to a screening kit for identifying agonists, antagonists, ligands, receptors, substrates, enzymes, etc. for a polypeptide and/or polynucleotide of the present invention; or compounds which decrease or enhance the production of such polypeptides and/or polynucleotides, which comprises: (a) a polypeptide and/or a polynucleotide of the present invention; (b) a recombinant cell expressing a polypeptide and/or polynucleotide of the present invention; (c) a cell membrane expressing a polypeptide and/or polynucleotide of the present invention; or (d) antibody to a polypeptide and/or polynucleotide of the present invention; which polypeptide is preferably that of SEQ ID NO:2, and which polynucleotide is preferably that of SEQ ID NO:1.

It will be appreciated that in any such kit, (a), (b), (c) or (d) may comprise a substantial component.

It will be readily appreciated by the skilled artisan that a polypeptide and/or polynucleotide of the present invention may also be used in a method for the structure-based design of an agonist, antagonist or inhibitor of the polypeptide and/or polynucleotide, by: (a) determining in the first instance the three-dimensional structure of the polypeptide and/or polynucleotide, or complexes thereof; (b) deducing the three-dimensional structure for the likely reactive site(s), binding site(s) or motif(s) of an agonist, antagonist or inhibitor; (c) synthesizing candidate compounds that are predicted to bind to or react with the deduced binding site(s), reactive site(s), and/or motif(s); and (d) testing whether the candidate compounds are indeed agonists, antagonists or inhibitors. It will be further appreciated that this will normally be an iterative process, and this iterative process may be performed using automated and computer-controlled steps.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host that is responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial dnaI proteins that mediate tissue damage and/or; to block the normal progression of pathogenesis in infections initiated other than by the implantation of in-dwelling devices or by other surgical techniques.

In accordance with yet another aspect of the invention, there are provided dnaI antagonists, preferably bacteriostatic or bacteriocidal antagonists.

The antagonists of the invention may be employed, for instance, to prevent, inhibit and/or treat diseases.

Compositions, Kits and Administration

In a further aspect of the invention there are provided compositions comprising a dnaI polynucleotide and/or a *S. aureus* DnaI polypeptide for administration to a cell or to a multicellular organism.

The present invention provides for pharmaceutical compositions comprising a therapeutically effective amount of a polypeptide and/or polynucleotide, such as the soluble form of a polypeptide and/or polynucleotide of the present invention, antagonist peptide or small molecule compound, in combination with a pharmaceutically acceptable carrier or excipient. Such carriers include, but are not limited to, saline, buffered saline, dextrose, water, glycerol, ethanol, and combinations thereof. The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation. Alternative means for systemic administration include transmucosal and transsdermal administration using penetrants such as bile salts or fusidic acids or other detergents, In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

As used herein, the term "in-dwelling device" refers to surgical implants, prosthetic devices and catheters, i.e., devices that are introduced to the body of an individual and remain in position for an extended time. Such devices include, but are not limited to, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *S. aureus* wound infections.

Many orthopedic surgeons consider that humans with prosthetic joints should be considered for antibiotic prophylaxis before dental treatment that could produce a bacteria. Deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis Alternatively, the composition of the invention may be used to bathe an indwelling device immediately before insertion. The active agent will preferably be present at a concentration of 1 mg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Sequence Databases, Sequences in a Tangible Medium and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as GCC.

The polynucleotide and polypeptide sequences of the invention are particularly useful as components in databases useful for search analyses as well as in sequence analysis algorithms. As used in this section entitled "Sequence Databases, Sequences in a Tangible Medium, and Algorithms," and in claims related to this section, the terms "polynucleotide of the invention" and "polynucleotide sequence of the invention" mean any detectable chemical or physical characteristic of a polynucleotide of the invention that is or may be reduced to or stored in a tangible medium, preferably a computer readable form. For example, chromatographic scan data or peak data, photographic data or scan data therefrom, called bases, and mass spectrographic data. As used in this section entitled Databases and Algorithms and in claims related thereto, the terms "polypeptide of the invention" and "polypeptide sequence of the invention" mean any detectable chemical or physical characteristic of a polypeptide of the invention that is or may be reduced to or stored in a tangible medium, preferably a computer readable form. For example, chromatographic scan data or peak data, photographic data or scan data therefrom, and mass spectrographic data.

The invention provides a computer readable medium having stored thereon polypeptide sequences of the invention and/or polynucleotide sequences of the invention. The computer readable medium can be any composition of matter used to store information or data, including, for example, commercially available floppy disks, tapes, chips, hard drives, compact disks, and video disks.

In a preferred embodiment of the invention there is provided a computer readable medium having stored thereon a member selected from the group consisting of: a polynucleotide comprising the sequence of SEQ ID NO:1; a polypeptide comprising the sequence of SEQ ID NO:2; a set of polynucleotide sequences wherein at least one of said sequences comprises the sequence of SEQ ID NO:1; a set of polypeptide sequences wherein at least one of said sequences comprises the sequence of SEQ ID NO:2; a data set representing a polynucleotide sequence comprising the sequence of SEQ ID NO:1; a data set representing a polynucleotide sequence encoding a polypeptide sequence comprising the sequence of SEQ ID NO:2; a polynucleotide comprising the sequence of SEQ ID NO:1; a polypeptide comprising the sequence of SEQ ID NO:2; a set of polynucleotide sequences wherein at least one of said sequences comprises the sequence of SEQ ID NO:1; a set of polypeptide sequences wherein at least one of said sequences comprises the sequence of SEQ ID NO:2; a data set representing a polynucleotide sequence comprising the sequence of SEQ ID NO:1; a data set representing a polynucleotide sequence encoding a polypeptide sequence comprising the sequence of SEQ ID NO:2.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLE 1

Identification of a *S. aureus* Protein Targeted by Bacteriophage 77 ORF 104

To identify *S. aureus* proteins that interact with Staphylococcus bacteriophage 77 ORF 104, a GST-fusion of ORF 104 was generated and the recombinant protein purified and utilized to make a GST/ORF104 affinity column. Cellular extracts prepared from *S. aureus* cells were incubated with the affinity matrix, washed with increasing salt concentrations and different detergents, and the protein elution profile of the washes assessed by SDS-polyacrylamide gel electrophoresis. A protein of molecular mass~40 kDa was specifically eluted from the affinity matrix. Eluted proteins were further characterized to determine the identity of the interacting protein and to validate the interaction of the protein with ORF 104 as described in detail below.

A. Generation of GST/ORF 104 Recombinant Protein

Figure 7A:
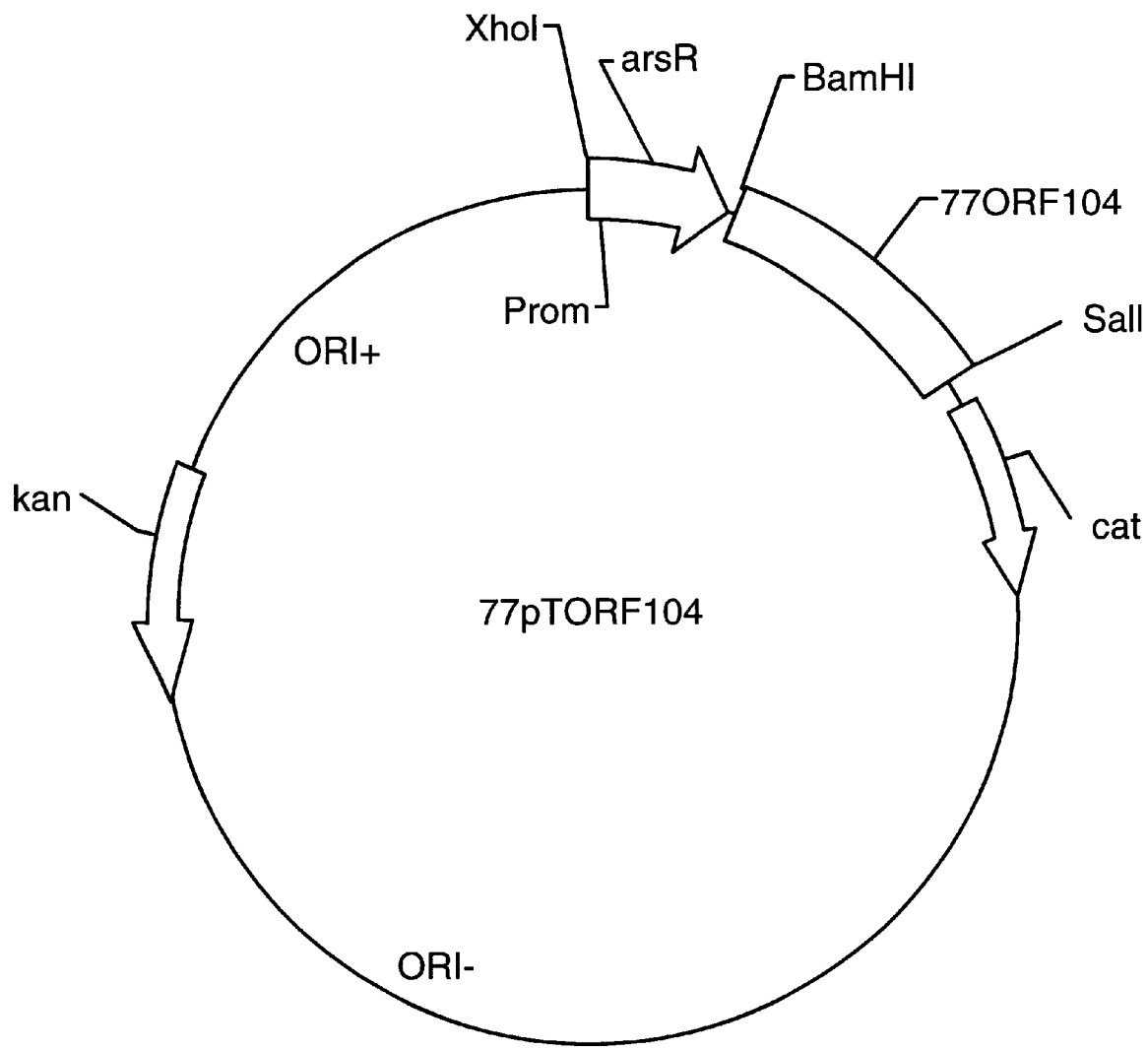
FIGS. 7A–7C shows the killing potential of bacteriophage ORF 104 and the expression vector used to induce its expression in *S. aureus*: (A) schematic diagram of expression vector pT/ORF used to induce expression of ORF 104 in *S. aureus* cells; (B) the results of a screen to assess killing potential of ORF104 when expressed in *S. aureus* on semi-solid support media; and (C) the results of a screen to assess killing potential of ORF104 when expressed in *S. aureus* in liquid media.
Figure 7B:
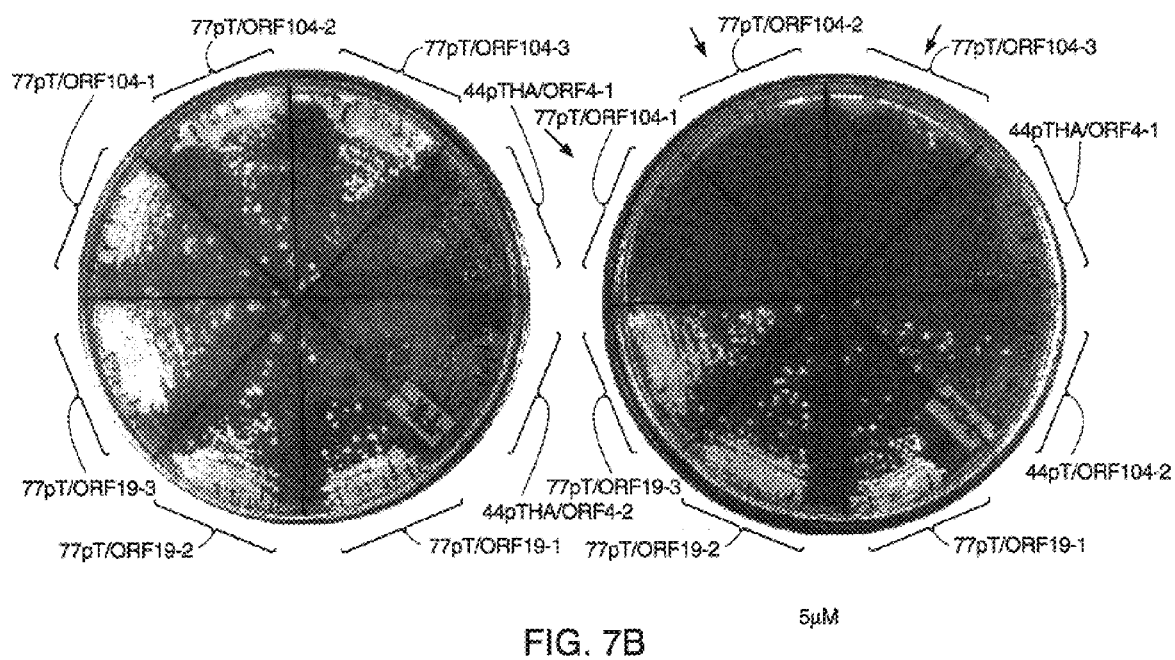
Figure 7C:
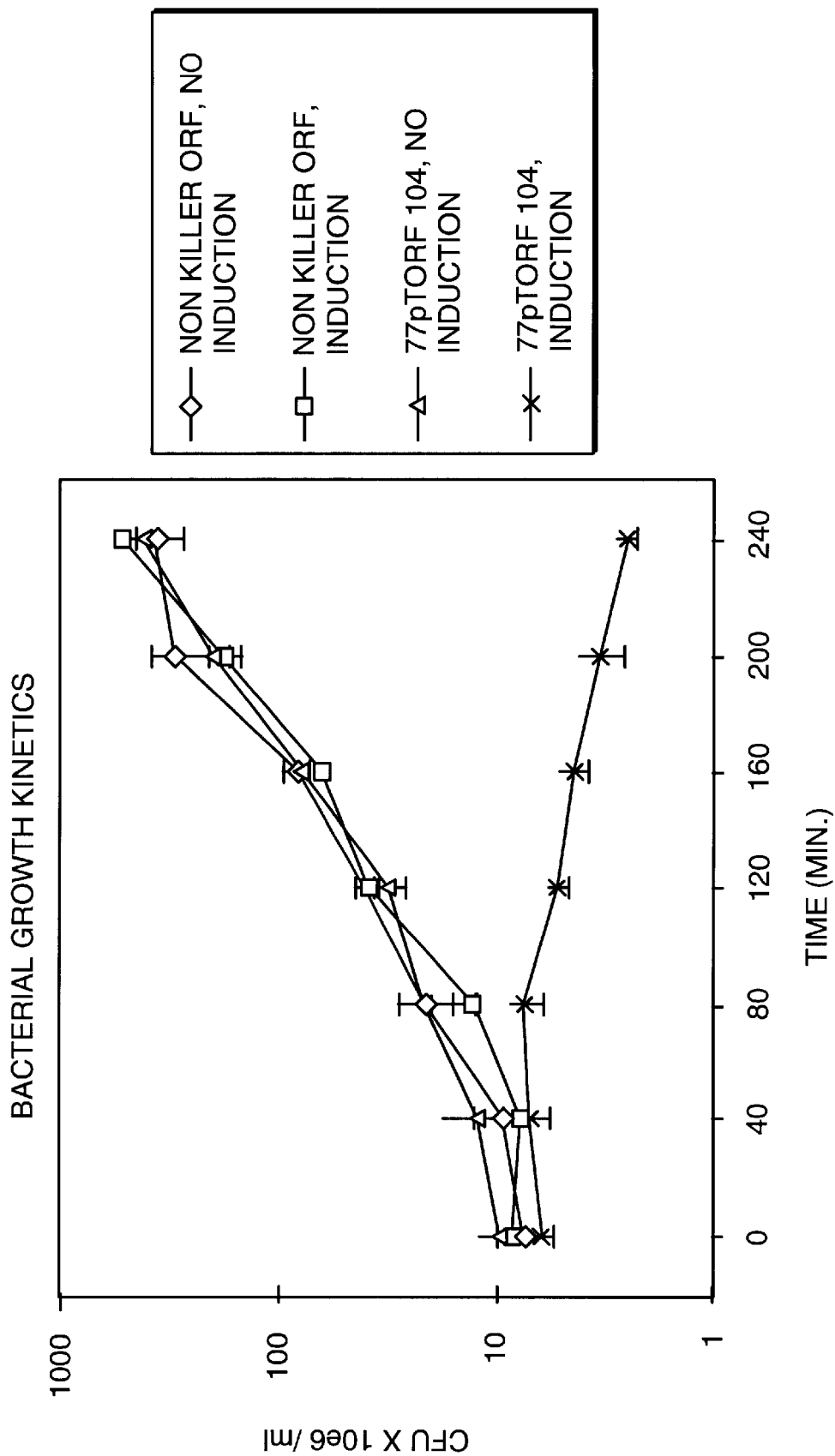
Figure 8A:
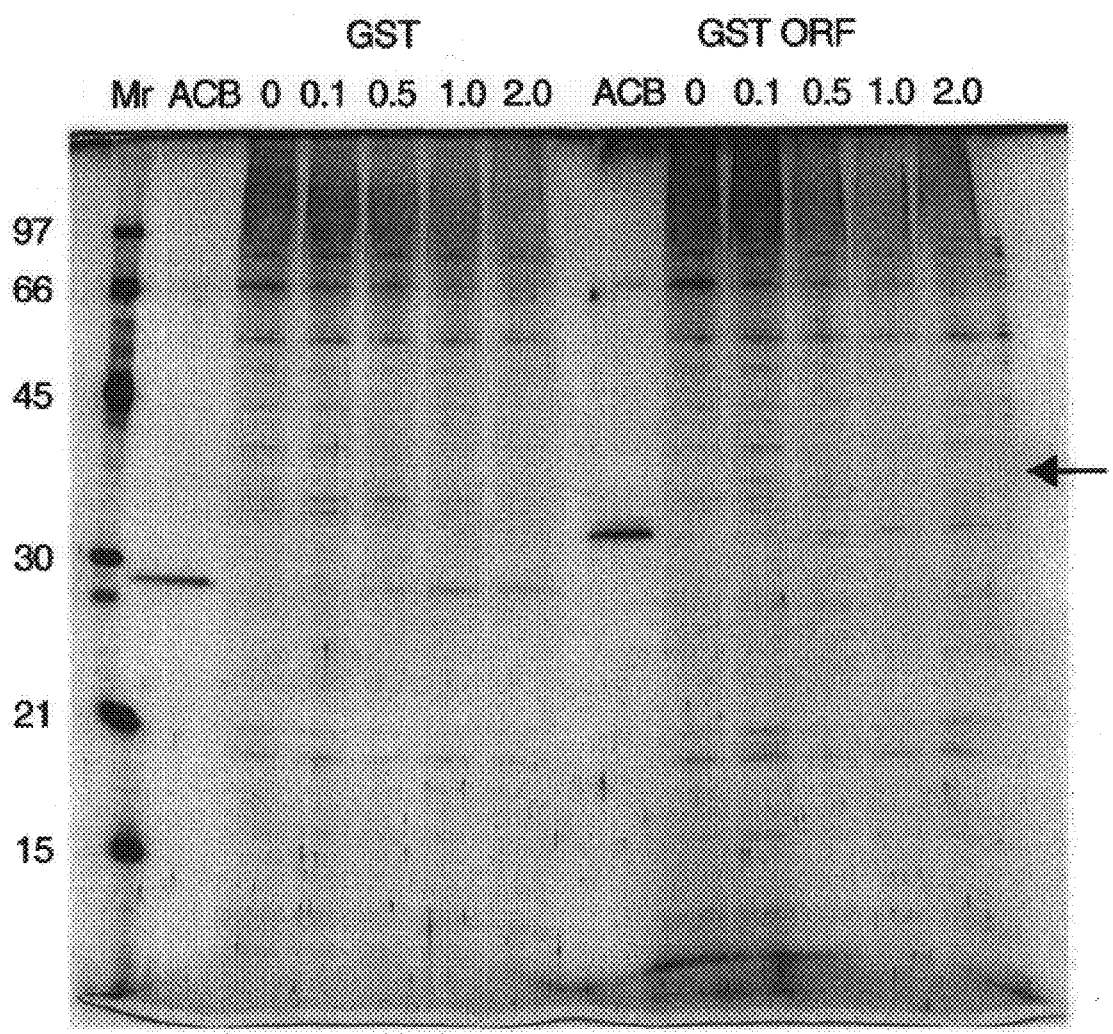
FIGS. 8A–8D shows affinity chromatography using GST and GST/ORF104 as ligands with the *S. aureus* extract prepared by French pressure cell lysis and sonication. Eluates from affinity columns containing the GST and GST/ORF104 ligands at 0, 0.1, 0.5, 1.0, and 2.0 mg/ml resin were resolved by 12.5% SDS-PAGE. Proteins were visualized by silver staining. Micro-columns were eluted with: A) ACB containing 1% Triton X-100; B) 250 mM NaCl; C) 1 M NaCl; and D) 1% SDS. Each molecular weight marker is approximately 100 ng. The lanes labeled ACB indicate eluates from a 2.0 mg/ml ligand column loaded only with ACB buffer containing 75 mM NaCl. The arrows indicate bands specifically interacting with GST/ORF104.
Figure 8B:
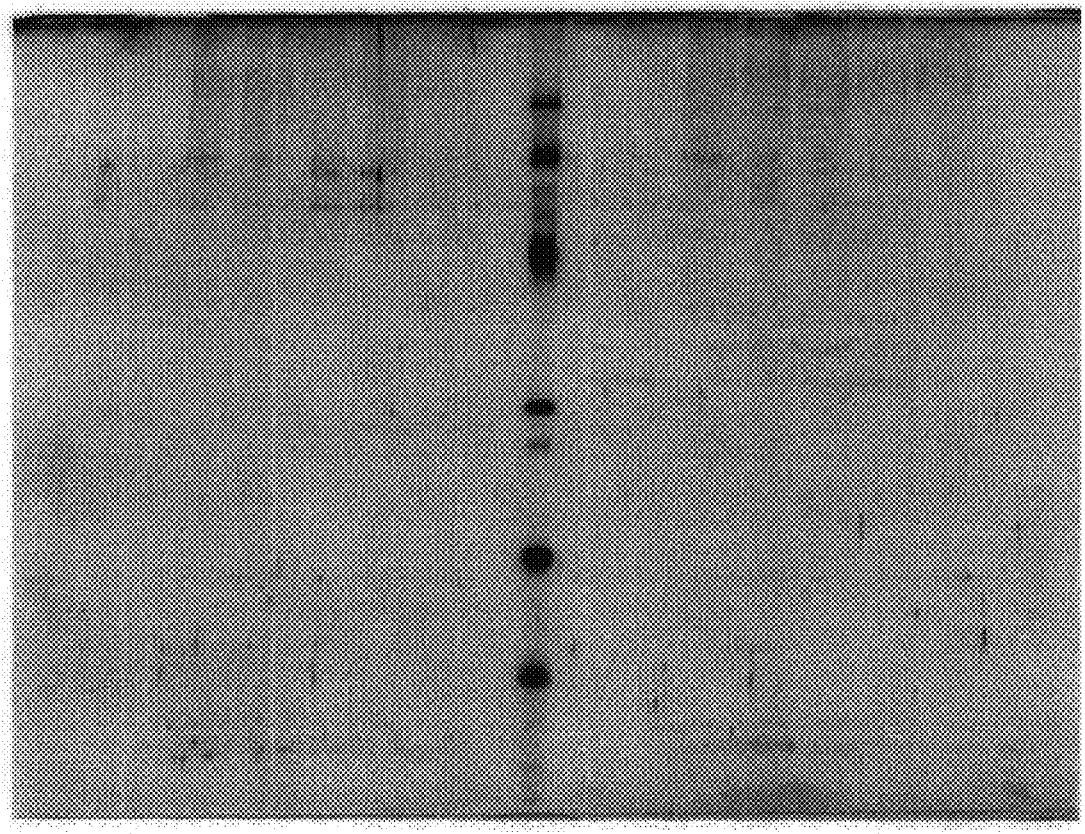
Figure 8C:
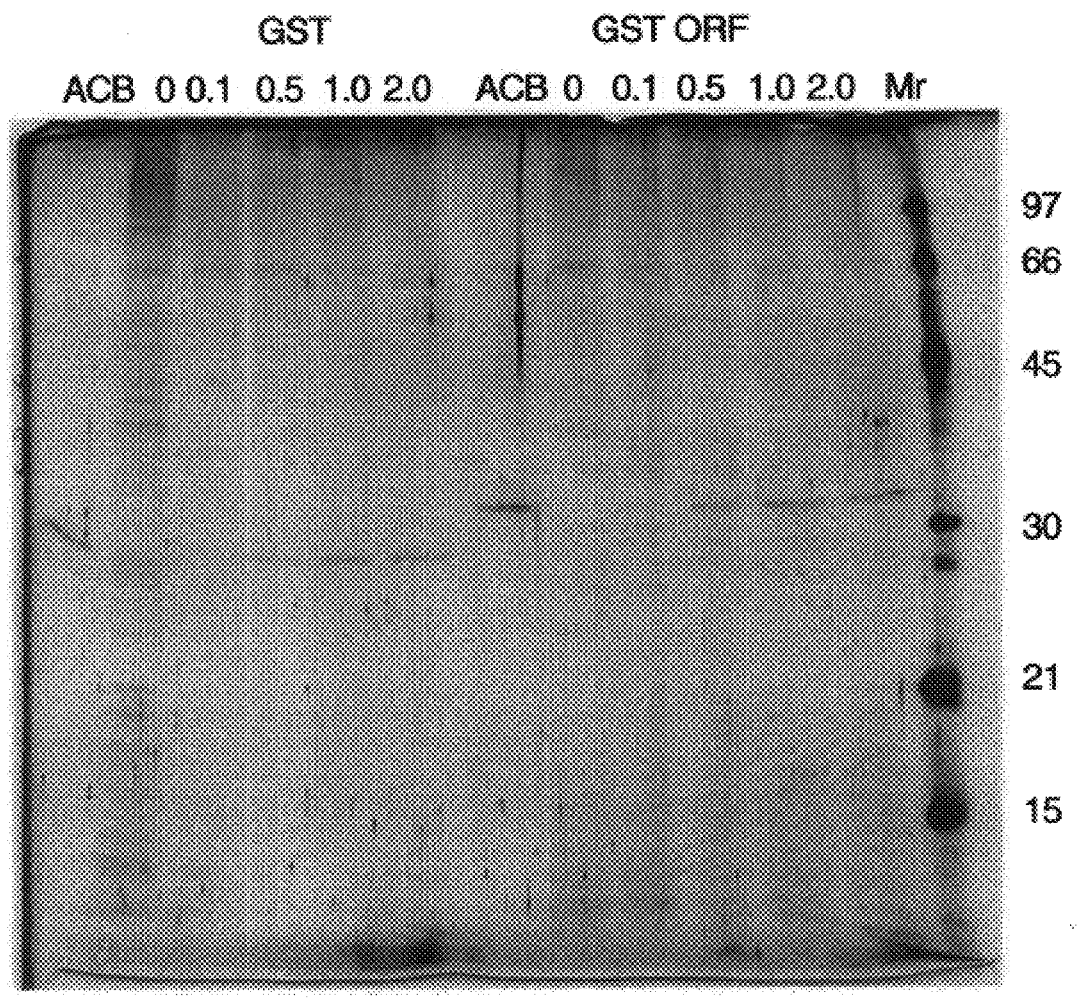
Figure 8D:
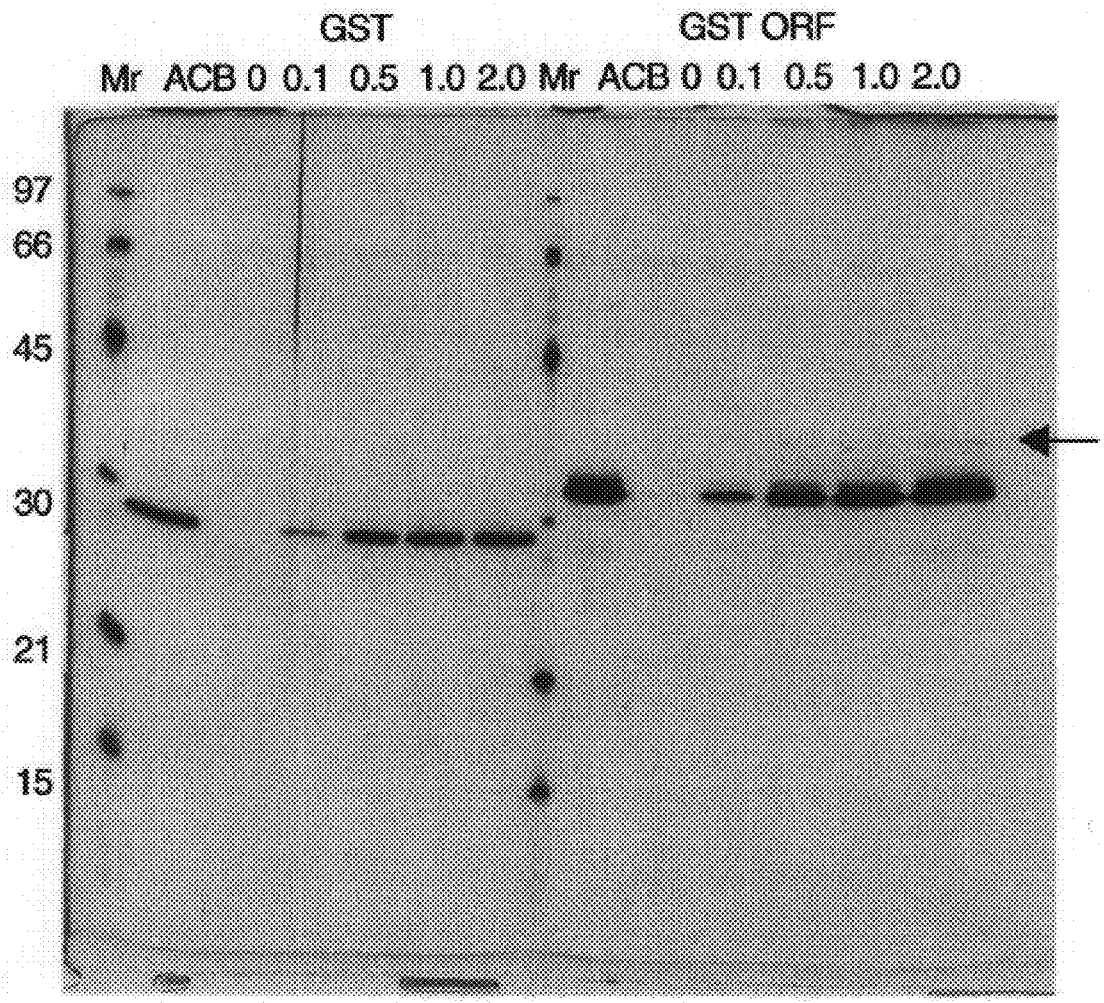

Bacteriophage ORF104 was sub-cloned into pGEX 4T-1 (Pharmacia), an expression vector containing the GST moiety. The gene encoding ORF104 was obtained by digestion of pT/ORF104 (FIG. 7A) with Bam HI and Sal I. The DNA fragment containing ORF104 was gel purified by QiaQuick spin column (Qiagen) and ligated into pGEX 4T-1 (which had been previously digested with Bam HI and Sal I) to generate pGEX 4T/ORF104. Recombinant expression vectors were identified by restriction enzyme analysis of plasmid minipreps, large-scale DNA preparations were performed with Qiagen columns, and the resulting plasmid was sequenced. Test expressions in *E. coli* DH5 cells containing the expression plasmids were performed to identify optimal protein expression conditions. *E. coli* DH5 cells containing the pGEX 4T/ORF104 were grown in Luria-Bertani Broth at 37° C. to an $OD_{600}$ of 0.4 to 0.6 and induced with 1 mM IPTG at 30° C. for 4 hrs.

B. Fusion Protein Purification

Cells containing GST/ORF104 fusion protein were suspended in 20 ml lysis buffer/liter of cell culture with GST lysis buffer (20 mM Hepes pH 7.2, 500 mM NaCl, 10% glycerol, 1 mM DTT, 1 mM EDTA, 1 mM benzamidine, and 1 PMSF) and lysed by French Pressure cell followed by three bursts of twenty seconds with an ultra-sonicator at 4° C. Triton X-100 was added to the lysate to a final concentration of 0.1% and mixed for 30 minutes at 4° C. The lysate was centrifuged at 4° C for 30 minutes at 10 000 rpm in a Sorval SS34 rotor. The supernatant was applied to a 4 ml glutathione sepharose column pre-equilibrated with lysis buffer and allowed to flow by gravity. The column was washed with 10 column volumes of lysis buffer and eluted in 1.5 ml fractions with GST elution buffer (20 mM Hepes pH 8.0, 500 mM NaCl, 10% glycerol, 1 mM DTT, 0.1 mM EDTA, and 25 mM reduced glutathione). The fractions were analyzed by 12.5% SDS-PAGE (Laemmli) and visualized by staining with Coomassie Brilliant Blue R250 stain to assess the amount of eluted GST/ORF104 protein.

GST/ORF104 (12 mg) was dialyzed overnight against 20 mM Hepes pH 7.5, 150 mM NaCl, 10% glycerol, 1 mM DTT, 0.1 mM EDTA, made up to 2.5 mM $CaCl_2$ and digested with bovine thrombin at a mass ratio of 1:10 (thrombin : GST ORF104) for 2.5 hrs at 28 ° C. to cleave the GST domain from the ORF104 domain. The digestion was stopped by the addition of 1 mM PMSF, 1 mM benzamidine, and NaCl to a 1M final concentration. The digested protein was applied to a one ml glutathione sepharose column and flow-through fractions of 1 ml were collected. The fractions were analyzed by 12% SDS-PAGE (Tricine) and visualized by staining with Coomassie Brilliant Blue R250 stain to determine which fractions contain bacterially expressed ORF104 lacking the GST tag.

C. Affinity Column Preparation

GST and GST/ORF104 fusion protein were dialyzed overnight against ACB containing 1 M NaCl. ORF104 protein obtained from thrombin digestion of GST/ORF104 was used without dialysis. Protein concentrations were determined by Bio-Rad Protein Assay and crosslinked to Affigel 10 resin (Bio-Rad) at protein/resin concentrations of 0, 0.1, 0.5, 1.0, and 2.0 mg/ml. The crosslinked resin was sequentially incubated in the presence of ethanolamine, and bovine serum albumin (BSA) prior to column packing and equilibration with ACB containing 75 mM NaCl.

D. *S. aureus* Extract Preparation

Two extracts were prepared from *S. aureus* cell pellets. One lysate was prepared by French Pressure cell followed by sonication, and the other by a lysostaphin digestion followed by sonication. The French Pressure cell prepared lysate was prepared by suspending 3 g of frozen *S. aureus* cells in Affinity Chromatography Buffer (ACB; 20 mM Hepes pH 7.5, 10% glycerol, 1 mM DTT, and 1 mM EDTA) containing 500 mM NaCl, 1 mM PMSF, and 1 mM benzamidine. The suspended cells were subjected to three passes through the French Pressure cell followed by 3 sonication bursts of 20 seconds each, made up to 0.1% Triton X-100, stirred for 30 minutes, and centrifuged at 50 000 rpm for 3 hrs in a Ti70 fixed angle Beckman rotor. The efficiency of cell lysis was low and the resulting lysate (7 ml) contained 2.4 mg/ml protein. The cell pellet after the French Pressure cell lysis was subjected to cryogenic grinding in liquid nitrogen in the same buffer with a mortar and pestle. The lysate was made up to 0.1% Triton X-100, stirred for 30 minutes, and centrifuged at 50 000 rpm for 3 hrs in a Ti70 fixed angle Beckman rotor yielding a lysate (10 ml) containing 2.0 mg/ml protein. The cell lysates were found to be similar by SDS-PAGE and were pooled, concentrated to 8 ml, and dialyzed overnight in a 3000 Mr dialysis membrane against affinity chromatography containing 1 mM PMSF, 1 mM benzamidine, and 75 mM NaCl. The dialyzed protein extract was removed from the dialysis tubing, centrifuged at 10000 rpm in a Sorval SS34 rotor for 1 hr, and assayed for protein content (Bio-Rad Protein Assay) and salt concentration (conductivity meter).

The second lysate was prepared by lysostaphin digestion followed by sonication. A *S. aureus* cell pellet (2.9 g) was suspended in 8 ml of 20 mM Hepes pH 7.5, 150 mM NaCl, 10% glycerol, 1 mM DTT, 1 mM PMSF, 1 mM benzamidine, and 1000 units of lysostaphin. The cell suspension was incubated at 37° C. for 30 minutes, cooled to 4° C., and made up to a final concentration of 1 mM EDTA and 500 mM NaCl. The lysate was sonicated on ice using three bursts of 20 seconds each. The lysate was made up to 0.1% Triton X-100, stirred for 30 minutes, and centrifuged at 50 000 rpm for 3 hrs in a Ti70 fixed angle Beckman rotor. The supernatant was removed and dialyzed overnight in a 3000 Mr dialysis membrane against ACB containing 75 mM NaCl, 1 mM benzamidine, and 1 mM PMSF. The dialyzed protein extract was removed from the dialysis tubing, centrifuged at 10 000 rpm in a Sorval SS34 rotor for 1 hr, and assayed for protein content (utilizing the Bio-Rad Protein Assay) and salt concentration (utilizing a conductivity meter). Aliquots of the extracts were frozen at −70° C.

E. Affinity Chromatography

*S. aureus* extract (400 µl) was applied to 40 µl columns containing 0, 0.1. 0.5. 1.0, and 2.0 mg/ml ligand and ACB containing 75 mM NaCl (400 µ) was applied to an additional column containing 2.0 mg/ml ligand. The columns were washed with ACB containing 75 mM NaCl (400 µl) and sequentially eluted with ACB containing 1% Triton X-100 and 75 mM NaCl (160 µl), ACB containing 250 mM NaCl (160 µl), ACB containing 1M NaCl (160µl), and 1% SDS (160 µl). 40 µl of each eluate was resolved by 16 cm 12.5% SDS-PAGE (Laemmli) and the eluted proteins were visualized by silver stain (FIGS. 8 and 9).

F. Identification of *S. aureus* DnaI Homolog as an ORF104 Interacting Protein

Proteins at approximately 38 kDa were observed specifically in the eluants from the GST/ORF104 and ORF104

Figure 9:
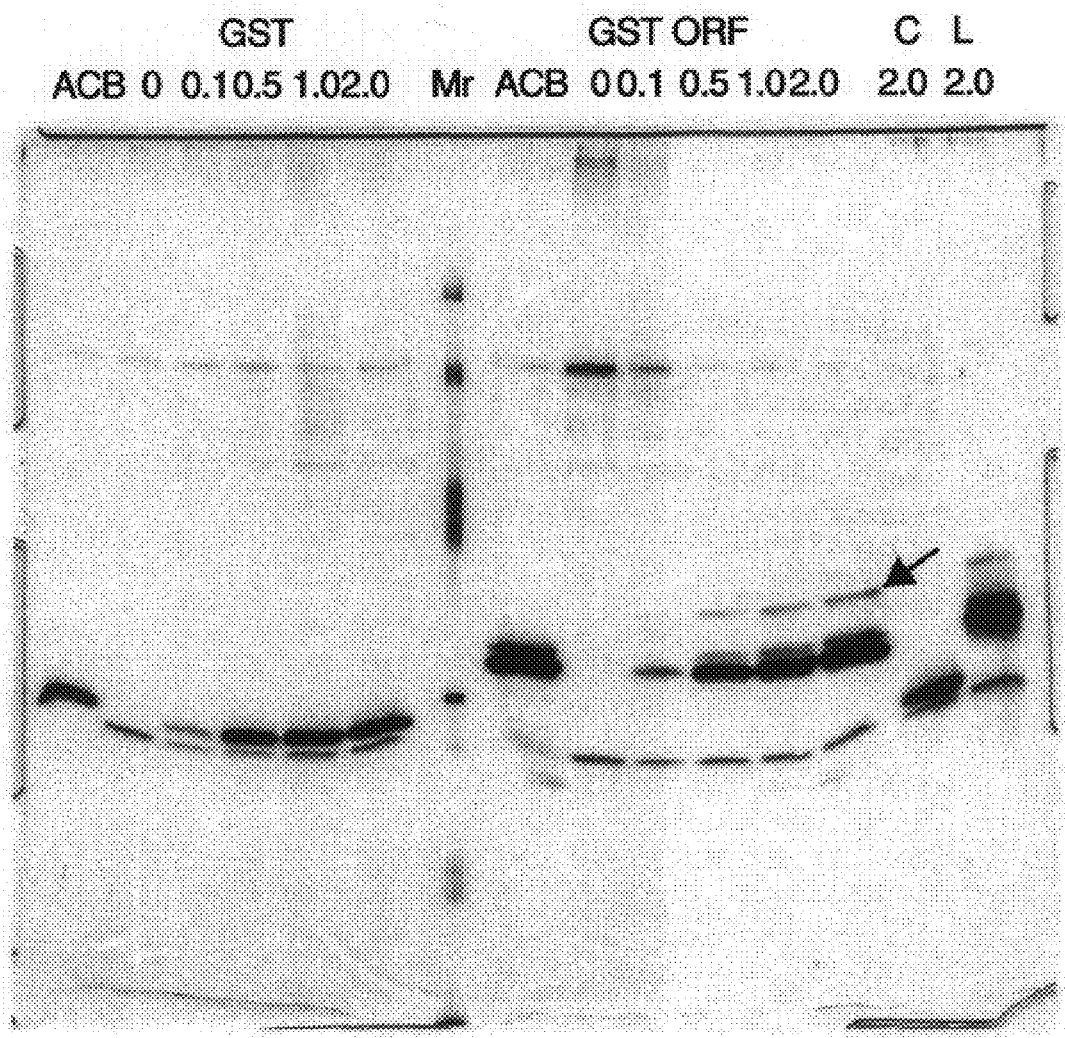
FIG. 9 shows affinity chromatography with GST and GST/ORF104 as ligands with the *S. aureus* extract prepared by lysis with lysostaphin digestion and sonication. Eluates from affinity columns containing the GST and GST ORF104 ligands at 0, 0.1, 0.5, 1.0, and 2.0 mg/ml resin were resolved by 12.5% SDS-PAGE. Micro-columns were sequentially eluted with 75 mM ACB containing 1% Triton X-100, 250 mM NaCl, 1 M NaCl ACB, and 1% SDS. The elution profile obtained with 1% SDS is shown. Each molecular weight marker is approximately 100 ng. The lanes labeled ACB indicate eluates from a 2.0 mg/ml ligand column loaded only with ACB buffer containing 75 mM NaCl. Lanes labeled C and L are corresponding elutions from columns containing GST and GST/ORF104 at 2.0 mg/ml from FIG. 8. The arrow indicates a polypeptide specifically interacting with GST/ORF104.
Figure 10:
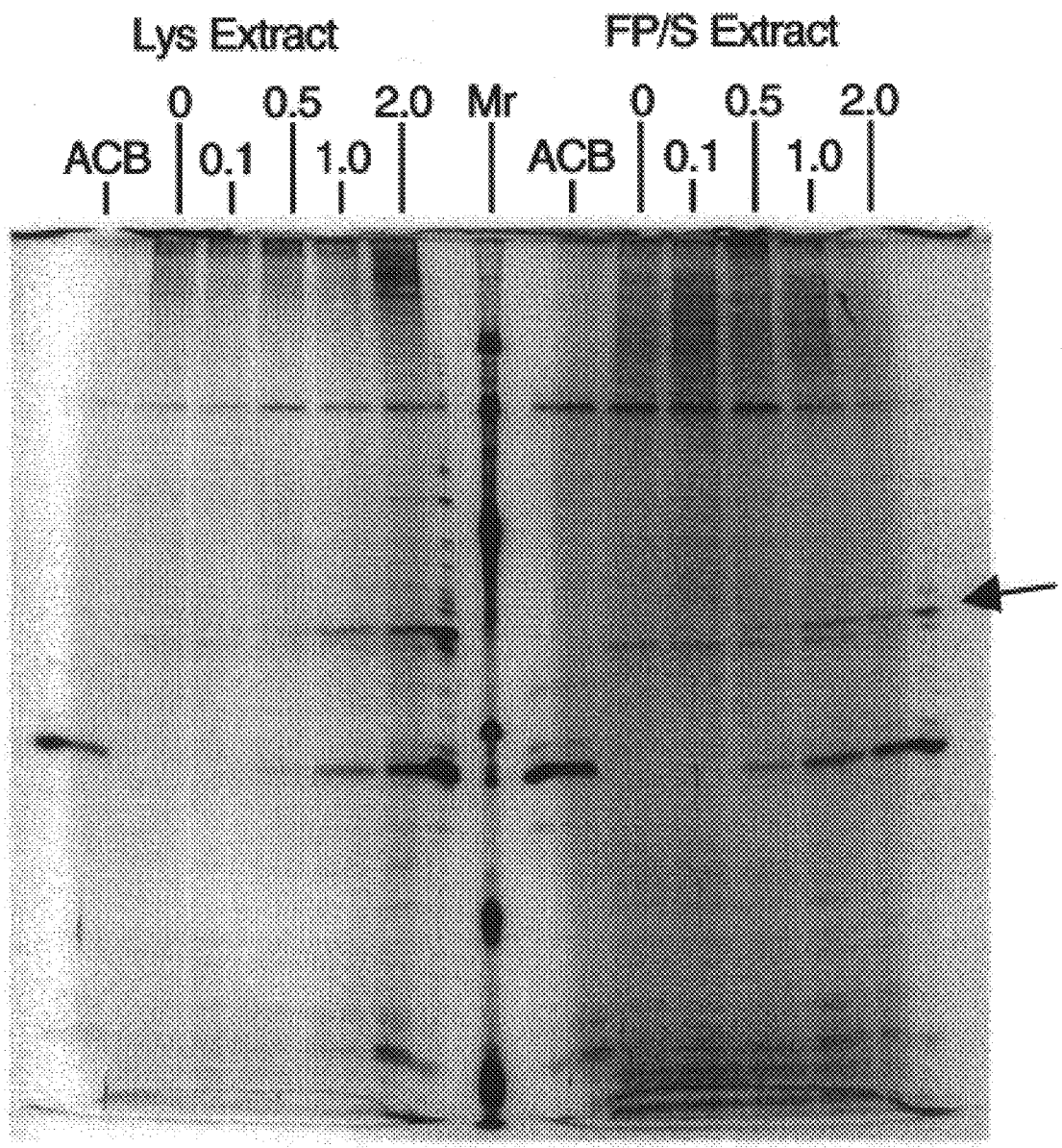
FIG. 10 shows affinity chromatography with ORF104 (GST removed) as ligand with the *S. aureus* extract prepared by lysis with lysostaphin digestion and sonication (Lys extract) and French pressure cell and sonication (FP/S extract). Eluates from affinity columns containing the ORF104 ligand at 0, 0.1, 0.5, 1.0, and 2.0 mg/ml resin were resolved by 12.5% SDS-PAGE and the gel was stained with silver nitrate. Micro-columns were sequentially eluted with: A) ACB containing 1% Triton X-100; B) 250 mM NaCl; C) 1M NaCl; and D) 1% SDS. The elution profile obtained with 1% SDS is shown. Each molecular weight marker is approximately 100 ng. The lanes labeled ACB indicate eluates from a 2.0 mg/ml ligand column loaded only with ACB buffer containing 75 mM NaCl. The arrow indicates a polypeptide specifically interacting with GST/ORF104.
Figure 11A:
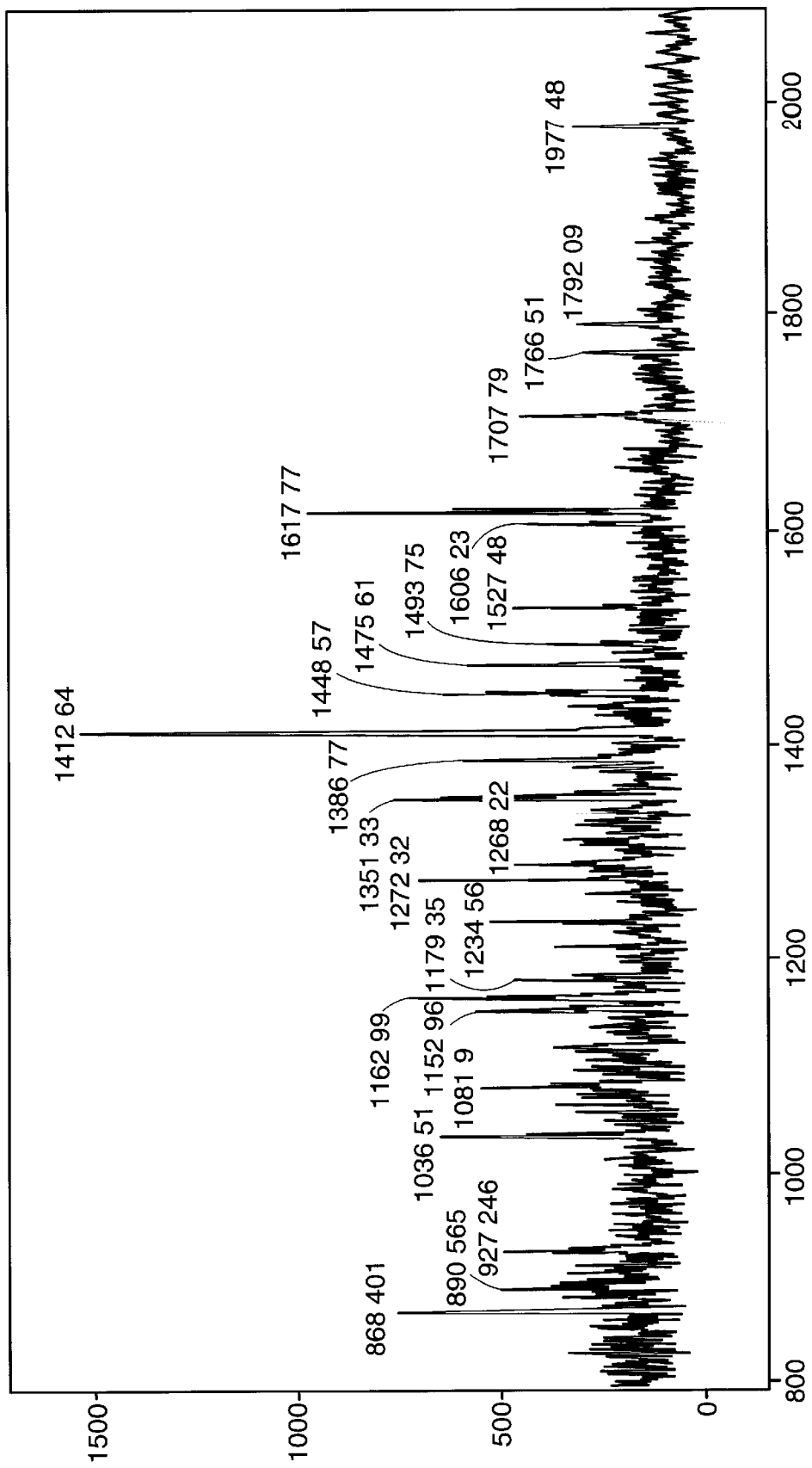
FIG. 11 shows results of a tryptic peptide mass spectrum analysis showing relatedness between the interacting protein eluted with Triton X-100 (indicated by arrow in FIG. 8C) and the interacting protein eluted with 1% SDS (indicated by arrow in FIG. 8D). Of note are the tryptic peptides having monoisotopic MH+ masses of 1351.8, 1412.7, and 1617.8 Da.
Figure 11B:
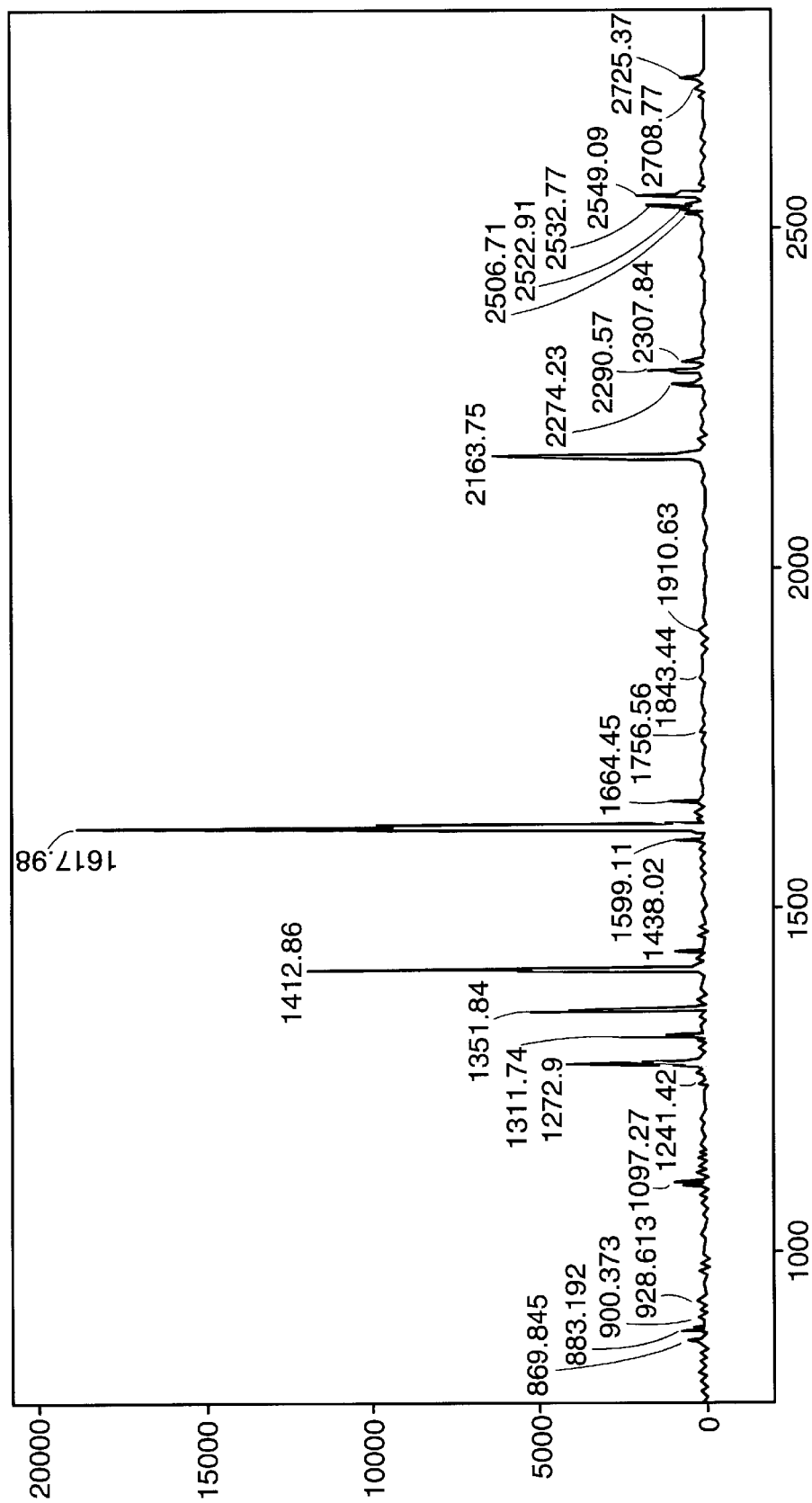

(GST removed) columns obtained from ACB containing 75 mM NaCl and 1% Triton X-100, and 1% SDS (FIGS. 8–10; eluting protein indicated by an arrow). These bands were excised from the SDS-PAGE gels and prepared for tryptic peptide mass determination by MALDI-ToF mass spectrometry (Qin, J., Fenyo, D., Zhao, Y., Hall, W. W., Chao, D. M., Wilson, C. J., Young, R. A. and Chait, B. T. (1997) *Anal. Chem.* 69, 3995–4001). High quality mass spectra were obtained (FIG. 11). The candidate proteins observed in the two eluants were identical as determined by the masses of the tryptic peptides (FIG. 11). Post-Source Decay (PSD) coupled with Collision-Induced Decay (CID) was used to obtain fragmentation spectra of tryptic peptides having monoisotopic MH+ masses of 1351.8, 1412.7, and 1617.8 Da. The fragment masses were used to search all public domain databases resulting in no identification. The PSD/CID spectra obtained for the peptide having a monoisotopic MH+ mass of 1412.7 were then interpreted to obtain a peptide sequence GHVPENVTDNDR (SEQ ID NO:10), which was used to BLAST search the *S. aureus* nucleotide sequence database at http://www.genome.ou.edu/staph.html. One nucleotide sequence, Contig 981, in reading frame +3 encoded the similar amino acid sequence GHVPELYVDNNR (SEQ ID NO:11). This tentative identification of the candidate protein was then confirmed upon conceptual translation and in silico tryptic digestion of the open reading frame found in Contig 981. Furthermore, the obtained PSD/CID spectra for tryptic peptides with monoisotopic MH+ masses of 1351.8 and 1617.8 Da were similar to the predicted PSD/CID fragmentation patterns of the tryptic peptides with monoisotopic MH+ masses of 1351.8 and 1617.8 Da found in the Contig 981 open reading frame. Comparison of the Contig 981 open reading frame with all other sequences in the public domain databases revealed that Contig 981 is a homologue of *Bacillus subtilis* DnaI, a protein involved in origin-dependent DNA replication (42% identity and 62% similarity) (Table 1 SEQ ID NO:14).

G. Yeast Two-hybrid Confirmation of DnaI and ORF 104 Interaction.

To validate the identification of the *S. aureus* dnaI homolog as an interacting partner of Bacteriophage 77 ORF 104, the interaction was assessed in vivo in the yeast two hybrid system.

Figure 12A:
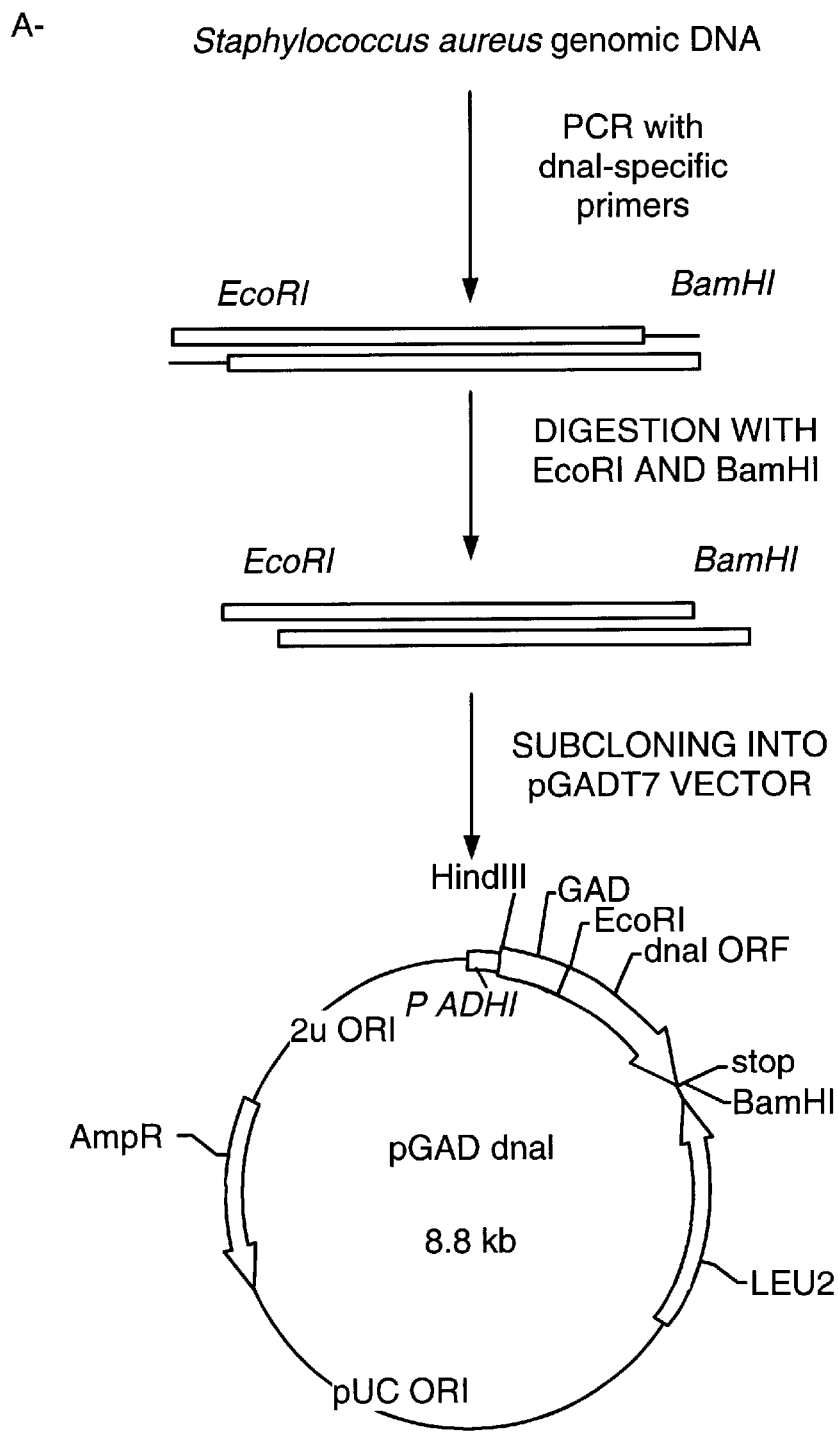
Figure 12B:
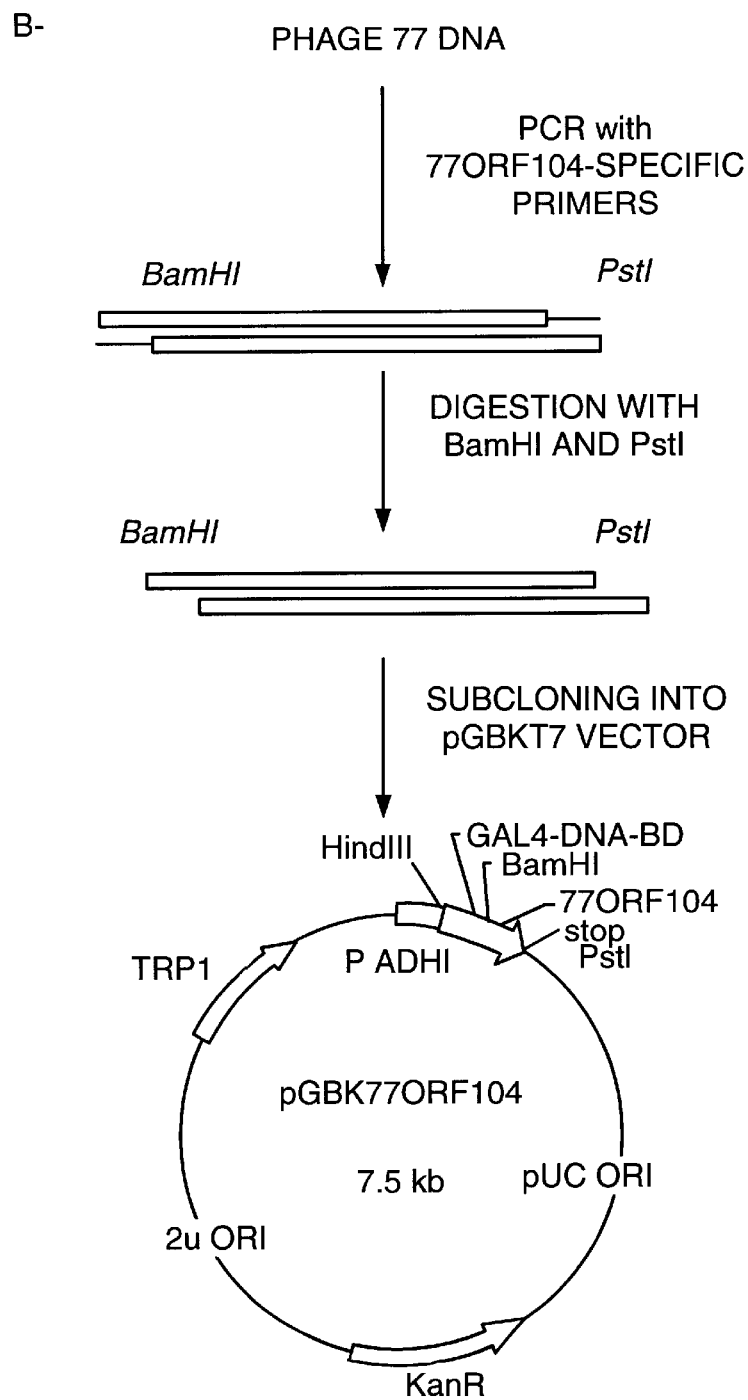
Figure 12E:
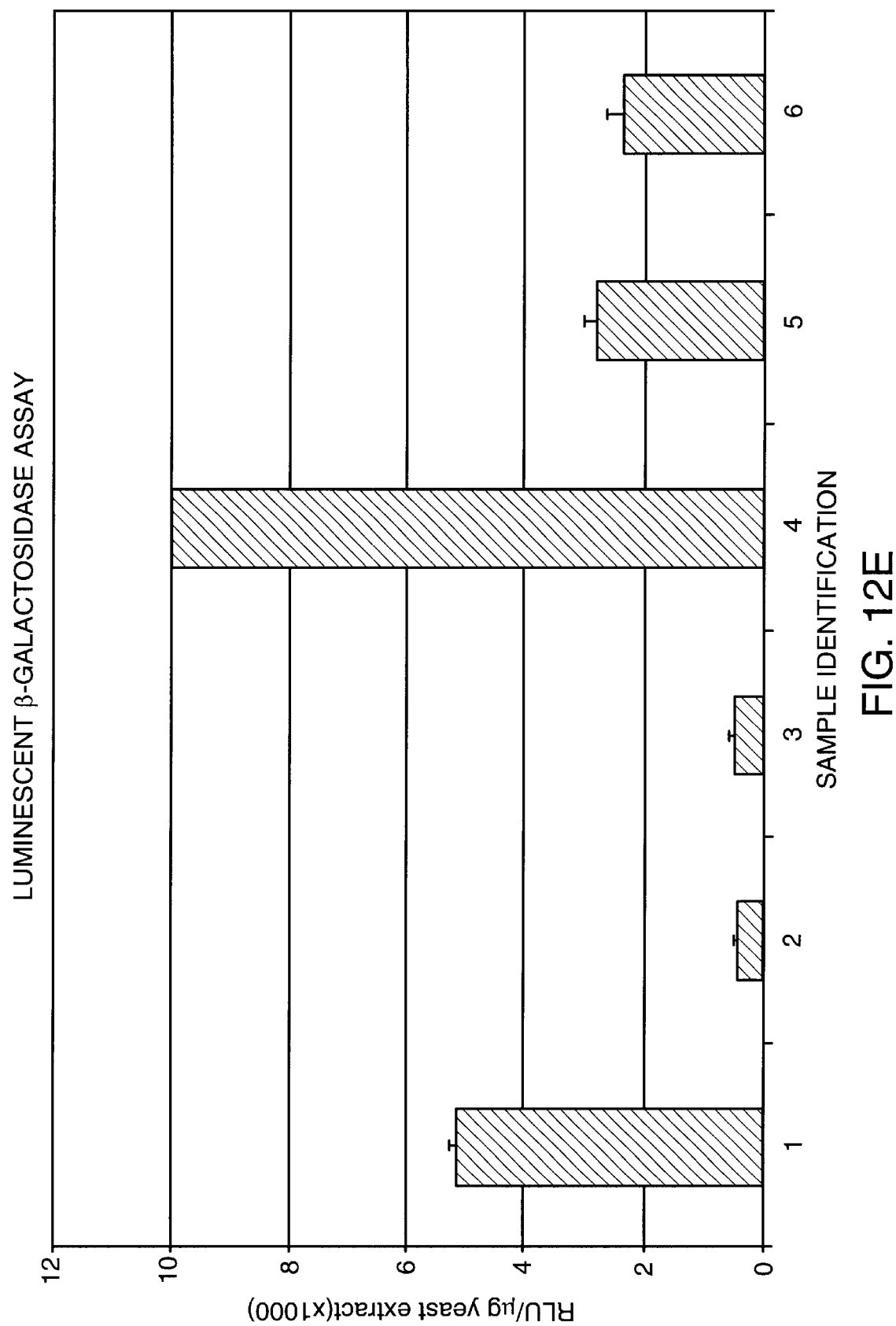

Bacteriophage ORF 104 was fused to the carboxyl terminus of the yeast Gal4 activation domain II (amino acids 768–881) to create a bait vector. The polynucleotide sequence of the DnaI homologue was isolated from the *S. aureus* genome by PCR utilizing oligonucleotide primers that targeted the translation initiation and termination codons of the dnaI gene. This dnaI polynucleotide fragment was sequenced and engineered into a plasmid, in frame, with the DNA binding domain of Gal4. These two plasmids were introduced alone, or in combination, into yeast cells previously engineered with chromosomally integrated copies of the *E. coli* lacZ and the selectable HIS3 genes, both under Gal4 regulation. When the two proteins expressed in yeast interact, the resulting complex will activate transcription from promoters containing Gal4 binding sites. A lacZ and His3 gene, each driven by a promoter containing Gal4 binding sites, have been integrated into the genome of the host yeast system used for measuring protein-protein interactions. Such a system provides a physiological environment in which to detect potential protein interactions. In such a system, both Dna I and bacteriophage 77 ORF 104 was found to interact, since the introduction of both plasmids into Y190 resulted in the production of the lacZ and His3 genes (FIG. 12). Induction of these reporter genes is dependent upon the interaction of both proteins since when either expressed plasmid is individually introduced into yeast host cells, no reporter expression is observed (FIG. 12). These results are consistent with the interpretation that the *S. aureus* DnaI homologue identified herein is the host target of bacteriophage 77 ORF104. In addition, switching the environment of the DnaI and ORF 104, such that DnaI is now in the bait plasmid and ORF 104 is in the prey plasmid, produced similar results.

OTHER EMBODIMENTS

Other embodiments are within the following claims.

What is claimed is:

1. An isolated polypeptide comprising the amino acid sequence of SEQ ID NO:2.

2. An isolated polypeptide consisting of the amino acid sequence of SEQ ID NO:2.

3. An isolated and purified DnaI polypeptide comprising at least 50% identity to the amino acid sequence of SEQ ID NO:2, wherein said polypeptide has an activity selected from the group consisting of:
   a) directly interacting with bacteriophage 77 ORF 104 protein or a DnaI-binding fragment thereof in a manner that results in at least 10 fold reduction of $^3$H-thymidine incorporation in a bacterial DNA replication assay relative to $^3$H-thymidine incorporation in an assay lacking bacteriophage 77 ORF 104 protein or a DnaI-binding fragment thereof;
   b) directly interacting with bacteriophage 77 ORF 104 protein or a DnaI-binding fragment thereof in a manner that results in at least 10% inhibition of plasmid replicaiton by bacteriophage 77 ORF 104 protein or a DnaI-binding fragment in a plasmid replication assay; and
   c) aids in the loading of *S. aureus* DnaC helicase onto replicative primosomes.

4. An isolated and purified DnaI polypeptide comprising at least 60% identity to the amino acid sequence of SEQ ID NO:2, wherein said polypeptide has an activity selected from the group consisting of:
   a) directly interacting with bacteriophage 77 ORF 104 protein or a DnaI-binding fragment thereof in a manner that results in at least 10 fold reduction of $^3$H-thymidine incorporation in a bacterial DNA replication assay relative to $^3$H-thymidine incorporation in an assay lacking bacteriophage 77 ORF 104 protein or a DnaI-binding fragment thereof;
   b) directly interacting with bacteriophage 77 ORF 104 protein or a DnaI-binding fragment thereof in a manner that results in at least 10% inhibition of plasmid by bacteriophage 77 ORF 104 protein or a DnaI-binding fragment in a plasmid replication assay; and
   c) aids in the loading of *S. aureus* DnaC helicase onto replicative primosomes.

5. An isolated and purified DnaI polypeptide comprising at least 70% identity to the amino acid sequence of SEQ ID NO:2, wherein said polypeptide has an activity selected from the group consisting of:
   a) directly interacting with bacteriophage 77 ORF 104 protein or a DnaI-binding fragment thereof in a manner that results in at least 10 fold reduction of $^3$H-thymidine incorporation in a bacterial DNA replication assay relative to $^3$H-thymidine incorporation in an assay lacking bacteriophage 77 ORF 104 protein or a DnaI-binding fragment thereof;
   b) directly interacting with bacteriophage 77 ORF 104 protein or a DnaI-binding fragment thereof in a manner that results in at least 10% inhibition of plasmid by bacteriophage 77 ORF 104 protein or a DnaI-binding fragment in a plasmid replication assay; and
   c) aids in the loading of *S. aureus* DnaC helicase onto replicative primosomes.

6. An isolated and purified DnaI polypeptide comprising SEQ ID NO:2 or fragments thereof, wherein said fragments have an activity selected from the group consisting of:
   a) directly interacting with bacteriophage 77 ORF 104 protein or a DnaI-binding fragment thereof in a manner that results in at least 10 fold reduction of $^3$H-thymidine incorporation in a bacterial DNA replication assay relative to $^3$H-thymidine incorporation in an assay lacking bacteriophage 77 ORF 104 protein or a DnaI-binding fragment thereof;
   b) directly interacting with bacteriophage 77 ORF 104 protein or a DnaI-binding fragment thereof in a manner that results in at least 10% inhibition of plasmid by bacteriophage 77 ORF 104 protein or a DnaI-binding fragment in a plasmid replication assay; and
   c) aids in the loading of *S. aureus* DnaC helicase onto replicative primosomes.

\* \* \* \* \*

SEQUENCE LISTING

<160> NUMBER OF SEQ ID NOS: 15

<210> SEQ ID NO 1
<211> LENGTH: 942
<212> TYPE: DNA
<213> ORGANISM: Staphylococcus aureus

<400> SEQUENCE: 1

```
atgggaggag gacagtcaat aatgaagcaa tttaaaagta taattaacac gtcgcaggac      60
tttgaaaaaa gaatagaaaa gataaaaaaa gaagtaatca atgacccaga tgttaagcaa     120
tttttggaag cgcatcgagc tgaattaacg aatgctatga ttgatgaaga cttaaatgtg     180
ttacaagagt ataaagatca acaaaaacat tatgacggtc ataaatttgc tgattgtcca     240
aatttcgtaa aggggcatgt gcctgagtta tatgttgata ataccgaat taaaatacgc      300 tatttacaat gcccatgtaa aatcaagtac gacgaagaac gctttgaagc tgagctaatt     360
acatctcatc atatgcaacg agatacttta aatgccaaat tgaaagatat ttatatgaat     420
catcgagacc gtcttgatgt agctatggca gcagatgata tttgtacagc aataactaat     480
ggggaacaag tgaaaggcct ttacctttat ggtccatttg ggacaggtaa atcttttatt     540
```

```
ctaggtgcaa ttgcgaatca gctcaaatct aagaaggtac gttcgacaat tatttattta    600
ccggaattta ttagaacatt aaaaggtggc tttaaagatg gttcttttga aaagaaatta    660
catcgcgtaa gagaagcaaa cattttaatg cttgatgata ttgggctga  agaagtgact    720 ccatgggtga gagatgaggt aattggacct ttgctacatt atcgaatggt tcatgaatta    780
ccaacattct ttagttctaa ttttgactat agtgaattgg aacatcattt agcgatgact    840
cgtgatggtg aagagaagac taaagcagca cgtattattg aacgtgtcaa atctttgtca    900
acaccatact ttttatcagg agaaaatttc agaaacaatt ga                      942
```

<210> SEQ ID NO 2
<211> LENGTH: 313
<212> TYPE: PRT
<213> ORGANISM: Staphylococcus aureus

<400> SEQUENCE: 2

```
Met Gly Gly Gly Gln Ser Ile Met Lys Gln Phe Lys Ser Ile Ile Asn
1               5                   10                  15

Thr Ser Gln Asp Phe Glu Lys Arg Ile Glu Lys Ile Lys Lys Glu Val
            20                  25                  30

Ile Asn Asp Pro Asp Val Lys Gln Phe Leu Glu Ala His Arg Ala Glu
        35                  40                  45

Leu Thr Asn Ala Met Ile Asp Glu Asp Leu Asn Val Leu Gln Glu Tyr
    50                  55                  60

Lys Asp Gln Gln Lys His Tyr Asp Gly His Lys Phe Ala Asp Cys Pro
65                  70                  75                  80

Asn Phe Val Lys Gly His Val Pro Glu Leu Tyr Val Asp Asn Asn Arg
                85                  90                  95

Ile Lys Ile Arg Tyr Leu Gln Cys Pro Cys Lys Ile Lys Tyr Asp Glu
            100                 105                 110

Glu Arg Phe Glu Ala Glu Leu Ile Thr Ser His His Met Gln Arg Asp
        115                 120                 125

Thr Leu Asn Ala Lys Leu Lys Asp Ile Tyr Met Asn His Arg Asp Arg
    130                 135                 140

Leu Asp Val Ala Met Ala Ala Asp Asp Ile Cys Thr Ala Ile Thr Asn
145                 150                 155                 160

Gly Glu Gln Val Lys Gly Leu Tyr Leu Tyr Gly Pro Phe Gly Thr Gly
                165                 170                 175

Lys Ser Phe Ile Leu Gly Ala Ile Ala Asn Gln Leu Lys Ser Lys Lys
            180                 185                 190

Val Arg Ser Thr Ile Ile Tyr Leu Pro Glu Phe Ile Arg Thr Leu Lys
        195                 200                 205

Gly Gly Phe Lys Asp Gly Ser Phe Glu Lys Lys Leu His Arg Val Arg
    210                 215                 220

Glu Ala Asn Ile Leu Met Leu Asp Asp Ile Gly Ala Glu Glu Val Thr
225                 230                 235                 240

Pro Trp Val Arg Asp Glu Val Ile Gly Pro Leu Leu His Tyr Arg Met
                245                 250                 255

Val His Glu Leu Pro Thr Phe Phe Ser Ser Asn Phe Asp Tyr Ser Glu
            260                 265                 270

Leu Glu His His Leu Ala Met Thr Arg Asp Gly Glu Glu Lys Thr Lys
        275                 280                 285

Ala Ala Arg Ile Ile Glu Arg Val Lys Ser Leu Ser Thr Pro Tyr Phe
    290                 295                 300
```

Leu Ser Gly Glu Asn Phe Arg Asn Asn
305                 310

<210> SEQ ID NO 3
<211> LENGTH: 41708
<212> TYPE: DNA
<213> ORGANISM: Staphylococcus aureus

<400> SEQUENCE: 3

| | | | | |
|---|---|---|---|---|
| gatcaaaata cttggggaac ggttagggag taaacttcgc gataatttta aaaattcatg | | | | 60 |
| tataaccccc ctcttataac cattttaagg caggtgatga aatggagatt atagtcgatg | | | | 120 |
| aaaatttagt gcttaaagaa aaagaaaggc tacaagtatt atataaagac atacctagca | | | | 180 |
| ataaattaaa agtagttgat ggtttaatta ttcaagcagc aaggctacgt gtaatgcttg | | | | 240 |
| attacatgtg ggaagacata aaagaaaaag gtgattatga tttatttact caatctgaaa | | | | 300 |
| aggcgccacc atatgaaagg gaaagaccag tagccaaact atttaatgct agagatgctg | | | | 360 |
| catatcaaaa ataatcaaa caattatcgg atttattgcc cgaagagaaa gaagacacag | | | | 420 |
| aaacgccatc tgatgattac ctatgattag taataaatac gttgatgaat atataaattt | | | | 480 |
| gtggaaacaa ggaagataa ttttaaataa agaaagaatt gatctcttta attatctaca | | | | 540 |
| aaaacatata tattcacgag atgatgtata ttttgatgaa cagaaaatcg aggattgtat | | | | 600 |
| caaatttatt gaaaaatggt attttccaac attaccattt caaaggttta tcatagctaa | | | | 660 |
| tatatttctt atagataaaa atacagatga agctttcttt acagaatttg ctattttcat | | | | 720 |
| gggacgtgga ggcgggaaaa acggtctaat aagtgctatt agtgattttc tttctacgcc | | | | 780 |
| cttacacgga gttaaagaat atcacatctc cattgttgct aatagtgaag atcaagcaaa | | | | 840 |
| aacatcgttt gatgaaatca gaaccgtttt aatggataac aaacgaaata agacgggtaa | | | | 900 |
| aacgccaaaa gctccttatg aagttagtaa agcaaaaata ataaaccgtg caactaaatc | | | | 960 |
| ggttattcga tataacacat caaacacaaa aaccaaagac ggtggacgtg aggggtgtgt | | | | 1020 |
| tattttttgat gaaattcatt atttctttgg tcctgaaatg gtaaacgtca aacgtggtgg | | | | 1080 |
| attaggtaaa aagaaaaata gaagaacgtt ttatataagt actgatggtt tgttagaga | | | | 1140 |
| gggttatatc gatgcaatga agcacaaaat tgcaagtgta ttaagtggca aggttaaaaa | | | | 1200 |
| tagtagattg tttgcttttt attgtaagtt agacgatcca aaagaagttg atgacagaca | | | | 1260 |
| gacgtgggaa aaggcgaacc caatgttaca taaaccgtta tcagaatacg ctaaaacact | | | | 1320 |
| gctaagcacg attgaagaag aatataacga tttaccattc aaccgttcaa ataagcccga | | | | 1380 |
| attcatgact aagcgaatga atttgcctga agttgacctt gaaaaagtaa tagcaccatg | | | | 1440 |
| gaaagaaata ctagcgacta atagagagat accaaattta gataatcaaa tgtgtattgg | | | | 1500 |
| tggtttagac tttgcaaaca ttcgagattt tgcaagtgta gggctattat tccgaaaaaa | | | | 1560 |
| cgatgattac atttggttag gacattcgtt tgtaagacaa gggttttttgg atgatgtcaa | | | | 1620 |
| attagaacct cctattaaag aatgggaaaa aatgggatta ttgaccattg tcgatgatga | | | | 1680 |
| tgtcattgaa attgaatata tagttgattg gttttttaaag gctagagaaa aatatgggct | | | | 1740 |
| tgaaaaagtc atagctgata attatagaac tgatattgta agacgtgcgt ttgaggatgc | | | | 1800 |
| tggcataaaa cttgaagtac ttagaaatcc aaaagcaata catggattac ttgcaccacg | | | | 1860 |
| tatcgataca atgtttgcga aacataacgt aatatatgga gacaatcctt tgatgcgttg | | | | 1920 |
| gtttactaat aatgttgctg taaaaatcaa gccggatgga aataaagagt atatcaaaaa | | | | 1980 |
| agatgaagtc agacgtaaaa cggatggatt catggctttt gttcacgcat tatatagagc | | | | 2040 |

-continued

```
agacgatata gtagacaaag acatgtctaa agcgcttgat gcattaatga gtatagattt    2100
ctaatagagg aggtgagaca tgagtattct agaaaagata tttaaaacta ggaaagatat    2160
aacatatatg cttgatttag atatgataga agatctatca caacaagcgt atgtgaaacg    2220
tttagcgatt gatagttgta ttgaatttgt tgcgcgagct gtcgctcaaa gtcattttaa    2280
agtattggaa ggtaatagaa ttcaaaagaa tgatgtttac tacaagttaa atataaaacc    2340
aaatactgac ttatcaagcg atagttttg gcaacaagtt atatataaac taatttatga    2400
taacgaggtt ttaatcgtag taagtgacag caaagaatta cttatcgcag atagctttta    2460
cagagaagag tacgctttgt atgatgatat attcaaagat gtaacggtta aagattatac    2520
ttatcaacgt actttcacaa tgcaagaggt catatattta aagtacaaca acaataaagt    2580
gacacacttt gtagaaagtc tattcgaaga ttacgggaaa atattcggaa gaatgatagg    2640
tgcacaatta aaaactatc aaataagagg gattttgaaa tctgcctcta gcgcatatga    2700
cgaaaagaat atagaaaaat tacaagcgtt cacaaataaa ttattcaata cttttaataa    2760
aaatcaacta gcaatcgcgc ctttgataga aggttttgat tatgaggaat tatctaatgg    2820
tggtaagaat agtaacatgc cttttttctga attgagtgag ctaatgagag atgcaataaa    2880
aaatgttgcg ttgatgattg gtatacctcc aggtttgatt tacggagaaa cagctgattt    2940 ggaaaaaac acgcttgtat tgagaagtt ctgtttaaca cctttattaa aaaagattca    3000
gaacgaatta aacgcgaaac tcataacaca aagcatgtat ttgaaagata caagaataga    3060
aattgtcggt gtgaataaaa aagacccact tcaatatgct gaagcaattg acaaacttgt    3120
aagttctggt tcatttacaa ggaatgaggt gcggattatg ttaggtgaag aaccatcaga    3180
caatcctgaa ttagacgaat acctgattac taaaaactac gaaaaagcta acagtggtga    3240
aaatgatgaa aaagaaaaag atgaaaacac tttgaaaggt ggtgatgaag atgaaagcgg    3300
agattaaagg cgtcatcgtt tccaacgaag ataaatgggt ttacgaaatg cttggtatgg    3360
attcgacttg tcctaaagat gttttaacac aactagaatt tagtgatgaa gatgttgata    3420
ttataattaa ctcaaatggt ggtaacctag tagctggtag tgaaatatat acacatttaa    3480
gagctcataa aggcaaagtg aatgttcgta tcacagcaat agcagcaagt gcggcatcgc    3540
ttatcgcaat ggctggtgac cacatcgaaa tgagtccggt tgctagaatg atgattcaca    3600
atccttcaag tattgcgcaa ggagaagtga agatctaaa tcatgctgca gaaacattag    3660
aacatgttgg tcaaataatg gctgaggcat atgcggttag agctggtaaa aacaaacaag    3720
aacttataga aatgatggct aaggaaacgt ggctaaatgc tgatgaagcc attgaacaag    3780
gttttgcgga tagtaaaatg tttgaaaacg acaatatgca aattgtagca agcgatacac    3840
aagtgttatc gaaagatgta ttaaatcgtg taacagcttt ggtaagtaaa acgccagagg    3900
ttaacattga tattgacgca atagcaaata agtaattga aaaataaat atgaaagaaa    3960 aggaatcaga aatcgatgtt gcagatagta aattatcagc aaatggattt tcaagattcc    4020
ttttttaata caaaaatagg aggtcataaa atgactataa atttatcgga acattcgca    4080 aatgcgaaaa acgaatttat taatgcagta acaacggtg aaccgcaaga aagacaaaat    4140
gaattgtacg gtgacatgat taaccaacta tttgaagaaa ctaaattaca agcaaaagca    4200
gaagctgaaa gagtttctag tttacctaaa tcagcacaaa ctttgagtgc aaaccaaaga    4260 aatttctttta tggatatcaa taagagtgtt ggatataaag aagaaaaact tttaccagaa    4320
gaaacaattg atagaatctt cgaagattta acaacgaatc atccattatt agctgactta    4380
```

```
ggtattaaaa atgctggttt gcgtttgaag ttcttaaaat ccgaaacttc tggcgtggct    4440
gtttggggta aaatctatgg tgaaattaaa ggtcaattag atgctgcgtt cagtgaagaa    4500
acagcaattc aaaataaatt gacagcgttt gttgttttac caaaagattt aaatgatttt    4560
ggtcctgcgt ggattgaaag atttgttcgt gttcaaatcg aagaagcatt tgcagtggcg    4620
cttgaaactg cgttcttaaa aggtactggt aaagaccaac cgattggctt aaaccgtcaa    4680
gtacaaaaag gtgtatcggt aactgatggt gcttatccag agaagaaga caaggtacg     4740
cttacatttg ctaatccgcg cgctacggtt aatgaattga cgcaagtgtt taaataccac    4800
tcaactaacg agaaaggtaa atcagtagcg gttaaaggta atgtaacaat ggttgttaat    4860
ccgtccgatg cttttgaggt tcaagcacag tatacacatt taaatgcaaa tggcgtatat    4920
gttactgctt taccatttaa tttgaatgtt attgagtcta cagttcaaga agcaggtaag    4980
gttttaacgt acgttaaagg tctatatgat ggttatttag ctggtggtat taatgttcag    5040
aaatttaaag aaacacttgc gttagatgat atggattat acactgcaaa acaatttgct     5100
tacggcaaag cgaaagataa taaagttgct gctgtttgga aattagattt aaaaggacat    5160
aaaccagctt tagaagatac cgaagaaaca ctataaaatt ttatgaggtg ataaaatggt    5220
gaaatttaaa gttgttagag aatttaaaga catagagcac aatcaacaca gtacaaagt     5280
agggagttg tatccagctg aagggtataa caatcctcgt gttgaattgt tgacaaatca     5340
aatcaaaaat aagtacgaca agtttatat cgtaccttta gataagctga caaaacaaga     5400
attattagaa ctatgcgaat cattacaaaa aaaagcgtct agttcaatgg ttaaaagtga    5460
aatcatcgac ttattgaatg gtgaagacaa tgacgattga tgatttgctt gtcaaattta    5520
aatcacttga aaagattgac cataattcag aggatgagta cttaaagcag ttgttaaaaa    5580
tgtcgtacga gcgtataaaa aatcagtgcg gagttttttga attagagaat ttaataggtc    5640
aagaattgat acttatacgc gctagatatg cttatcaaga tttattagaa cacttcaacg    5700
acaattacag acctgaaata atagattttt cgttatctct aatggaggta tcagaagatg    5760
aagaaagtgt ttaagaaacc tagaattaca actaaacgtt taaatacgcg tgttcatttt    5820
tataagtata ctgaaaataa tggtccagaa gctggagaaa aagaagaaaa attattatat    5880
agctgttggg cgagtattga tggtgtctgg ttacgtgaat tagaacaagc tatctcaaac    5940
ggaacgcaaa atgacattaa attgtatatt cgtgatccgc aaggtgatta tttacccagt    6000
gaagaacatt atcttgaaat tgaatcaaga tatttcaaaa atcgtttgaa tataaagcaa    6060
gtatcaccag atttggataa taaagacttt attatgattc gcggaggata tagttcatga    6120
gtgtgaaagt gacaggtgat aaagcattag aaagagaatt agaaaaacat tttggcataa    6180
aagagatggt aaaagttcaa gataaggcgt taatagctgg tgctaaggta attgttgaag    6240
aaataaaaaa acaactcaaa ccttcagaag actcaggagc actgattagt gagattggtc    6300
gtactgaacc tgaatggata aaggggaaac gtactgttac aattaggtgg cgtgggcctt    6360
ttgaacgatt tagaatagta catttaattg aaaatggtca tgttgagaaa agtcaggaa    6420
aatttgtaaa acctaaagct atgggtggga ttaatagagc aataagacaa gggcaaaata    6480
agtattttga gacgctaaaa agggagttga aaaaattgtg attgatattt tgtacaaagt    6540
tcatgaagtg attagtcaag acagaattat tagagagcac gtaaatatca ataatattaa    6600
gttcaataaa tacctaatg taaaagatac tgatgtacct tttattgtta ttgacgatat     6660
cgacgaccca atacctacaa cttatactga cggagatgag tgtgcatata gttatattgt    6720
ccaaatagat gtttttgtta agtacaatga tgaatataat gcgagaatca taagaaataa    6780
```

```
gatatctaat cgcattcaaa agttattatg gtctgaacta aaaatgggaa atgtttcaaa   6840
tggaaaaccg gaatatatag aagaatttaa aacatataga agctctcgcg tttacgaggg   6900
cattttttat aaggaggaaa attaaatggc agtaaaacat gcaagtgcgc caaggcgta    6960 tattaacatt actggtttag gtttcgctaa attaacgaaa gaaggcgcgg aattaaaata   7020
tagtgatatt acaaaaacaa gaggattaca aaaaattggt gttgaaactg gtggagaact   7080
aaaaacagct tatgctgatg gcggtccaat tgaatcaggg aatacagacg gagaaggtaa   7140
aatctcatta caaatgcatg cgttcccaa agagattcgc aaaattgttt ttaatgaaga    7200
ttatgatgaa gatggcgttt acgaagagaa acaaggtaaa caaaacaatt acgtagctgt   7260
atggttcaga caagagcgta aagacggtac atttagaaca gttttattac ctaaagttat   7320
gtttacaaat cctaaaatcg atggagaaac ggctgagaaa gattgggatt tctcaagtga   7380
agaggttgaa ggtgaggcac ttttcccttt agttgataat aaaaagtcag tacgtaagta   7440
tatctttgat tcagctaaca tgacaaatca tgatggagac ggtgaaaaag gcgaagaggc   7500
tttcttaaag aaaattttag gcgaagaata tactggaaac gtgacagagg gtaacgaaga   7560
aactttgtaa caaaaccggc ttcatcggaa actgcggtaa agtcggttaa tataccagat   7620
agcattaaaa cacttaaagt tggcgacaca tacgatttaa atgttgtagt agagccatct   7680
aatcaaagta agttattgaa atacacaaca gatcaaacga atattgtatc aatcaatagt   7740
gatggtcaag ttactgcgga agcacaaggc attgctacgg ttaaagcaac agttggtaat   7800
atgagtgaca ctataacaat aaatgtagaa gcataagagg gggcaacccc tctattttat   7860
ttgaaaataa ggagagtatt ataaaatggc aaaattaaaa cgtaacatta ttcaattagt   7920
agaagatcca aaagcaaatg aaattaaatt acaaacgtac ttaacaccac acttcatttc   7980
atttgaaatt gtatacgaag caatggattt aatcgatgat attgaggacg aaaatagcac   8040
gatgaagcca agagaaatcg ctgacagatt gatggatatg gttgtaaaaa tttacgataa   8100
ccaattcaca gttaaagacc taaaagaacg tatgcatgca cctgatggaa tgaatgcact   8160
tcgtgaacaa gtgattttca ttactcaagg tcaacaaact gaggaaacta gaaattttat   8220
ccagaacatg aaataaagcc tgaagattta acatataaag caatgttgaa aaatatggat   8280
actctcatga tggacttaat tgaaaatggt aaagacgcta acgaagtttt aaaaatgcca   8340
tttcattatg tgcttttccat atatcaaaat aaaaataatg acatttctga agaaaaagca   8400
gaggctttaa ttgatgcatt ttaaccttaa ccgtttggtt agggttattt ttttgaactt   8460
ttttagaaag gaggtaaaaa atgggagaaa gaataaaagg tttatctata ggtttggatt   8520
tagatgcagc aaatttaaat agatcatttg cagaaatcaa acgaaacttt aaaactttaa   8580
attctgactt aaaattaaca ggcaacaact tcaaatatac cgaaaaatca actgatagtt   8640
acaaacaaag gattaaagaa cttgatggaa ctatcacagg ttataagaaa aacgttgatg   8700
atttagccaa gcaatatgac aaggtatctc aagaacaggg cgaaaacagt gcagaagctc   8760
aaaagttacg acaagaatat aacaaacaag caaatgagct gaattattta gaaagagaat   8820
tacaaaaaac atcagccgaa tttgaagagt tcaaaaaagc tcagttgaa gctcaaagaa    8880 tggcagaaag tggctgggga aaaccagta agttttttga agtatggga cctaaattaa     8940 caaaaatggg tgatggttta aaatccattg gtaaaggttt gatgattggt gtaactgcac   9000
ctgttttagg tattgcagca gcatcaggaa aagcttttgc agaagttgat aaaggtttag   9060
atactgttac tcaagcaaca ggcgcaacag gcagtgaatt aaaaaaattg cagaactcat   9120
```

-continued

```
ttaaagatgt ttatggcaat tttccagcag atgctgaaac tgttggtgga gttttaggag      9180
aagttaatac aaggttaggt tttacaggta agaacttga aaatgccaca gagtcattct      9240
tgaaattcag tcatataaca ggttctgacg gtgtgcaagc cgtacagtta attacccgtg      9300
caatgggcga tgcaggtatc gaagcaagtg aatatcaaag tgttttggat atggtagcaa      9360
aagcggcgca agctagtggg ataagtgttg atacattagc tgatagtatt actaaatacg      9420
gcgctccaat gagagctatg ggctttgaga tgaaagaatc aattgcttta ttctctcaat      9480
gggaaaagtc aggcgttaat actgaaatag cattcagtgg tttgaaaaaa gctatatcaa      9540
attggggtaa agctggtaaa aacccaagag aagaatttaa aagacatta gcagaaattg      9600
aaaagacgcc ggatatagct agcgcaacaa gtttagcgat tgaagcattt ggtgcaaagg      9660
caggtcctga tttagcagac gctattaaag gtggtcgctt tagttatcaa gaattttttaa     9720
aaactattga agattcccaa ggcacagtaa accaaacatt taaagattct gaaagtggct      9780
ccgaaagatt taaagtagca atgaataaat taaaattagt aggtgctgat gtatgggctt      9840
ctattgaaag tgcgtttgct cccgtaatgg aagaattaat caaaaagcta tctatagcgg      9900
ttgattggtt ttccaatttta agtgatggtt ctaaaagatc aattgttatt ttcagtggta     9960
ttgctgctgc aattggtcct gtagtttttg ggttaggtgc atttataagt acaattggca     10020
atgcagtaac tgtattagct ccattgttag ctagtattgc aaaggctggt ggattgatta     10080
gtttttttatc gactaaagta cctatattag gaactgtctt cacagcttta actggtccaa     10140
ttggcattgt attaggtgta ttggctggtt tagcagtcgc atttacaatt gcttataaga     10200
aatctgaaac atttagaaat tttgttaatg gtgcaattga aagtgttaaa caaacattta     10260
gtaattttat tcaatttatt caacctttcg ttgattctgt taaaacatc tttaaacaag     10320
cgatatcagc aatagttgat ttcgcaaaag atatttggag tcaaatcaat ggattcttta     10380
atgaaacgg aatttccatt gttcaagcac ttcaaaatat atgcaacttt attaaagcga     10440
tatttgaatt tatttaaat tttgtaatta aaccaattat gttcgcgatt tggcaagtga     10500
tgcaatttat ttggccggcg gttaaagcct tgattgtcag tacttgggag aacataaaag     10560
gtgtaataca aggtgcttta aatatcatac ttggcttgat taagttcttc tcaagtttat     10620
tcgttggtga ttggcgagga gtttgggacg ccgttgtgat gattcttaaa ggagcagttc     10680
aattaatttg gaatttagtt caattatggt ttgtaggtaa aatacttggt gttgttaggt     10740
actttggcgg gttgctaaaa ggattgatag caggaatttg ggacgtaata agaagtatat     10800
tcagtaaatc tttatcagca atttggaatg caacaaaaag tattttttgga ttttattttta    10860
atagcgtaaa atcaatttttc acaaatatga aaaattggtt atctaatact tggagcagta     10920
tccgtacgaa tacaatagga aaagcgcagt cattatttag tggcgtcaaa tcaaaattta     10980
ctaattttatg gaatgcgacg aaagaaattt ttagtaatt aagaaattgg atgtcaaata     11040
tttggaattc cattaaagat aatacggtag gaattgcaag ccgtttatgg agtaaggtac     11100
gtggaatttt cacaaatatg cgcgatggct tgagttccat tatagataag attaaaagtc     11160
atatcggcgg tatggtaagc gctattaaaa aaggacttaa taattaatc gacggtttaa      11220
actgggtcgg tggtaagttg ggaatggata aaatacctaa gttacacact ggtacagagc     11280
acacacatac tactacaaga ttagttaaga acggtaagat tgcacgtgac acattcgcta     11340
cagttgggga taagggacgc ggaaatggtc caaatggttt tagaaatgaa atgattgaat     11400
tccctaacgg taaacgtgta atcacaccta atacagatac taccgcttat ttacctaaag     11460
gctcaaaagt atacaacggt gcacaaaactt attcaatgtt aaacggaacg cttccaagat     11520
```

```
ttagtttagg tactatgtgg aaagatatta aatctggtgc atcatcggca tttaactgga   11580
caaaagataa aataggtaaa ggtaccaaat ggcttggcga taaagttggc gatgttttag   11640
attttatgga aaatccaggc aaacttttaa attatatact tgaagctttt ggaattgatt   11700
tcaattcttt aactaaaggt atgggaattg caggcgacat aacaaaagct gcatggtcta   11760
agattaagaa aagtgctact gattggataa aagaaaattt agaagctatg ggcggtggcg   11820
atttagtcgg cggaatatta gaccctgaca aaattaatta tcattatgga cgtaccgcag   11880
cttataccgc tgcaactgga agaccatttc atgaaggtgt cgatttttcca tttgtatatc   11940 aagaagttag aacgccgatg ggtggcagac ttacaagaat gccatttatg tctggtggtt   12000
atggtaatta tgtaaaaatt actagtggcg ttatcgatat gctatttgcg catttgaaaa   12060
actttagcaa atcaccacct agtggcacga tggtaaagcc cggtgatgtt gttggtttaa   12120
ctggtaatac cggatttagt acaggaccac atttacattt tgaaatgagg agaaatggac   12180
gacattttga ccctgaacca tatttaagga atgctaagaa aaaggaaga ttatcaatag   12240 gtggtggcgg tgctacttct ggaagtggcg caacttatgc cagtcgagta atccgacaag   12300
cgcaaagtat tttaggtggt cgttataaag gtaaatggat tcatgaccaa atgatgcgcg   12360
ttgcaaaacg tgaaagtaac taccagtcaa atgcagtgaa taactgggat ataaatgctc   12420
aaagaggaga cccatcaaga ggattattcc aaatcatcgg ctcaacttttt agagcaaacg   12480 ctaaacgtgg atatactaac tttaataatc cagtacatca aggtatctca gcaatgcagt   12540
acattgttag acgatatggt tggggtggtt ttaaacgtgc tggtgattac gcatatgcta   12600
caggtggaaa agtttttgat ggttggtata acttaggtga agacggtcat ccagaatgga   12660
ttattccaac agatccagct cgtagaaatg atgcaatgaa gattttgcat tatgcagcag   12720
cagaagtaag agggaaaaaa gcgagtaaaa ataagcgtcc tagccaatta tcagacttaa   12780
acgggtttga tgatcctagc ttattattga aaatgattga acaacagcaa caacaaatag   12840
ctttattact gaaaatagca caatctaacg atgtgattgc agataaagat tatcagccga   12900
ttattgacga atacgctttt gataaaaagg tgaacgcgtc tatagaaaag cgagaaaggc   12960
aagaatcaac aaaagtaaag tttagaaaag gaggaattgc tattcaatga tagacactat   13020
taaagtgaac aacaaaacaa ttccttggtt gtatgtcgaa agagggtttg aaatacctc   13080 ttttaattat gttttaaaaa cagaaaatgt agatggacgt tcgggtctta tatataagg   13140 gcgtaggctt gaatcttata gttttgatat accttttggtg gtacgtaatg actatttatc   13200
tcacaacggc attaaaacac atgatgacgt cttgaatgaa ttagtaaagt tttttaacta   13260
cgaggaacaa gttaaattac aattcaaatc taaagattgg tactggaacg cttatttcga   13320
aggaccaata aagctgcaca aagaatttac aatacctgtt aagttcacta tcaaagtagt   13380
actaacagac ccttacaaat attcagtaac aggaaataaa aatactgcga tttcagacca   13440
agtttcagtt gtaaatagtg ggactgctga cactcctttta attgttgaag cccgagcaat   13500
taaaccatct agttacttta tgattactaa aaatgatgaa gattatttta tggttggtga   13560
tgatgaggta accaaagaag ttaaggatta catgcctcct gtttatcata gtgagtttcg   13620
tgatttcaaa ggttggacta agatgattac tgaagatatt ccaagtaatg acttaggtgg   13680
taaggtcggc ggtgactttg tgatatccaa tcttggcgaa ggatataaag caactaatttt   13740 tcctgatgca aaaggttggg ttggtgctgg cacgaaacga gggctcccta aagcgatgac   13800
agattttcaa attacctata aatgtattgt tgaacaaaaa ggtaaaggtg ccggaagaac   13860
```

```
agcacaacat atttatgata gtgatggtaa gttacttgct tctattggtt atgaaaataa    13920
atatcatgat agaaaaatag gacatattgt tgttacgttg tataaccaaa aaggagaccc    13980
caaaaagata tacgactatc agaataaacc gataatgtat aacttggaca gaatcgttgt    14040
ttatatgcgg ctcagaagag taggtaataa attttctatt aaaacttgga aatttgatca    14100
cattaaagac ccagatagac gtaaacctat tgatatggat gagaaagagt ggatagatgg    14160
cggtaagttt tatcagcgtc cagcttctat catagctgtc tatagtgcga agtataacgg    14220
ttataagtgg atggagatga atgggttagg ttcattcaat acggagattc taccgaaacc    14280
gaaaggcgca agggatgtca ttatacaaaa aggtgattta gtaaaaatag atatgcaagc    14340
aaaaagtgtt gtcatcaatg aggaaccaat gttgagcgag aaatcgtttg gaagtaatta    14400
tttcaatgtt gattctgggt acagtgaatt aatcatacaa cctgaaaacg tctttgatac    14460
gacggttaaa tggcaagata gatatttata gaaaggagat gagagtgtga tacatgtttt    14520
agattttaac gacaagatta tagatttcct ttctactgat gacccttcct tagttagagc    14580
gattcataaa cgtaatgtta atgacaattc agaaatgctt gaactgctca tatcatcaga    14640
aagagctgaa aagttccgtg aacgacatcg tgttattata agggattcaa acaaacaatg    14700
gcgtgaattt attattaact gggttcaaga tacgatggac ggctacacag agatagaatg    14760
tatagcgtct tatcttgctg atataacaac agctaaaccg tatgcaccag gcaaatttga    14820
gaaaaagaca acttcagaag cattgaaaga tgtgttgagc gatacaggtt gggaagtttc    14880
tgaacaaacc gaatacgatg gcttacgtac tacgtcatgg acttcttatc aaactagata    14940
tgaagtttta aagcaattat gtacaaccta taaaatggtt ttagattttt atattgagct    15000
tagctctaat accgtcaaag gtagatatgt agtactcaaa aagaaaaaca gcttattcaa    15060
aggtaaagaa attgaatatg gtaaagattt agtcgggtta actaggaaga ttgatatgtc    15120
agaaatcaaa acagcattaa ttgctgtggg acctgaaaat gacaaaggga agcgtttaga    15180
gctagttgtg acagatgacg aagcgcaaag tcaattcaac ctacctatgc gctatatttg    15240
ggggatatat gaaccacaat cagatgatca aaatatgaat gaaacacgat taagttcttt    15300
agccaaaaca gagttaaata aacgtaagtc ggcagttatg tcatatgaga ttacttctac    15360
tgatttggaa gttacgtatc cgcacgagat tatatcaatt ggcgatacag tcagagtaaa    15420
acatagagat tttaacccgc cattgtatgt agaggcagaa gttattgctg aagaatataa    15480
cataatttca gaaaatagca catatacatt cggtcaacct aaagagttca agaatcaga    15540 attacgagaa gagtttaaca agcgattgaa cataatacat caaaagttaa acgataatat    15600
tagcaatatc aacactatag ttaaagatgt tgtagatggt gaattagaat actttgaacg    15660
caaaatacac aaaagtgata caccgccaga aaatccagtc aatgatatgc tttggtatga    15720
tacaagtaac cctgatgttg ctgtcttgcg tagatattgg aatggtcgat ggattgaagc    15780
aacaccaaat gatgttgaaa aattaggtgg tataacaaga gagaaagcgc tattcagtga    15840
attaaacaat atttttatta atttatctat acaacacgct agtctttgt cagaagctac    15900 agaattactg aatagcgagt acttagtaga taatgatttg aaagcggact acaagcaag    15960 tttgacgct gtgattgatg tttataatca aattaaaaat aatttagaat ctatgacacc    16020
cgaaactgca acgattggtc ggttggtaga tacacaagct ttatttcttg agtatagaaa    16080
gaaattacaa gatgtttata cagatgtaga agatgtcaaa atcgccattt cagatagatt    16140
taaattatta cagtcacaat acactgatga aaaatataaa gaagcgttgg aaataatagc    16200
aacaaaattt ggtttaacgg tgaatgaaga tttgcagtta gtcggagaac ctaatgttgt    16260
```

```
taaatcagct attgaagcag ctagagaatc cacaaaagaa caattacgtg actatgtaaa    16320
aacatcggac tataaaacag acaaagacgg tattgttgaa cgtttagata ctgctgaagc    16380
tgagagaacg actttaaaag gtgaaatcaa agataaagtt acgttaaacg aatatcgaaa    16440
cggattggaa gaacaaaaac aatatactga tgaccagtta agtgatttgt ccaataatcc    16500
tgagattaaa gcaagtattg aacaagcaaa tcaagaagcg caagaagctt taaaatcata    16560
cattgatgct caagatgatc ttaaagagaa ggaatcgcaa gcgtatgctg atggtaaaat    16620
ttcggaagaa gagcaacgcg ctatacaaga tgctcaagct aaacttgaag aggcaaaaca    16680
aaacgcagaa ctaaggcta gaaacgctga aagaaagct aatgcttata cagacaacaa     16740
ggtcaaagaa agcacagatg cacagaggaa acattgact cgctatggtt ctcaaattat      16800
acaaaatggt aaggaaatca attaagaac tactaaagaa gagtttaatg caaccaatcg      16860
tacactttca aatatattaa acgagattgt tcaaaatgtt acagatggaa caacaatcag    16920
atatgatgat aacggagtgg ctcaagcttt gaatgtgggg ccacgtggta ttagattaaa    16980
tgctgataaa attgatatta acgtaatag agaaataaac cttcttatcc aaaatatgcg     17040
agataaagta gataaaaccg atattgtcaa cagtcttaat ttatcaagag agggtcttga    17100
tatcaatgtt aatagaattg gaattaaagg cggtgacaat aacagatatg ttcaaataca    17160
gaatgattct attgaactag gtggtattgt gcaacgtact tggagaggga acgttcaac    17220 agacgatatt tttacgcgac tgaaagacg tcacctaaga tttagaaata caccgctgg      17280 cggttcactt tatatgtcac attttggtat ttcgacttat attgatggtg aaggtgaaga    17340
cggtggttca tctggtacga ttcaatggtg ggataaaact tacagtgata gtggcatgaa    17400
tggtataaca atcaattcct atggtggtgt cgttgcacta acgtcagata taatcgggt    17460 tgttctggag tcttacgctt catcgaatat caaaagcaaa caggcaccgg tgtatttata    17520
tccaaacaca gacaaagtgc ctggattaaa ccgatttgca ttcacgctgt ctaatgcaga    17580
taatgcttat tcgagtgacg gttatattat gtttggttct gatgagaact atgattacgg    17640
tgcgggtatc aggttttcta agaaagaaa taaggtctt gttcaaattg ttaatggacg      17700
atatgcaaca ggtggagata caacaatcga agcagggtat ggcaaattta atatgctgaa    17760
acgacgtgat ggtaataggt atattcatat acagagtaca gacctactgt ctgtaggttc    17820
agatgatgca ggagatagga tagcttctaa ctcaatttat agacgtactt attcggccgc    17880
agctaatttg catattactt ctgctggcac aattgggcgt tcgacatcag cgcgtaaata    17940
caagttatct atcgaaaatc aatataacga tagagatgaa caactggaac attcaaaagc    18000
tattcttaac ttacctatta gaacgtggtt tgataaagct gagtctgaaa ttttagctag    18060
agagctgaga gaagatagaa aattatcgga agacacctat aaacttgata gatacgtagg    18120
tttgattgct gaagaggtgg agaatttagg attaaaagag tttgtcacgt atgatgacaa    18180
aggagaaatt gaaggtatag cgtatgatcg tctatggatt catcttatcc ctgttatcaa    18240
agaacaacaa ctaagaatca agaaattgga ggagtcaaag aatgcaggat aacaaacaag    18300
gattacaagc taatcctgaa tatacaattc attatttatc acaggaaatt atgaggttaa    18360
cacaagaaaa cgcgatgtta aaagcgtata tacaagaaaa taaagaaaat caacaatgtg    18420
ctgaggaaga gtaatcctta gcactatttt tatacaaaaa tttaaggagg tcatttaatt    18480
atggcaaaag aaattatcaa caatacagaa aggtttattt tagtacaaat cgacaaagaa    18540
ggtacagaac gtgtagtata tcaagatttc acaggaagtt ttacaacttc tgaaatggtt    18600
```

-continued

```
aaccatgctc aagattttaa atctgaagaa aacgctaaga aaattgcgga gacgttaaat   18660
ttgttatatc aattaactaa caaaaaacaa cgtgtgaaag tagttaaaga agtagttgaa   18720
agatcagatt tatctccaga ggtaacagtt aacactgaaa cagtatgaaa agctatgagt   18780
tagatactca tagtctttat tcttttagaa agcgggtgta ctgaattggg gtggttcaaa   18840
aaacacgaac atgaatggcg catcagaagg ttagaagaga atgataaaac aatgctcagc   18900
acactcaacg aaattaaatt aggtcaaaaa acccaagagc aagttaacat taaattagat   18960
aaaaccttag atgctattca aaagaaaga gaaatagatg aaaagaataa gaaagaaaat   19020
gataagaaca tacgtgatat gaaaatgtgg gtgcttggtt tagttgggac aatatttggg   19080
tcgctaatta tagcattatt gcgtatgctt atgggcatat aagagaggtg attaccatgt   19140
tcggattaaa ttttggagct tcgctgtgga cgtgtttctg gtttggtaag tgtaagtaat   19200
agttaagagt cagtgcttcg gcactggctt tttattttgg ataaaaggag caaacaaatg   19260
gatgcaaaag taataacaag atacatcgta ttgatcttag cattagtaaa tcaattctta   19320
gcgaacaaag gtattagccc aattccagta gacgatgaaa ctatatcatc aataatactt   19380
actgtagtcg ctttatatac aacgtataaa gacaatccaa catctcaaga aggtaaatgg   19440
gcaaatcaaa aattaaagaa atataaagct gaaataagt atagaaaagc aacagggcaa   19500
gcgccaatta aagaagtaat gacacctacg aatatgaacg acacaaatga tttagggtag   19560
gtggttgata tatgttaatg acaaaaaatc aagcagaaaa atggtttgac aattcattag   19620
ggaaacaatt caacccagat ggttggtatg gatttcagtg ttatgattac gccaatatgt   19680
tctttatgtt agcgacaggc gaaaggctgc aaggtttata tgcttataat atcccgtttg   19740
ataataaagc aaagattgaa aaatatggtc aaataattaa aaactatgac agcttttac   19800 cgcaaaagtt ggatattgtc gttttcccgt caaagtatgg tggcggagct ggacacgttg   19860
aaattgttga gagcgcaaat ttaaatactt tcacatcatt tggtcaaaac tggaacggta   19920
aaggttggac taatggcgtt gcgcaacctg gttggggtcc tgaaactgtg acaagacatg   19980
ttcattatta tgacaatcca atgtatttta ttaggttaaa cttccctaac aacttaagcg   20040
ttggcaataa agctaaaggt attattaagc aagcgactac aaaaaaagag gcagtaatta   20100
aacctaaaaa aattatgctt gtagccggtc atggttataa cgatcctgga gcagtaggaa   20160
acggaacaaa cgaacgcgat tttatacgta aatatataac gcctaatatc gctaagtatt   20220
taagacatgc aggacatgaa gttgcattat acgtggctc aagtcaatca caagatatgt   20280
atcaagatac tgcatacggt gttaatgtag gcaataaaaa agattatggc ttatattggg   20340
ttaaatcaca ggggtatgac attgttctag aaatacattt agacgcagca ggagaaagcg   20400
caagtggtgg gcatgttatt atctcaagtc aattcaatgc agatactatt gataaaagta   20460
tacaagatgt tattaaaaat aacttaggac aaataagagg tgtgacacct cgtaatgatt   20520
tactaaatgt taatgtatca gcagaaataa atataaatta tcgtttatct gaattaggtt   20580
ttattactaa taaaaatgat atggattgga ttaagaaaaa ctatgacttg tattctaaat   20640
taatagccgg tgcgattcat ggtaagccta taggtggttt ggtagctggt aatgttaaaa   20700
catcagctaa aaacaaaaaa aatccaccag tgccagcagg ttatacactc gataagaata   20760
atgtccctta taaaaagaa caaggcaatt acacagtagc taatgttaaa ggtaataatg   20820
taagagacgg ttattcaact aattcaagaa ttacagggt attacccaac aacacaacaa   20880
ttacgtatga cggtgcatat tgtattaatg gttatagatg gattacttat attgctaata   20940
gtggacaacg tcgttatata gcgacaggag aggtagacaa ggcaggtaat agaataagta   21000
```

-continued

```
gttttggtaa gtttagcacg atttagtatt tacttagaat aaaaattttg ctacattaat    21060
tatagggaat cttacagtta ttaaataact atttggatgg atgttaatat tcctatacac    21120
tttttaacat ttctctcaag atttaaatgt agataacagg caggtacttc ggtacttgcc    21180 tatttttta tgttatagct agccttcggg ctagttttt gttatgatgt gttacacatg     21240
catcaactat ttacatctat ccttgttcac ccaagcatgt cactggatgt ttttcttgc    21300 gatagagagc atagttttca tactactccc cgtagtatat atgactttag cattcccgta    21360
taacagttta cggggtgctt ttatgttata attgctttta tatagtagga gtgaactata    21420
tagccgggca gaggccatgt atctgactgt tggtcccaca ggagacatct tccttgtcat    21480
cactcgatac atatatctta acaacataga aatgttacat tcgctataac cgtatcttaa    21540
tcgatacggt tatatttatt ccccctacaac caacaaaacc acagatccta ttaatttagg   21600
attgtggtta ttttttgcgt ttttttgggg caaaaaagg gcagattatt tgaaaaaggg     21660
caaacgcttg tggaaaagct aaaaggttaa aaatgacaaa aaccttgata caacagtgtt    21720
tttggacgct cgtgtacgtt agagaatgac cggtttacca tcatacaagg gtgggattaa    21780
cttgtgttaa aaagccttta atatcagttg ttacaaagga tttgtagcgt cttaaaaat    21840 aaaaagggc agaaaaaggg cagatacctt ttagtacaca agttttcta attttgctc      21900 taactctctg tccatttct ctgttacatg tgtatacacc tttatagtcg tttttcatc     21960 tgtatgtcct actctttttca taattgcttt taacgtata ttcattccg ccaataaact    22020 tatgtgtgta tgccttagtg tgtgagtagt aacttttta tttatattta atgattctgc    22080
agctgaggac aatcgtttgt ttatcctact gccttgcata ggatttcctt ggcaagttgt    22140
gaatataaac cctctatcaa catagcttgg ttcccattgt tgcatctttt tattttctaa    22200 cattatttt ttcaatacat ttgctatcct tgaattgatg gcgattttc ttcttgaacc     22260 tgcggtctta gtagtatctt tgtgaccaaa tccagcatta catttgattc tgtgaatagt    22320
gccattaata gcgatcgttt tatttttgag gtcaacatct ttaacttgga gagctaataa    22380
ctcacctatg cgcataccctg ttaaagcttg aacttctaca gccccagcaa ctaaaatacg  22440
agctctatac tgcatgttat tatcgttcag tataaaatcg cgtatctgta ttacctgttc   22500
catctctaaa tagttataca ttttcgcttc ttcttttct atatcttcta tcgtcttact   22560
cttctttggt agtgtgacgc tatttaatat gtgttcgttt ggataattgt aaaatttaac   22620
ggcgtattta atagcttctt tcatatgtcc aagttgacgc tttacctgat ttgcagaata   22680
tacgtttgat aatttgttaa taaatgtttg catgtacttt gtatcaattt tgtttaaaag   22740
taaattttga gaactgttct ttttgatgtt tttgattctt gttttcaaat tatcaagcgt   22800
cgttacttta aagccagatg ttttatatg atattcaagc cattcatcta ataacgcgtg    22860
aaaagtcaaa gttttaatt cgcttgacga cttgttgttt agttttctt ttatttttc     22920 ttctaaacga aacattgcct cttttgcga ttgctttgta ttcttattca agacaacact    22980
tacacgtttc catttatctg tatacggatc tttgtatttc tcgtagtatc tatacttcgt   23040
ttcattgttc ttattttaa atttttcaaa ccacatttta catccctcct caaaattggc    23100
aaaaaataat aagggtaggc gggctaccca tgaaaattgt ataaaaaag acgcctgtat    23160 aaaatacaga cgccacttat aattataaga ttacatggtt aattaccaaa aatggtaacg   23220
aatatatacg tgttttaaag gataaacctt taatatatta aaattatatc atcttatatc   23280
agggatctgc aatatattat tattaattct atttatcagt aacataatat ccgaagaatc   23340
```

```
tattactgga ttttttaattt tttggggtaa aacttttctt atgcgaaact tactaatcgg    23400
ctggaaagaa tttatgcaag cgtaactatt acctttttaat tttttttacct tatcaattgc   23460 tgatactatg ttattaatgt ttctgtcaat tttatttaat ttattttcaa tttctaaact    23520
atcagatata aattcaataa aataatcttt agtgatgaat tctgtgttgt ttttttggta    23580 tttttttatcg aaaacttctt ttaatatagc tgaattattt tgcgcgctaa ttaaatttaa   23640
aaacaatctt aaataatact cccatttcaa atcaaaattc atctttaaat acttttttgtt  23700 ttctttagag gataagggaa taacattac tatatcctcc gtattagaat catttttatt    23760
catcactatt gcaaagtgtg aattagaaaa ttctttatta acgtttatac cgaaatctac   23820
aaaaactatt tctccttgtt taaactttgg ataaaaacct ttatggtttt tttcaccttc   23880
aaatctcttg agtaaatagt gaatatctga atctaacttt ttaaattttg gatttccaga   23940 agttttttaat ttattaatgc gttttttctat attatgcgtc atcatttctc ctttattctc 24000
gctcacactc tcaccaccat tcaacgtcta cacttgtagg cgttttttga ttagtaaaat  24060
cataatgaat cttctttggt taacttatcg ccatctatttt tttgtgaaat aaattccaag  24120
tatttacgcg cattatgtga cgataaatct ttaggtaact cataagtgaa tggttgatta   24180
ccactagtta aaacttcata tactatagtt tctttttttta ttttgcaatt agttattttc 24240
attataaact ccttttaaac actgctgaaa tagacgtctt tttcaaataa gcatgattaa   24300
tactttaatt cttaatcca catatatttta aaagtgaggt agtaggtaat aaatataaga   24360
cttaaagtta agattgcttt tttcatgtca atttctcctt tgtttatatt tatattaaag   24420
cgctaaatat acgttattaa tcacaataca actttgccca ttactttaat atcactaaac  24480
gaagcgactt tgatatcatc atacttcgga tttagagata ccaaattaat atagtcttcg  24540
catatatcta cacgcttgat aagacttact ccatctaata caacgagtgc aattgtacca  24600
tctttaatag aatcttcttt cttaataaaa gcgtatgttc cttgttttaa cataggttcc  24660
attgaatcac cattaactaa aatacaaaaa tcagcatttg atggcgtttc gtcttctttta 24720 aaaaatactt cttcatgcaa tatgtcatca tataattctt ctcctatgcc agcaccagtt   24780
gcaccacatg caatatacga tactagttta gactctttat attcatctat agaagtgact   24840
ttattctgtt catctaattg ctcatttgca tagttaagta cgttttcttg gcggggaggt   24900
gtgagttgag aaaatatgtt attgattttt gacattatcg tttcatcttg acgttcttcg   24960
tcaggaactc gataagaatc tacatcatac cccataagcc acgcttcacc gacatttaaa  25020
gttttagata ataagaataa tttatgttgg tctggagaag accttccatt aacatactgg  25080
gataagtgac ttttttgacat tttaatattc aattcttttt gaaagggttt cgacttttct  25140
agaatatcta cttgacgcaa gttcctatct ttcataattt gttttaatct ttcagaagtg   25200
ttttgcattg gtaatgcctc cttgaaattc attatatagg aagggaaata aaaatcaata   25260
caaaagttca actttttttaa ctttttgtgt tgacattgtt caaaattggg gttatagtta  25320
ttatagttca aatgtttgaa cttaggaggt gattatttga atactaatac aacttttgat   25380
ttttcgttat tgaacggtaa gatagtcgaa gtgtactcga cacaatttaa ctttgctata   25440
gctttaggtg tatcagaaag aactttgtct ttgaagttga acaacaaagt accatggaaa  25500
acaacagaca ttattaaagc ttgtaagtta ttgggaatac ctataaaaga tgttcacaaa  25560 tatttttttta aacagaaagt tcaaatgttt gaacttaata agtaaaggag gcataacaca  25620
tgcaagaacg agaaaaggtt aataaaagta acacatcttc aaatgaagca tcaaaacctt  25680
ttaggacaaa ttgaagctta cgacaaaacg cttaaagaaa taaagtacac tcgagacctt  25740
```

```
tacaacaaac acctaagcat gaacaacgaa gacgcattcg ctggtttgga aatggtagag   25800
gatgaaatta ctaaaaagct acgaagtgct atcaaagagt tccaaaaagt agtgaaagcg   25860
ttagacaagc ttaacggtgt tgaaagcgat aacaaagtta ctgatttaac agagtggcgg   25920
aaagtgaatc agtaacattc acttcttaat ataaccacgc ttatcaacat ccacattgag   25980
cagatgtgag cgagagctgg cgatgatatg agccgcgttt aaatacattc gatagtcatt   26040
gcgataaccg tctgctgaat gtgggtgttg aggaaaaagg aggatactca aatgcaagca   26100
ttacaaacat ttaattttaa agagctacca gtaagaacag tagaaattga aaacgaacct   26160
tattttgtag gaaaagatat tgctgagatt ttaggatatg caagatcaaa caatgccatt   26220
agaaatcatg ttgatagcga ggacaagctg acgcaccaat ttagtgcatc aggtcaaaac   26280
agaaatatga tcattatcaa cgaatcagga ttatacagtc taatcttcga tgcttctaaa   26340
caaagcaaaa acgaaaaaat tagagaaacc gctagaaaat tcaaacgctg ggtaacatca   26400
gatgtcctac cagctattcg caaacacggt atatacgcaa cagacaatgt aattgaacaa   26460
acattaaaag atccagacta catcattaca gtgttgactg agtataagaa agaaaaagag   26520
caaaacttac ttttacaaca gcaagtagaa gttaacaaac caaaagtatt attcgctgac   26580
tcggtagctg gtagtgataa ttcaatactt gttggagaac tagcgaaaat acttaaacaa   26640
aacggtgttg atataggaca aaacagattg ttcaaatggt taagaaataa tggatatctc   26700
attaaaaaga gtggagaaag ttataactta ccaactcaaa agagtatgga tctaaaaatc   26760
ttggatatca aaaaacgaat aattaataat ccagatggtt caagtaaagt atcacgtaca   26820
ccaaaagtaa caggcaaagg acaacaatac tttgttaata agtttttagg agaaaaacaa   26880
acatcttaaa aggaggaaca caatggaaca aatcacatta accaaagaag agttgaaaga   26940
aattatagca aaagaagtta gagaggctat aaatggcaag aaaccaatca gttcaggttc   27000
aattttcagt aaagtaagaa tcaataatga cgatttagaa gaaatcaata aaaaactcaa   27060
tttcgcaaaa gatttgtcgc taggaagatt gaggaagctc aatcatccga ttccgctaaa   27120
aaagtatcag catggcttcg aatcaattca tcaaaaagct tatgtacaag atgttcatga   27180
ccatattaga aaattaacat tatcaatttt tggagtgaca cttaattcag acttgagtga   27240
aagtgaatac aacctagcag caaaagttta tcgagaaatc aaaaactatt atttatacat   27300
ctatgaaaag agagtttcag aattaactat cgatgatttc gaataaagga ggaacaacaa   27360
atgttacaaa aatttagaat tgcgaaagaa aaaataaat taaaactcaa attactcaag   27420
catgctagtt actgtttaga aagaaacaac aaccctgaac tgttgcgagc agttgcagag   27480
ttgttgaaaa aggttagcta aattcaacgg taaggatttg ccctgcctcc acacttagag   27540
tttgagatcc aacaaacaca taagtttag tagggtctag aaaaaatgtt tcgatttcct   27600
cttttgtaac agtttcaatt ccttcatatc ctggaaaaac aattttcttt aaatccgaaa   27660 catgttttttt tgaaccatcc tttaaagtaa ctagaagttt catacttatc acctccttag   27720
gttgataaca acattataca cgaaaggagc ataaacaata tgcaagcatt acaaacaaat   27780
tcgaacatcg gagaaatgtt caatattcaa gaaaagaaa atggagaaat cgcaatcagc   27840
ggtcgagaac ttcatcaagc attagaagtt aagacagcat ataagattg gtttccaaga   27900 atgcttaaat acggatttga agaaaataca gattacacag ctatcgctca aaaaagagca   27960
acagctcaag gcaatatgac tcactatatt gaccacgcac tcacactaga cactgcaaaa   28020
gaaatcgcaa tgattcaacg tagtgaacct ggcaaacgtg caagacaata tttcatccaa   28080
```

-continued

```
gttgaaaaag catggaacag cccagaaatg attatgcaac gtgctttaaa aattgctaac    28140
aacacaatca atcaattaga aacaaagatt gcacgtgaca aaccaaaaat tgtatttgca    28200
gatgcagtag ctactactaa gacatcaatt ttagttggag agttagcaaa gatcattaaa    28260
caaaacggta taaacatcgg gcaacgcaga ttgtttgagt ggttacgtca aaacggattc    28320
cttattaaac gcaagggtgt ggattataac atgcctacac agtattcaat ggaacgtgag    28380
ttattcgaaa ttaaagaaac atcaatcaca cattcggacg gtcacacatc aattagtaag    28440
acgccaaaag taacaggtaa aggacaacaa tactttgtta acaagttttt aggagaaaaa    28500
caaacaactt aataggagga attacaaatg aacgcactat acaaaacaac cctcctcatc    28560
acaatggcag ttgtgacgtg gaaggtttgg aagattgaga agcacactag aaaacctgtg    28620
attagtagca gggcgttgag tgactatcta aacaacaaat ctttaaccat accgaaagat    28680
gctgaaaatt ctactgaatc tgctcgtcgc cttttgaagt tcgccgaaca aactattagc    28740
aaataacaac attatacacg aaaggaaaga tagaaatgcc aaaaatcata gtaccaccaa    28800
caccagaaaa cacatataga ggcgaagaaa aatttgtgaa aaagttatac gcaacaccta    28860
cacaaatcca tcaattgttt ggagtatgta gaagtacagt atacaactgg ttgaaatatt    28920
accgcaaaga taatttaggt gtagaaaatt tatacattga ttattcacca acaggcactc    28980
tgattaatat ttctaaattg gaagagtatt tgatcagaaa gcataaaaaa tggtattagg    29040
aggatattaa atgagcaaca tttataaaag ctacctagta gcagtattat gcttcacagt    29100
cttagcgatt gtacttatgc cgtttctata cttcactaca gcatggtcaa ttgcgggatt    29160
cgcaagtatc gcaacattca tgtactacaa agaatgcttt ttcaaagaat aaaaaaactg    29220
ctacttgttg gagcaagtaa cagtatcaaa cacttaagaa aaaattcatg ttcaatataa    29280
aacgaaaaac ggaggaagtc aagatgtatt acgaatagg cgaaatcata cgcaaaaata    29340
ttcatgttaa cggattcgat tttaagctat tcattttaaa aggtcatatg gcatatcaa    29400
tacaagttaa agatatgaac aacgtaccaa ttaaacatgc ttatgtcgta gatgagaatg    29460
acttagatat ggcatcagac ttatttaacc aagcaataga tgaatggatt gaagagaaca    29520
cagacgaaca ggacagacta attaacttag tcatgaaatg gtaggaggtc gctatgaagc    29580
agactgtaac ttatatcatt cgtcataggg atatgccaat ttatataact aacaaaccaa    29640
ctgataacaa ttcagatatt agttactcca caaatagaaa tagagctagg gagtttaacg    29700
gtatggaaga agcgagtatc aatatggatt atcacaaagc aatcaagaaa acagtgcag    29760
aaactattga gtacgaggag gtagaacatg actgaggaaa acaagaacc acaagaaaaa    29820
gtaagcatac tcaaaaaact aaagataaat aatatcgctg agaaaaataa aaggaaattc    29880
tataaatttg cagtatacgg aaaaattggc tcaggaaaaa ccacgtttgc tacaagagat    29940
aaagacgctt tcgtcattga cattaacgaa ggtggaacaa cggttactga cgaaggatca    30000
gacgtagaaa tcgagaacta tcaacacttt gtttatgttg taaatttttt acctcaaatt    30060
ttacaggaga tgagagaaaa cggacaagaa atcaatgttg tagttattga aactattcaa    30120
aaacttagag atatgacatt gaatgatgtg atgaaaaata agtctaaaaa accaacgttt    30180
aatgattggg gagaagttgc tgaacgaatt gtcagtatgt acagattaat aggaaaactt    30240
caagaagaat acaaattcca ctttgttatt acaggtcatg aaggtatcaa caaagataaa    30300
gatgatgaag gtagcactat caaccctact atcactattg aagcgcaaga acaaattaaa    30360
aaagctatta cttctcaaag tgatgtgtta gctagggcaa tgattgaaga atttgatgat    30420
aacggagaaa agaaagctag atatattcta aacgctgaac cttctaatac gtttgaaaca    30480
```

-continued

```
aagattagac attcaccttc aataacaatt aacaataaga aatttgcaaa tcctagcatt    30540
acggacgtag tagaagcaat tagaaatgga aactaaaaat taattaaaag gacggtattt    30600
aattatgaaa atcacaggac aagcgcaatt tactaaagaa acaaatcaag aaaagtttta    30660
taacggctca gcagggtttc aagctggaga attcacagtg aaagttaaaa atattgaatt    30720
caatgataga gaaaatagat atttcacaat cgtatttgaa aatgatgaag gcaaacaata    30780
taaacataat caatttgtac cgccgtataa atatgatttc caagaaaaac aattgattga    30840
attagttact cgattaggta ttaagttaaa tcttcctagc ttagattttg ataccaatga    30900
tcttattggt aagttttgtc acttggtatt gaaatggaaa ttcaatgaag atgaaggtaa    30960
gtattttacg gatttttcat ttattaaacc ttacaaaaag ggcgatgatg ttgttaacaa    31020
acctattccg aagacagata agcaaaaagc tgaagaaaat aacggggcac aacaacaaac    31080
atcaatgtct caacaaagca atccatttga aagcagtggc caatttggat atgacgacca    31140
agatttagcg ttttaaggtg tggtttaaat gcaatacatt acaagatacc agaaagataa    31200
cgacggtact tattccgtcg ttgctactgg tgttgaactt gaacaaagtc acattgactt    31260
actagaaaac ggatatccac taaaagcaga agtagaggtt ccggacaata aaaaactatc    31320
tatagaacaa cgcaaaaaaa tattcgcaat gtgtagagat atagaacttc actggggcga    31380
accagtagaa tcaactagaa aattattaca aacagaattg gaaattatga aaggttatga    31440
agaaatcagt ctgcgcgact gttctatgaa agttgcaagg gagttaatag aactgattat    31500
agcgtttatg tttcatcatc aaatacctat gagtgtagaa acgagtaagt tgttaagcga    31560
agataaagcg ttattatatt gggctacaat caaccgcaac tgtgtaatat gcggaaagcc    31620
tcacgcagac ctggcacatt atgaagcagt cggcagaggc atgaacagaa acaaaatgaa    31680
ccactatgac aaacatgtat tagcgttatg tcgcgaacat cacaacgagc aacatgcgat    31740
tggcgttaag tcgtttgatg ataaatacca cttgcatgac tcgtggataa agttgatga    31800 gaggctcaat aaaaatgttga aaggagagaa aaaggaatga atagactaag aataataaaa    31860
atagcactcc taatcgtcat cttggcggaa gagattagaa atgctatgca tgctgtaaaa    31920
gtggagaaaa ttttaaaatc tccgtttagt aatacaggt ttttacaaaa gctttaccat    31980
aggcggacaa actaattgag ccttttttga tgtctattac ccaggggctg taatgtaact    32040
ttaatacttc aaattcaatg ccagaaagtt tacttattgt ttctaggttg tgtcctgact    32100
ttaacattct tttaacaaat tctaatcccg aaacaaatct ttgttttttct ataatcttat    32160 taaagtgatt taaaaactga ggagcataaa acttattata aattcctttt tttgttaagt    32220
aagacatgtc aaaagtttca tttaaaaccc ctaaccttac taggttatta attgaaattt    32280
cggttgattc tatatctaac ggagagtctt ttattaacgt gtccgatata ttcataccgt    32340
cattctttgg gtttaaaacc gctctatatt taacggcagg atgtacttcg tgattcttta    32400
aatgttttaa aagaatagca tcatttgggg ataattgttt aattatttca acaaatgaat    32460
ggtgggttaa tgagtttttt ctgtcatcca tagatgatgc tattagtttt gcgaacatat    32520
tacttaaagt tttttcacta atgtaaaact ttgaagcttc tagagcagga cctagaagag    32580
aaaattgtgg ttcttgtaaa ttatttttag gtacagaaga tatttctttt ttaaattgtt    32640
ctttgaattt ttcaaattct acttctcttt gataaataac tttatccaca taaaggtgga    32700
atttcccaaa gacaagttcc caagttttag agaatgtttc tacaggccct tttgatgcgc    32760
cttcaataat tttatcaata cctttaccta aaataggatc cataattatt cacccccaat    32820
```

```
ctaacgcaat agcgataata aaattatacc agaaaggaga atcaacatga ctgaccaacc   32880
aagttactac tcaataatta cagcaaatgt cagatacgat aaccgactta ctgacagcga   32940
aaagttactt tttgcagaaa taacatcttt aagtaacaaa tacggatact gcacagcaag   33000
taatggttac tttgcaactt tatacaacgt tgttaaggaa actatatctc gtagaatttc   33060
gaaccttacc aactttggtt atctaaaaat cgaaattatc aaagaaggta atgaagttaa   33120
acaaaggaag atgtacccct tgacgcaaac gtcaatacct attgacgcaa aaatcaatac   33180
ccctattgat aattctgtca ataccccctat tgacgcaaat gtcaaagaga atattacaag   33240
tattaataat acaagtaata acaatataaa tagaatagat atattgtcgg caacccgac   33300 agcatcttct atacctata aagaaattat cgattactta acaaaaaag cgggcaagca   33360 ttttaaacac aatacagcta aaacaaaga ttttattaaa gcaagatgga atcaagattt   33420
taggttggag gatttaaaa aggtgattga tatcaaaaca gctgagtggc taaacacgga   33480
tagcgataaa taccttagac cagaaacact ttttggcagt aaatttgagg ggtacctcaa   33540
tcaaaaaata caaccaactg gcacggatca attggaacgc atgaagtacg acgaaagtta   33600
ttgggattag ggggatatta tgaaaccact attcagcgaa aagataaacg aaagcttgaa   33660
aaaatatcaa cctactcatg tcgaaaaagg attgaaatgt gagagatgtg gaagtgaata   33720
cgacttatat aagtttgctc ctactaaaaa acacccgaat ggttacgagt ataaagacgg   33780
ttgcaaatgt gaaatctatg aggaatataa gcgaaacaag caacggaaga taaacaacat   33840
attcaatcaa tcaaacgtta atccgtcttt aagagatgca acagtcaaaa actacaagcc   33900
acaaaatgaa aaacaagtac acgctaaaca aacagcaata gagtacgtac aaggcttctc   33960
tacaaaagaa ccaaaatcat taatattgca aggttcatac ggaactggta aaagccacct   34020
agcatacgct atcgcaaaag cagtcaaagc taaagggcat acggttgctt ttatgcacat   34080
accaatgttg atggatcgta tcaaagcgac atacaacaaa aatgcagtag agactacaga   34140
cgagctagtc agattgctaa gtgatattga tttacttgta ctagatgata tgggtgtaga   34200
aaacacagag cacactttaa ataaactttt cagcattgtt gataacagag taggtaaaaa   34260
caacatcttt acaactaact ttagtgataa agaactaaat caaaatatga actggcaacg   34320
tataaattcg agaatgaaaa aaagagcaag aaaagtaaga gtaatcggag acgatttcag   34380
ggagcgagat gcatggtaac caaagaattt ttaaaaacta aacttgagtg ttcagatatg   34440
tacgctcaga aactcataga tgaggcacag ggcgatgaaa ataggttgta cgacctattt   34500
atccaaaaac ttgcagaacg tcatacacgc cccgctatcg tcgaatatta aggagtgtta   34560
aaaatgccga agaaaaaata ttacttatac cgagaagatg gcacagaaga tattaaggtc   34620
atcaagtata aagacaacgt aaatgaggtt tattcgctca caggagccca tttcagcgac   34680
gaaaagaaaa ttatgactga tagtgaccta aaacgattca aaggcgctca cgggcttcta   34740
tatgagcaag aattaggttt acaagcaacg atatttgata tttagaggtg gacgatgagt   34800
aaatacaacg ctaagaaagt tgagtacaaa ggaattgtat ttgatagcaa agtagagtgt   34860
gaatattacc aatatttaga aagtaatatg aatggcacta attatgatca tatcgaaata   34920
caaccgaaat tcgaattatt accaaaacta gataaacaac gaaagattga atatattgca   34980
gacttcgcgt tatatctcga tggcaaactg attgaagtta tcgacattaa aggtatgcca   35040
accgaagtag caaaacttaa agctaagatt ttcagacata atacagaaa cataaaactc   35100 aattggatat gtaaagcgcc taagtataca ggtaaaacat ggattacgta cgaggaatta   35160
attaaagcaa gacgagaacg caaaagagaa atgaagtgat ctaatgcaac aacaagcata   35220
```

```
tataaatgca acgattgata taaggatacc tacagaagtt gaatatcagc attttgatga    35280
tgtggataaa gaaaaagaag cgctggcaga ttacttatat aacaatcctg acgaaatact    35340
agagtatgac aatttaaaaa ttagaaacgt aaatgtagag gtggaataaa tgggcagtgt    35400
tgtaatcatt aataataaac catataaatt taacaatttt gaaaaaagaa ataatggcaa    35460
agcgtgggat aaatgctgga attgtttcta acgtgttag aggttgttgg gagttttcag    35520
aagctttaga cgcgccttat ggcatgcacc taaaagaata tagagaaatg aaacaaatgg    35580
aaaagattaa acaagcgaga ctcgaacgtg aattggaaag agagcgaaag aaagaggctg    35640
agctacgtaa gaagaagcca catttgttta atgtacctca aaaacattca cgtgatccgt    35700
actggttcga tgtcacttat aaccaaatgt tcaagaaatg gagtgaagca taatgagcat    35760
aatcagtaac agaaaagtag atatgaacaa aacgcaagac aacgttaagc aacctgcgca    35820
ttacacatac ggcgacattg aaattataga ttttattgaa caagttacgg cacagtaccc    35880
accacaatta gcattcgcaa taggtaatgc aattaaatac ttgtctagag caccgttaaa    35940
gaatggtcat gaggatttag caaaggcgaa gttttacgtc gatagagtat ttgacttgtg    36000
ggagtgatga ccatgacaga tagcggacgt aaagaatact taaaacattt tttcggctct    36060
aagagatatc tgtatcagga taacgaacga gtggcacata tccatgtagt aaatggcact    36120
tattactttc acggtcatat cgtgccaggt tggcaaggtg tgaaaaagac atttgataca    36180
gcggaagagc ttgaaacata tataaagcaa agtgatttgg aatatgagga acagaagcaa    36240
ctaactttat tttaaaaggg cggaaacaat gaaaatcaaa attgaaaaag aaatgaattt    36300
acctgaactt atccaatggg cttgggataa ccccaagtta tcaggtaata aaagattcta    36360
ttcaaatgat gttgagcgca actgttttgt gacttttcat gttgatagca tcttatgtaa    36420
tgtgactgga tatgtatcaa ttaacgataa atttactgtt caagaggaga tataacaatg    36480
aaaatcaaag ttaaaaaaga aatgagatta gatgaattaa ttaaatgggc gcgagaaaat    36540
ccggatctat cacaaggaaa aatattttt tcaacaggat ttagtgatgg attcgttcgt    36600
tttcatccaa atacaaataa gtgttcgacg tcaagtttta ttccaattga tatccccttc    36660
atagttgata ttgaaaaaga agtaacggaa gagactaagg ttgataggtt gattgaatta    36720
ttcgagattc aagaaggaga ctataactct acactatatg agaacactag tataaaagaa    36780
tgtttatatg gcagatgtgt gcctaccaaa gcattctaca tcttaaacga tgacctaact    36840
atgacgttaa tctggaaaga tggggagttg ctagtatgat gttgaaattt aaagcttggg    36900
ataaagataa aaaagttatg agtattattg acgaaatcga ttttaatagt gggtacattt    36960
tgatttcaac aggttataaa agtttcaatg aagtaaaact attacaatac acaggattta    37020
aagatgtgca cggtgtggag atttatgaag gggatattgt tcaagattgt tattcgagag    37080
aagtaagttt tatcgagttt aaagaaggag ccttttatat aacttttagc aatgtaactg    37140
aattactaag tgaaaatgac gatattattg aaattgttgg aaatattttt gaaaatgaga    37200
tgctattgga ggttatgaga tgacgttcac cttatcagat gaacaatata aaaatctttg    37260
tactaactct aacaagttat tagataaact tcacaaagca ttaaaagatc gtgaagagta    37320
caagaagcaa cgagatgagc ttattgggga tatagcgaag ttcgagatt gtaacaaaga    37380 tctagagaag aaagcaagcg catgggatag gtattgcaag agcgttgaaa aagatttaat    37440
aaacgaattc ggtaacgatg atgaaagagt taaattcgga atggaattaa acaataaaat    37500
ttttatggag gatgacacaa atgaataatc gcgaaaaaat cgaacagtcc gttattagtg    37560
```

```
ctagtgcgta taacggtaat gacacagagg ggttgctaaa agagattgag gacgtgtata    37620
agaaagcgca agcgtttgat gaaatacttg agggaatgac aaatgctatt caacattcag    37680
ttaaagaagg tattgaactt gatgaagcag tagggattat ggcaggtcaa gttgtctata    37740
aatatgagga ggaataggaa aatgactaac acattacaag taaaactatt atcaaaaaat    37800
gctagaatgc ccgaacgaaa tcataagacg gatgcaggtt atgacatatt ctcagctgaa    37860
actgtcgtac tcgaaccaca agaaaaagca gtgatcaaaa cagatgtagc tgtgagtata    37920
ccagagggct atgtcggact attaactagt cgtagtggtg taagtagtaa aacgtattta    37980
gtgattgaaa caggcaagat agacgcggga tatcatggca atttagggat taatatcaag    38040
aatgatgaag aacgtgatgg aataccettt ttatatgatg atatagacgc tgaattagaa    38100
gatggattaa taagcatttt agatataaaa ggtaactatg tacaagatgg aagaggcata    38160
agaagagttt accaaatcaa caaaggcgat aaactagctc aattggttat cgtgcctata    38220
tggacaccgg aactaaagca agtggaggaa ttcgaaagtg tttcagaacg tggagcaaaa    38280
ggcttcggaa gtagcggagt gtaaagacat cttagatcga gttaaggagg ttttggggaa    38340
gtgacgcaat acttagtcac aacattcaaa gattcaacag gacgaccaca tgaacatatt    38400
actgtggcta gagataatca gacgtttaca gttattgagg cagagagtaa agaagaagcg    38460
aaagagaagt acgaggcaca agttaaaaga gatgcagtta ttaaagtggg tcagttgtat    38520
gaaaatataa gggagtgtgg gaaatgacgg atgttaaaat taaaactatt tcaggtggag    38580 tttatttttgt aaaacagct gaaccttttg aaaaatatgt tgaaagaatg acgagtttta    38640
atggttatat ttacgcaagt actataatca agaaaccaac gtatattaaa acagatacga    38700
ttgaatcaat cacacttatt gaggagcatg ggaaatgaat cagctgagaa ttttattaca    38760
tgacggtagt agtttgatat tacatgaaga tgaattattt aacgaaatag tatttgtttt    38820
ggacaatttt agaaatgatg atgactattt aacgatagaa aaagattatg gcagagaact    38880
tgtattgaac aaaggttata tagttgggat caatgttgag gaggcagatg atgattaaca    38940
tacctaaaat gaaattcccg aaaaagtaca ctgaaataat caaaaaatat aaaaataaag    39000
cacctgaaga aaaggctaag attgaagatg atttttattaa agaaattaaa gataaagaca    39060 gtgaattta cagtcctacg atggctaata tgaatgaata tgaattaagg gctatgttaa    39120
gaatgatgcc tagtttaatt gatactggag atgacaatga tgattaaaaa acttaaaaat    39180
atggatgggt tcgacatctt tattgttgga atactgtcat tattcggtat attcgcattg    39240
ctacttgtta tcacattgcc tatctataca gtggctagtt accaacacaa agaattacat    39300
caaggaacta ttcagataa atataacaag agacaagata aagaagacaa gttctatatt    39360
gtattagaca caaacaagt cattgaaaat tccgacttat tattcaaaaa gaaatttgat    39420
agcgcagata tacaagctag gttaaaagta ggcgataagg tagaagttaa aacaatcggt    39480
tatagaatac actttttaaa tttatatccg gtcttatacg aagtaaagaa ggtagataaa    39540
caatgattaa acaaatacta agactattat tcttactagc aatgtatgag ttaggtaagt    39600
atgtaactga gcaagtgtat attatgatga cggctaatga tgatgtagag gcgccgagtg    39660
attacgtctt tcgagcggag gtgagtgaat aatgagaata tttatttatg atttgatcgt    39720
tttgctgttt gctttcttaa tatccatata tattattgat gatggagtga taataaatgc    39780
attaggaatt tttggtatgt ataaaattat agattccttt tcagaaaata ttataaagag    39840
gtagataaaa atgaacgagc aaataatagg aagcatatat actttagcag gaggtgttgt    39900
gctttattca gttaaagaga ttttaggta ttttacagat tctaacttac aacgtaaaaa    39960
```

```
aatcaatttta gaacaaatat atccgatata tttagattgt tttaaaaagg ctaaaaagat    40020
gattggagct tatattattc caacagaaca gcatgaattt ttagattttt ttgatattga    40080
agtctttaat aatttagata agcaaagtaa aaaagcgtat gaaaatgtta ttggatttag    40140
acaaatgatt aatttatcaa atagagttaa ggcaatggaa gattttaaga tgagtttcaa    40200
caatgaattt agtacaaatc agatttttt  taatccttct tttgttatgg aaacaattgc    40260
tattataaat gaatatcaaa aagatatatc ttatttaaaa aatataatta ataaatgaa    40320 tgaaaataga gcttataatc atattgatag ttttatcact tcagagtacc gacgaaaaat    40380
aaacgattat aatctttatc ttgataaatt tgaagaacag tttagtcaaa agtttaaaat    40440
aaacagaact tcgataaaag aaagaattat tattaattta aacaagagga gatttaaatg    40500
atgtggatta ctatgactat tgtatttgct atattgctat tagtttgtat cagtattaat    40560
agtgatcgtg caagagagat acaagcactt agatatatga atgattatct acttgatgaa    40620
gtagttaaaa ctaaagggta caacgggtta gaagaataca ggattgaatt gaagcgaatg    40680
aataacgata ttaaaaagta atttatatta tcggaggtat tgcattgaat gataaagatt    40740
gagaaacacg atatcaaaaa gcttgaagaa tacattcagc acatcgataa ctatcgaaga    40800
gagttgaaga tgcgagaata tgaattactt gaaagtcatg aaccagataa tgcgggagct    40860
ggcaaaagta atttgccggg taacccgatt gaacgatgtg caataaagaa gtttagtgat    40920
aacaggtaca atacattaag aaatatagtt aacggtgtag atagattgat aggtgaaagt    40980
gatgaggata cgcttgagtt attaaggttt agatattggg attgtcctat tggttgttat    41040
gaatgggaag atatagcaca ttactttggt acaagtaaga caagtatatt acgtagaagg    41100
aatgcactga tcgataagtt agcaaagtat attggttatg tgtagcggac tttttaccta    41160
tgtaagtccg cattaaaaca gtttattatg ttagtatcag attaatattt aaagttatta    41220
aatgctaata cgacgcatga acaagaggcg catcactatg tgatgtgtct ttttatttat    41280
gaggtatgaa catgttcaaa ctaattgtaa atacattact acacatcaag tatagatgag    41340
tcttgatact acttaagtta tataaggtga acattatga  tgactaaaga cgaacgtata    41400
cgattctata agtctaaaga atggcaaata acaagaaaaa gagtgctaga agagataat    41460 tatgaatgtc aacaatgtaa gagagacggc aagttaacga catatgacaa agcaagcgt    41520 aagtcgttgg atgtagatca tatattatcg ctagaacatc atccggagtt tgctcatgac    41580
ttaaacaatt tagaaacact gtgtattaaa tgtcacaaca aaaagaaaa  gagatttata    41640 aaaaagaaa  ataatggaa agacgaaaaa tggtaaatac ccccgggtca aaaaaatcaa    41700
aagcgatc                                                            41708
```

<210> SEQ ID NO 4
<211> LENGTH: 159
<212> TYPE: DNA
<213> ORGANISM: Staphylococcus aureus

<400> SEQUENCE: 4

```
atggtaacca aagaattttt aaaaactaaa cttgagtgtt cagatatgta cgctcagaaa     60
ctcatagatg aggcacaggg cgatgaaaat aggttgtacg acctatttat ccaaaaactt    120
gcagaacgtc atacacgccc cgctatcgtc gaatattaa                           159
```

<210> SEQ ID NO 5
<211> LENGTH: 52
<212> TYPE: PRT

<213> ORGANISM: Staphylococcus aureus

<400> SEQUENCE: 5

```
Met Val Thr Lys Glu Phe Leu Lys Thr Lys Leu Glu Cys Ser Asp Met
1               5                   10                  15

Tyr Ala Gln Lys Leu Ile Asp Glu Ala Gln Gly Asp Glu Asn Arg Leu
            20                  25                  30

Tyr Asp Leu Phe Ile Gln Lys Leu Ala Glu Arg His Thr Arg Pro Ala
        35                  40                  45

Ile Val Glu Tyr
    50
```

<210> SEQ ID NO 6
<211> LENGTH: 1362
<212> TYPE: DNA
<213> ORGANISM: Bacillus subtilis

<400> SEQUENCE: 6

```
atgacagacc ttctgaatga ccggcttcct ccgcaaaata tagaagccga acaagccgtg      60
ttaggcgcta ttttttttaca gccgtctgct ttaacactgg cttcagaagt attgattcca    120
gatgatttct atagaatgtc ccaccaaaaa atctataatg cgatgctggt gctcggtgac    180
cgaggtgaac cggttgatct ggtgacagtt acatcagagc ttgcgaacac agacctgctg    240
gaagaagtag gcggtatttc atatttgaca gatatcgcaa actcggtgcc gacagcggct    300
aacatagaat tacgcgaaa atcgttgag gaaaaatcga ttcttcgccg attaatcaga      360
actgcgacaa cgattgctca agacgggtat acccgtgagg atgaggtcga ggatttactc    420
agtgaagcgg aaaaaacgat tatggaagtg cacagcgca aaaacacgag tgccttccaa     480
aatattaagg acgtccttgt ccagacctat gataatatcg aacagcttta caatcgaaaa    540
ggtgatatca cggaattcc aacagggttt acggagcttg accggatgac tgcgggtttc     600
cagcgcaacg acttgatcat tgtggctgcc cgtccttcag tagggaaaac agcctttgcc    660
ctgaacatcg cacaaaacgt ggcgacgaag accgatgaga gcgtagcgat tttcagtctt    720
gagatgggtg ccgagcagct cgttatgcgt atgctctgtg ccgagggaaa tatcaatgcc    780
cagaatctcc gtacaggtaa cctgaccgaa gaggattggg gcaagctgac gatggcaatg    840
ggaagcctat cgaacagcgg gatttacatc gatgatacac cgggtattcg agtgagtgaa    900
atccgtgcca gtgccgccg cttgaagcag gaaagcgggc tggcatgat tttgatcgat      960
tacctgcaat tgattcaggg aagcggtcgt tcaaaggaca accgtcagca ggaagtatct   1020
gaaatttccc gtgaactgaa gtcgattgcg agggagctgc aagtccctgt tatcgcgctt   1080
tctcagcttt ccagggggtgt tgagcagcgt caggataaac gtccgatgat gtctgatatc   1140
cgggaatcag gaagtatcga gcaggacgcg gatattgtcg cgttcctta tcgtgatgac    1200
tactatgaca agaaaccga gaataaaaat attatcgaaa ttattatcgc caaacagcgt    1260
aacggcccgg taggaaccgt gtctcttgcg ttcgtaaaag aatacaacaa attcgtcaac   1320
ctggaacggc gttttgatga cgcaggcgtt ccgcccggcg ca                      1362
```

<210> SEQ ID NO 7
<211> LENGTH: 1401
<212> TYPE: DNA
<213> ORGANISM: Staphylococcus aureus

<400> SEQUENCE: 7

```
atggatagaa tgtatgagca aaatcaaatg ccgcataaca tgaagctga acagtctgtc      60
```

-continued

```
ttaggttcaa ttattataga tccagaattg attaatacta ctcaggaagt tttgcttcct      120
gagtcgtttt ataggggtgc ccatcaacat attttccgtg caatgatgca cttaaatgaa      180
gataataaag aaattgatgt tgtaacattg atggatcaat tatcgacgga aggtacgttg      240
aatgaagcgg gtggcccgca atatcttgca gagttatcta caaatgtacc aacgacgcga      300
aatgttcagt attatactga tatcgtttct aagcatgcat taaaacgtag attgattcaa      360
actgcagata gtattgccaa tgatggatat aatgatgaac ttgaactaga tgcgattta      420
agtgatgcag aacgtcgaat tttagagcta tcatcttctc gtgaaagcga tggctttaaa      480
gacattcgag acgtcttagg acaagtgtat gaaacagctg aagagcttga tcaaaatagt      540
ggtcaaacac caggtatacc tacaggatat cgagatttag accaaatgac agcagggttc      600
aaccgaaatg atttaattat ccttgcagcg cgtccatctg taggtaagac tgcgttcgca      660
cttaatattg cacaaaaagt tgcaacgcat gaagatatgt atacagttgg tattttctcg      720
ctagagatgg gtgctgatca gttagccaca cgtatgattt gtagttctgg aaatgttgac      780
tcaaaccgct taagaacggg tactatgact gaggaagatt ggagtcgttt tactatagcg      840
gtaggtaaat tatcacgtac gaagattttt attgatgata caccgggtat tcgaattaat      900
gatttacgtt ctaaatgtcg tcgattaaag caagaacatg gcttagacat gattgtgatt      960
gactacttac agttgattca aggtagtggt tcacgtgcgt ccgataacag acaacaggaa     1020
gtttctgaaa tctctcgtac attaaaagca ttagcccgtg aattagaatg tccagttatc     1080
gcattaagtc agttatctcg tggtgttgaa caacgacaag ataaacgtcc aatgatgagt     1140
gatattcgtg aatctggttc gattgagcaa gatgccgata tcgttgcatt cttataccgt     1200
gatgattact ataaccgtgg cggcgatgaa gatgatgacg atgatggtgg tttcgagcca     1260
caaacgaatg atgaaaacgg tgaaattgaa attatcattg ctaagcaacg taacggtcca     1320
acaggcacag ttaagttaca ttttatgaaa caatataata aatttaccga tatcgattat     1380
gcacatgcag atatgatgta a                                                1401
```

<210> SEQ ID NO 8
<211> LENGTH: 454
<212> TYPE: PRT
<213> ORGANISM: Bacillus subtilis

<400> SEQUENCE: 8

```
Met Thr Asp Leu Leu Asn Asp Arg Leu Pro Pro Gln Asn Ile Glu Ala
1               5                   10                  15

Glu Gln Ala Val Leu Gly Ala Ile Phe Leu Gln Pro Ser Ala Leu Thr
            20                  25                  30

Leu Ala Ser Glu Val Leu Ile Pro Asp Asp Phe Tyr Arg Met Ser His
        35                  40                  45

Gln Lys Ile Tyr Asn Ala Met Leu Val Leu Gly Asp Arg Gly Glu Pro
    50                  55                  60

Val Asp Leu Val Thr Val Thr Ser Glu Leu Ala Asn Thr Asp Leu Leu
65                  70                  75                  80

Glu Glu Val Gly Gly Ile Ser Tyr Leu Thr Asp Ile Ala Asn Ser Val
                85                  90                  95

Pro Thr Ala Ala Asn Ile Glu Tyr Tyr Ala Lys Ile Val Glu Glu Lys
            100                 105                 110

Ser Ile Leu Arg Arg Leu Ile Arg Thr Ala Thr Thr Ile Ala Gln Asp
        115                 120                 125
```

```
Gly Tyr Thr Arg Glu Asp Glu Val Asp Leu Leu Ser Glu Ala Glu
    130                 135                 140
Lys Thr Ile Met Glu Val Ala Gln Arg Lys Asn Thr Ser Ala Phe Gln
145                 150                 155                 160
Asn Ile Lys Asp Val Leu Val Gln Thr Tyr Asp Asn Ile Glu Gln Leu
                165                 170                 175
Tyr Asn Arg Lys Gly Asp Ile Thr Gly Ile Pro Thr Gly Phe Thr Glu
            180                 185                 190
Leu Asp Arg Met Thr Ala Gly Phe Gln Arg Asn Asp Leu Ile Ile Val
        195                 200                 205
Ala Ala Arg Pro Ser Val Gly Lys Thr Ala Phe Ala Leu Asn Ile Ala
    210                 215                 220
Gln Asn Val Ala Thr Lys Thr Asp Glu Ser Val Ala Ile Phe Ser Leu
225                 230                 235                 240
Glu Met Gly Ala Glu Gln Leu Val Met Arg Met Leu Cys Ala Glu Gly
                245                 250                 255
Asn Ile Asn Ala Gln Asn Leu Arg Thr Gly Asn Leu Thr Glu Glu Asp
            260                 265                 270
Trp Gly Lys Leu Thr Met Ala Met Gly Ser Leu Ser Asn Ser Gly Ile
        275                 280                 285
Tyr Ile Asp Asp Thr Pro Gly Ile Arg Val Ser Glu Ile Arg Ala Lys
    290                 295                 300
Cys Arg Arg Leu Lys Gln Glu Ser Gly Leu Gly Met Ile Leu Ile Asp
305                 310                 315                 320
Tyr Leu Gln Leu Ile Gln Gly Ser Gly Arg Ser Lys Asp Asn Arg Gln
                325                 330                 335
Gln Glu Val Ser Glu Ile Ser Arg Glu Leu Lys Ser Ile Ala Arg Glu
            340                 345                 350
Leu Gln Val Pro Val Ile Ala Leu Ser Gln Leu Ser Arg Gly Val Glu
        355                 360                 365
Gln Arg Gln Asp Lys Arg Pro Met Met Ser Asp Ile Arg Glu Ser Gly
    370                 375                 380
Ser Ile Glu Gln Asp Ala Asp Ile Val Ala Phe Leu Tyr Arg Asp Asp
385                 390                 395                 400
Tyr Tyr Asp Lys Glu Thr Glu Asn Lys Asn Ile Ile Glu Ile Ile Ile
                405                 410                 415
Ala Lys Gln Arg Asn Gly Pro Val Gly Thr Val Ser Leu Ala Phe Val
            420                 425                 430
Lys Glu Tyr Asn Lys Phe Val Asn Leu Glu Arg Arg Phe Asp Asp Ala
        435                 440                 445
Gly Val Pro Pro Gly Ala
    450

<210> SEQ ID NO 9
<211> LENGTH: 466
<212> TYPE: PRT
<213> ORGANISM: Staphylococcus aureus

<400> SEQUENCE: 9

Met Asp Arg Met Tyr Glu Gln Asn Gln Met Pro His Asn Asn Glu Ala
1               5                   10                  15
Glu Gln Ser Val Leu Gly Ser Ile Ile Ile Asp Pro Glu Leu Ile Asn
                20                  25                  30
Thr Thr Gln Glu Val Leu Leu Pro Glu Ser Phe Tyr Arg Gly Ala His
            35                  40                  45
```

```
Gln His Ile Phe Arg Ala Met Met His Leu Asn Glu Asp Asn Lys Glu
 50                  55                  60
Ile Asp Val Val Thr Leu Met Asp Gln Leu Ser Thr Glu Gly Thr Leu
 65                  70                  75                  80
Asn Glu Ala Gly Gly Pro Gln Tyr Leu Ala Glu Leu Ser Thr Asn Val
                 85                  90                  95
Pro Thr Thr Arg Asn Val Gln Tyr Tyr Thr Asp Ile Val Ser Lys His
             100                 105                 110
Ala Leu Lys Arg Arg Leu Ile Gln Thr Ala Asp Ser Ile Ala Asn Asp
         115                 120                 125
Gly Tyr Asn Asp Glu Leu Glu Leu Asp Ala Ile Leu Ser Asp Ala Glu
     130                 135                 140
Arg Arg Ile Leu Glu Leu Ser Ser Ser Arg Glu Ser Asp Gly Phe Lys
145                 150                 155                 160
Asp Ile Arg Asp Val Leu Gly Gln Val Tyr Glu Thr Ala Glu Glu Leu
             165                 170                 175
Asp Gln Asn Ser Gly Gln Thr Pro Gly Ile Pro Thr Gly Tyr Arg Asp
         180                 185                 190
Leu Asp Gln Met Thr Ala Gly Phe Asn Arg Asn Asp Leu Ile Ile Leu
     195                 200                 205
Ala Ala Arg Pro Ser Val Gly Lys Thr Ala Phe Ala Leu Asn Ile Ala
210                 215                 220
Gln Lys Val Ala Thr His Glu Asp Met Tyr Thr Val Gly Ile Phe Ser
225                 230                 235                 240
Leu Glu Met Gly Ala Asp Gln Leu Ala Thr Arg Met Ile Cys Ser Ser
             245                 250                 255
Gly Asn Val Asp Ser Asn Arg Leu Arg Thr Gly Thr Met Thr Glu Glu
         260                 265                 270
Asp Trp Ser Arg Phe Thr Ile Ala Val Gly Lys Leu Ser Arg Thr Lys
     275                 280                 285
Ile Phe Ile Asp Asp Thr Pro Gly Ile Arg Ile Asn Asp Leu Arg Ser
     290                 295                 300
Lys Cys Arg Arg Leu Lys Gln Glu His Gly Leu Asp Met Ile Val Ile
305                 310                 315                 320
Asp Tyr Leu Gln Leu Ile Gln Gly Ser Gly Ser Arg Ala Ser Asp Asn
             325                 330                 335
Arg Gln Gln Glu Val Ser Glu Ile Ser Arg Thr Leu Lys Ala Leu Ala
         340                 345                 350
Arg Glu Leu Glu Cys Pro Val Ile Ala Leu Ser Gln Leu Ser Arg Gly
     355                 360                 365
Val Glu Gln Arg Gln Asp Lys Arg Pro Met Met Ser Asp Ile Arg Glu
     370                 375                 380
Ser Gly Ser Ile Glu Gln Asp Ala Asp Ile Val Ala Phe Leu Tyr Arg
385                 390                 395                 400
Asp Asp Tyr Tyr Asn Arg Gly Gly Asp Glu Asp Asp Asp Asp Gly
             405                 410                 415
Gly Phe Glu Pro Gln Thr Asn Asp Glu Asn Gly Glu Ile Glu Ile Ile
             420                 425                 430
Ile Ala Lys Gln Arg Asn Gly Pro Thr Gly Thr Val Lys Leu His Phe
         435                 440                 445
Met Lys Gln Tyr Asn Lys Phe Thr Asp Ile Asp Tyr Ala His Ala Asp
     450                 455                 460
```

```
Met Met
465

<210> SEQ ID NO 10
<211> LENGTH: 313
<212> TYPE: PRT
<213> ORGANISM: Staphylococcus aureus

<400> SEQUENCE: 10

Met Gly Gly Gly Gln Ser Ile Met Lys Gln Phe Lys Ser Ile Ile Asn
1               5                   10                  15

Thr Ser Gln Asp Phe Glu Lys Arg Ile Glu Lys Ile Lys Lys Glu Val
            20                  25                  30

Ile Asn Asp Pro Asp Val Lys Gln Phe Leu Glu Ala His Arg Ala Glu
        35                  40                  45

Leu Thr Asn Ala Met Ile Asp Glu Asp Leu Asn Val Leu Gln Glu Tyr
    50                  55                  60

Lys Asp Gln Gln Lys His Tyr Asp Gly His Lys Phe Ala Asp Cys Pro
65                  70                  75                  80

Asn Phe Val Lys Gly His Val Pro Glu Leu Tyr Val Asp Asn Asn Arg
                85                  90                  95

Leu Lys Ile Arg Tyr Leu Gln Cys Pro Cys Lys Ile Lys Tyr Asp Glu
            100                 105                 110

Glu Arg Phe Glu Ala Glu Leu Ile Thr Ser His Asn Met Gln Arg Asp
        115                 120                 125

Thr Leu Asn Ala Lys Leu Lys Asp Leu Tyr Met Asn His Arg Asp Arg
    130                 135                 140

Leu Asp Val Ala Met Ala Ala Asp Asp Ile Cys Thr Ala Ile Thr Asn
145                 150                 155                 160

Gly Glu Gln Val Lys Gly Leu Tyr Leu Tyr Gly Pro Phe Gly Thr Gly
                165                 170                 175

Lys Ser Phe Leu Leu Gly Ala Ile Ala Asn Gln Leu Lys Ser Lys Lys
            180                 185                 190

Val Arg Ser Thr Ile Ile Tyr Leu Pro Glu Phe Ile Arg Thr Leu Lys
        195                 200                 205

Gly Gly Phe Lys Asp Gly Ser Phe Glu Lys Lys Leu His Arg Val Arg
    210                 215                 220

Glu Ala Asn Ile Leu Met Leu Asp Asp Ile Gly Ala Glu Glu Val Thr
225                 230                 235                 240

Pro Trp Val Arg Asp Glu Val Ile Gly Pro Leu Leu His Tyr Arg Met
                245                 250                 255

Val His Glu Leu Pro Thr Phe Phe Ser Ser Asn Phe Asp Tyr Ser Glu
            260                 265                 270

Leu Glu His His Leu Ala Met Thr Arg Asp Gly Glu Glu Lys Thr Lys
        275                 280                 285

Ala Ala Arg Ile Ile Glu Arg Val Lys Ser Leu Ser Thr Pro Tyr Phe
    290                 295                 300

Leu Ser Gly Glu Asn Phe Arg Asn Asn
305                 310

<210> SEQ ID NO 11
<211> LENGTH: 12
<212> TYPE: PRT
<213> ORGANISM: Staphylococcus aureus
<220> FEATURE:
<221> NAME/KEY: misc_feature
<223> OTHER INFORMATION: predicted tryptic peptide
```

```
<400> SEQUENCE: 11

Gly His Val Pro Glu Leu Tyr Val Asp Asn Asn Arg
1               5                   10

<210> SEQ ID NO 12
<211> LENGTH: 11
<212> TYPE: PRT
<213> ORGANISM: Staphylococcus aureus
<220> FEATURE:
<221> NAME/KEY: misc_feature
<223> OTHER INFORMATION: predicted tryptic peptide

<400> SEQUENCE: 12

Ser Thr Ile Ile Tyr Leu Pro Glu Phe Ile Arg
1               5                   10

<210> SEQ ID NO 13
<211> LENGTH: 14
<212> TYPE: PRT
<213> ORGANISM: Staphylococcus aureus
<220> FEATURE:
<221> NAME/KEY: misc_feature
<223> OTHER INFORMATION: predicted tryptic peptide

<400> SEQUENCE: 13

Ser Leu Ser Thr Pro Tyr Phe Leu Ser Gly Glu Asn Phe Arg
1               5                   10

<210> SEQ ID NO 14
<211> LENGTH: 280
<212> TYPE: PRT
<213> ORGANISM: Bacillus subtilis

<400> SEQUENCE: 14

Asp Gln Asp Val Gln Ala Phe Leu Lys Glu Asn Glu Glu Val Ile Asp
1               5                   10                  15

Gln Lys Met Ile Glu Lys Ser Leu Asn Lys Leu Tyr Glu Tyr Ile Glu
            20                  25                  30

Gln Ser Lys Asn Cys Ser Tyr Cys Ser Glu Asp Glu Asn Cys Asn Asn
        35                  40                  45

Leu Leu Glu Gly Tyr His Pro Lys Leu Val Val Asn Gly Arg Ser Ile
    50                  55                  60

Asp Ile Glu Tyr Tyr Glu Cys Pro Val Lys Arg Lys Leu Asp Gln Gln
65                  70                  75                  80

Lys Lys Gln Gln Ser Leu Met Lys Ser Met Tyr Ile Gln Gln Asp Leu
                85                  90                  95

Leu Gly Ala Thr Phe Gln Gln Val Asp Ile Ser Asp Pro Ser Arg Leu
            100                 105                 110

Ala Met Phe Gln His Val Thr Asp Phe Leu Lys Ser Tyr Asn Glu Thr
        115                 120                 125

Gly Lys Gly Lys Gly Leu Tyr Leu Tyr Gly Lys Phe Gly Val Gly Lys
    130                 135                 140

Thr Phe Met Leu Ala Ala Ile Ala Asn Glu Leu Ala Glu Lys Glu Tyr
145                 150                 155                 160

Ser Ser Met Ile Val Tyr Val Pro Glu Phe Val Arg Glu Leu Lys Asn
                165                 170                 175

Ser Leu Gln Asp Gln Thr Leu Glu Glu Lys Leu Asn Met Val Lys Thr
            180                 185                 190

Thr Pro Val Leu Met Leu Asp Asp Ile Gly Ala Glu Ser Met Thr Ser
```

```
            195                 200                     205

Trp Val Arg Asp Glu Val Ile Gly Thr Val Leu Gln His Arg Met Ser
    210                 215                 220

Gln Gln Leu Pro Thr Phe Phe Ser Ser Asn Phe Ser Pro Asp Glu Leu
225                 230                 235                 240

Lys His His Phe Thr Tyr Ser Gln Arg Gly Glu Lys Glu Val Lys
                245                 250                 255

Ala Ala Arg Leu Met Glu Arg Ile Leu Tyr Leu Ala Ala Pro Ile Arg
                260                 265                 270

Leu Asp Gly Glu Asn Arg Arg His
                275                 280
```

<210> SEQ ID NO 15
<211> LENGTH: 278
<212> TYPE: PRT
<213> ORGANISM: Bacillus halodurans

<400> SEQUENCE: 15

```
Pro His Val Gln Leu Phe Leu Glu Glu His Pro Ser Leu Ser Pro Ile
1               5                   10                  15

Thr Leu Glu Gln Gly Leu Ser Lys Leu Tyr Glu Tyr Gln Lys Glu Gln
                20                  25                  30

Ser His Cys Ala His Cys Pro Gly Leu Gln Lys Cys Pro Asn Leu Met
                35                  40                  45

Lys Gly Tyr Gln Pro Thr Leu Tyr Val Glu Arg Asp Ser Leu Glu Leu
            50                  55                  60

Ser Tyr Ser Pro Cys Pro Leu Lys Glu Glu Glu Arg Glu Lys Lys
65                  70                  75                  80

Lys Arg Ser Leu Ile Arg Ser Leu Tyr Ile Pro Lys Glu Ile Leu Glu
                85                  90                  95

Ala Lys Phe Asp Asp Val Glu Ser Glu Pro Gly Arg Ser Ile Ala Ser
                100                 105                 110

His Arg Ala Leu Glu Phe Ala Leu Ser Ala Lys Pro Gly Glu Asp Gly
            115                 120                 125

Met Gly Leu Tyr Leu Tyr Gly Lys Phe Gly Val Gly Lys Thr Phe Leu
130                 135                 140

Met Gly Ala Ile Ala Asn Glu Leu Lys Asp Arg Gly Ile Asp Ser Thr
145                 150                 155                 160

Ile Val Tyr Val Pro Asp Phe Phe Arg Glu Leu Lys Gln Ser Ile Gly
                165                 170                 175

Asp Gly Thr Phe Gln Gln Lys Leu Asp Phe Val Lys Asn Ala Gln Val
            180                 185                 190

Leu Ile Phe Asp Asp Ile Gly Ala Glu Thr Met Thr Ser Trp Val Arg
            195                 200                 205

Asp Asp Val Leu Gly Val Ile Leu Gln Tyr Arg Ile Met Glu Lys Leu
                210                 215                 220

Pro Thr Leu Phe Thr Ser Asn Tyr Asp Tyr Glu Leu Glu Glu His
225                 230                 235                 240

Leu Ala Tyr Asn Asp Lys Ser Gly Thr Glu Leu Leu Lys Ala Lys Arg
                245                 250                 255

Val Met Glu Arg Ile Arg His Tyr Thr Val Ser Val Met Val Gln Gly
                260                 265                 270

Gln Asn Arg Arg Glu His
                275
```